US009546129B2

(12) United States Patent
Jay et al.

(10) Patent No.: US 9,546,129 B2
(45) Date of Patent: Jan. 17, 2017

(54) DTPA PRODRUGS, COMPOSITIONS THEREOF, AND METHODS OF USING THE SAME

(71) Applicant: The University of North Carolina at Chapel Hill, Chapel Hill, NC (US)

(72) Inventors: Michael Jay, Chapel Hill, NC (US); Russell Mumper, Chapel Hill, NC (US); James Huckle, Chapel Hill, NC (US); Matthew Sadgrove, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/721,552

(22) Filed: May 26, 2015

(65) Prior Publication Data

US 2015/0251991 A1    Sep. 10, 2015

Related U.S. Application Data

(63) Continuation-in-part of application No. PCT/US2013/071738, filed on Nov. 25, 2013.

(60) Provisional application No. 61/729,780, filed on Nov. 26, 2012.

(51) Int. Cl.
*A01N 37/02* (2006.01)
*A01N 37/06* (2006.01)
*A61K 31/225* (2006.01)
*C07C 69/74* (2006.01)
*C07C 229/16* (2006.01)
*C07C 227/00* (2006.01)
*C07D 265/33* (2006.01)

(52) U.S. Cl.
CPC ........... *C07C 229/16* (2013.01); *A61K 31/225* (2013.01); *C07C 227/00* (2013.01); *C07D 265/33* (2013.01)

(58) Field of Classification Search
None
See application file for complete search history.

(56) References Cited

U.S. PATENT DOCUMENTS

| | | |
|---|---|---|
| 4,687,659 A | 8/1987 | Quay |
| 4,780,238 A | 10/1988 | Premuzic |
| 4,859,451 A | 8/1989 | Quay et al. |
| 4,906,463 A | 3/1990 | Cleary et al. |
| 5,250,702 A | 10/1993 | Kondo et al. |
| 5,288,718 A | 2/1994 | Varga et al. |
| 5,403,862 A | 4/1995 | Miller et al. |
| 5,440,031 A | 8/1995 | Varga et al. |
| 5,494,935 A | 2/1996 | Miller et al. |
| 5,780,670 A | 7/1998 | Yamamoto et al. |
| 6,020,373 A | 2/2000 | Schellenberg et al. |
| 6,060,040 A | 5/2000 | Tournier et al. |
| 6,241,968 B1 | 6/2001 | Tournier et al. |
| 7,914,767 B2 | 3/2011 | Shankar et al. |
| 8,030,358 B2 | 10/2011 | Jay et al. |
| 2007/0196273 A1 | 8/2007 | Shankar et al. |
| 2007/0243132 A1 | 10/2007 | Russell-Jones et al. |
| 2009/0124692 A1 | 5/2009 | Jay et al. |
| 2014/0243411 A1 | 8/2014 | Jay et al. |

FOREIGN PATENT DOCUMENTS

| | | |
|---|---|---|
| EP | 0 953 360 A1 | 11/1999 |
| WO | WO 2007/142804 A2 | 12/2007 |
| WO | WO 2013/109323 A2 | 7/2013 |

OTHER PUBLICATIONS

Guilmette, et. al. Journal of Pharmaceutical Sciences (1979), 68(2), 194-6.*
Caira, Mino R. "Crystalline Polymorphism of Organic Compounds" *Topics in Current Chemistry* 198:163-208 (1998).
Chan et al. "Investigation of Wetting Behavior of Nonaqueous Ethylcellulose Gel Matrices Using Dynamic Contact Angle" *Pharmaceutical Research* 23(2):408-421 (2006).
Department of Health and Human Services "Diethylenetriamene pentaacetate (DTPA)" *CDC Fact Sheet* 3 pages (Oct. 11, 2006).
Geraldes et al. "Complexes of $Ga^{3+}$ and $In^{3+}$ with the $N,N'$—Bis(butylamide) Derivative of Diethylenetriaminepentaacetic Acid: Stability Constants and Nuclear Magnetic Resonance Studies in Aqueous Solution" *Journal of the Chemical Society—Dalton Transactions* 327-335 (1995).
Guilmette et al. "Synthesis and Therapeutic Testing of Mono- and Dialkyl Esters of Pentetic (Diethylenetriaminepentaacetic) Acid for Decorporation of Polymeric Plutonium" *Journal of Pharmaceutical Sciences* 68(2):194-196 (1979).
Heng et al. "Development of Novel Nonaqueous Ethylcellulose Gel Matrices: Rheological and Mechanical Characterization" *Pharmaceutical Research* 22(4):676-684 (2005).
International Preliminary Report on Patentability corresponding to International Patent Application No. PCT/US2012/060985; mailed Apr. 22, 2014.
International Search Report and the Written Opinion of the International Searching Authority corresponding to International Patent Application No. PCT/US2012/060985; mailed Aug. 8, 2013.
International Search Report and the Written Opinion of the International Searching Authority corresponding to International Patent Application No. PCT/US2013/071738; mailed Apr. 17, 2014.
Prudencio et al. "A Caged Lanthanide Complex as a Paramagnetic Shift Agent for Protein NMR" *Chemistry, A European Journal* 10:3252-3260 (2004).
Radiation Event Medical Management, "Ca-DTPA/Zn-DTPA (Diethylentriamene pentaacetate)" www.remm.nlm.gov/dtpa.htm 3 pages (Sep. 26, 2014).
Rizkalla et al. "Thermodynamics, PMR, and Fluorescence Studies for the Complexation of Trivalent Lanthanides, $Ca^{2+}$, $Cu^{2+}$, and $Zn^{2+}$ by Diethylenetriaminepentaacetic Acid Bis(methylamide)" *Inorganic Chemistry* 32:582-586 (1993).
U.S. Food and Drug Administration, *FDA News*, "FDA Approves Drugs to Treat Internal Contamination from Radioactive Elements", Aug. 11, 2004, http://www.fda.gov/Drugs/EmergencyPreparedness/BioterrorismandDrugPreparedness/ucm130312.htm.

(Continued)

*Primary Examiner* — Jeffrey H Murray

(74) *Attorney, Agent, or Firm* — Myers Bigel, P.A.

(57) ABSTRACT

The present invention relates to trisodium diethylenetriamine pentaacetic acid (DTPA) prodrugs, such as, for example, DTPA di-ethyl esters. The invention further relates to compositions comprising DTPA prodrugs and methods of using the same.

10 Claims, 37 Drawing Sheets

(56) References Cited

OTHER PUBLICATIONS

Zhang et al., "Species-Dependent Metabolism of a DTPA Prodrug by Skin Esterases", *The University of North Carolina*, Aug. 4, 2011.
Zhang et al., "Transdermal Delivery of DTPA Prodrug for Continuous Decorporation of Transuranic Elements", *The University of North Carolina*, Aug. 4, 2011.
Extended European Search Report corresponding to European Patent Application No. 13856781.3 (10 pages) (dated Jun. 14, 2016).
Kamboj et al. "A simple and sensitive spectrophotometric method for estimation of diethylene triamine penta acetic acid (DTPA) in topical gel formulations" *Der Pharmacia Lettre* 3(3):23-28 (2011).
Prausnltz et al. "Transdermal drug delivery" *Nature Biotechnology* 26(11): 1261-1268 (2008).
Rautio et al, "Prodrugs: design and clinical applications" *Nature Reviews Drug Discover* 7:255-270 (2008).
Sinha et al. "Permeation Enhancers for Transdermai Drug Delivery" *Drug Development and Industrial Pharmacy* 26(11):1131-1140 (2000).
Xu et al. "Bisphospnonate-containing supramolecular hydrogels for topical decorporation of uranium-contaminated wounds in mice" *International Journal of Radiation Biology* 84(5):353-362 (2008).

\* cited by examiner

DTPA PRODRUGS, COMPOSITIONS THEREOF, AND METHODS OF USING THE SAME

RELATED APPLICATION DATA

This application is a continuation-in-part of International Application No. PCT/US2013/071738 filed on Nov. 25, 2013, which claims the benefit of and priority from U.S. Provisional Patent Application Ser. No. 61/729,780, filed Nov. 26, 2012, the disclosures of each of which are incorporated herein by reference in their entirety.

STATEMENT OF FEDERAL SUPPORT

This invention was made with government support under Grant No. HHSN272201000030C awarded by the National Institutes of Health. The government has certain rights in the invention.

FIELD OF THE INVENTION

The present invention relates to trisodium diethylenetriamine pentaacetic acid (DTPA) prodrugs. The present invention further relates to compositions comprising DTPA prodrugs and methods of using the same.

BACKGROUND OF THE INVENTION

The presence of metals, such as radioactive and/or non-radioactive metals, in an animal can be toxic to the body and/or cause negative health effects. Thus, removing such metals can be important to avoid or reduce toxicity to the animal.

Exposure to toxic metals can occur through environmental exposures. For example, an animal undergoing various medical procedures may be exposed to toxic metals. In addition, the United States and many other countries face increasing threats from terrorist groups with respect to the use of weapons of mass destruction against civilian populations. Of particular concern is that some of these groups are intensifying their efforts to acquire and develop nuclear and radiological weapons, and there are a limited number of therapies that can be offered to victims of nuclear terrorism.

Currently, the only agents that have been approved by the U.S. Food and Drug Administration (FDA) as chelating agents for americium, curium and plutonium are the calcium and zinc salts of trisodium diethylenetriamine pentaacetic acid (DTPA). Transuranic radionuclides (i.e., those with an atomic number of 92 or greater), such as americium, curium and plutonium, can potentially be incorporated in radiation dispersal devices (RDDs; "dirty bombs"). The primary goal in treating those exposed to transuranic radionuclides is to chelate the transuranic radionuclides before they become fixed in tissues, such as the liver and bone, and enhance their elimination from contaminated individuals.

SUMMARY OF THE INVENTION

A first aspect of the invention is a polymorph of 6,9-bis(carboxymethyl)-3-(2-ethoxy-2-oxoethyl)-11-oxo-12-oxa-3,6,9-triazatetradecan-1-oic acid characterized by a powder x-ray diffraction pattern substantially the same as that shown in FIG. 6A and/or a powder x-ray diffraction pattern having peaks at about 7.6, 12.4, 13.5, 14.0, 15.3, 18.1, 18.7, 18.8, 21.0, 22.5, 23.4, 24.5, 28.7, and 35.7±0.2 degrees 2 theta.

A further aspect of the invention is a process of preparing a polymorph of 6,9-bis(carboxymethyl)-3-(2-ethoxy-2-oxoethyl)-11-oxo-12-oxa-3,6,9-triazatetradecan-1-oic acid, comprising
(a) combining DTPA bis-anhydride, ethanol, and pyridine to form a reaction mixture;
(b) stirring the reaction mixture under nitrogen for about 24 hours;
(c) adding the reaction mixture to dichloromethane to form a dichloromethane solution;
(d) cooling the dichloromethane solution to a temperature of about −20° C. to form a precipitate of a polymorph of 6,9-bis(carboxymethyl)-3-(2-ethoxy-2-oxoethyl)-11-oxo-12-oxa-3,6,9-triazatetradecan-1-oic acid;
(e) filtering the dichloromethane solution to obtain the precipitate;
(f) optionally washing the precipitate with dichloromethane during the filtering step; and
(g) optionally drying the precipitate, thereby obtaining the polymorph.

Another aspect of the invention is a polymorph of 6,9-bis(carboxymethyl)-3-(2-ethoxy-2-oxoethyl)-11-oxo-12-oxa-3,6,9-triazatetradecan-1-oic acid characterized by a powder x-ray diffraction pattern substantially the same as that shown in FIG. 6D and/or a powder x-ray diffraction pattern having peaks at about 8.1, 12.0, 13.8, 15.4, 16.0, 16.6, 18.3, 19.3, 21.4, 22.1, 24.0, 26.5, and 29.2±0.2 degrees 2 theta.

Another aspect of the invention is a process of preparing a polymorph of 6,9-bis(carboxymethyl)-3-(2-ethoxy-2-oxoethyl)-11-oxo-12-oxa-3,6,9-triazatetradecan-1-oic acid, comprising
(a) combining DTPA bis-anhydride and absolute ethanol to form a reaction mixture;
(b) heating the reaction mixture to reflux while stirring for about 1.5 hours;
(c) filtering the reaction mixture to form a filtrate;
(d) cooling the filtrate to a temperature below about 20° C. to form a precipitate of a polymorph of 6,9-bis(carboxymethyl)-3-(2-ethoxy-2-oxoethyl)-11-oxo-12-oxa-3,6,9-triazatetradecan-1-oic acid;
(e) filtering the filtrate to obtain the precipitate;
(f) optionally washing the precipitate with cold ethanol;
(g) optionally washing the precipitate with methyl tert-butyl ether to form a filter cake;
(h) optionally mixing the filter cake with ethanol to form a second slurry;
(i) optionally heating the second slurry to a temperature of about 70° C.;
(j) optionally filtering the second slurry to form a second filtrate;
(k) optionally cooling the second filtrate to a temperature below about 20° C. to form a second precipitate;
(l) optionally filtering the second filtrate to obtain the second precipitate; and
(m) optionally drying the precipitate, thereby obtaining the polymorph.

A further aspect of the invention is a method of treating a subject to remove a radioactive element and/or a non-radioactive element from the subject comprising: administering a therapeutically effective amount of a DTPA prodrug of the present invention to a subject. In some embodiments, the DTPA prodrug is a DTPA di-ethyl ester of the present invention, such as, but not limited to, a DTPA di-ethyl ester polymorph of the present invention.

A further aspect of the invention is a method of increasing the amount of a radioactive element and/or a non-radioactive element removed from a subject comprising: administering a therapeutically effective amount of a DTPA prodrug of the present invention to a subject. In some embodiments, the DTPA prodrug is a DTPA di-ethyl ester of the present invention, such as, but not limited to, a DTPA di-ethyl ester polymorph of the present invention.

These and other aspects of the invention are set forth in more detail in the description of the invention below.

Figure 1:
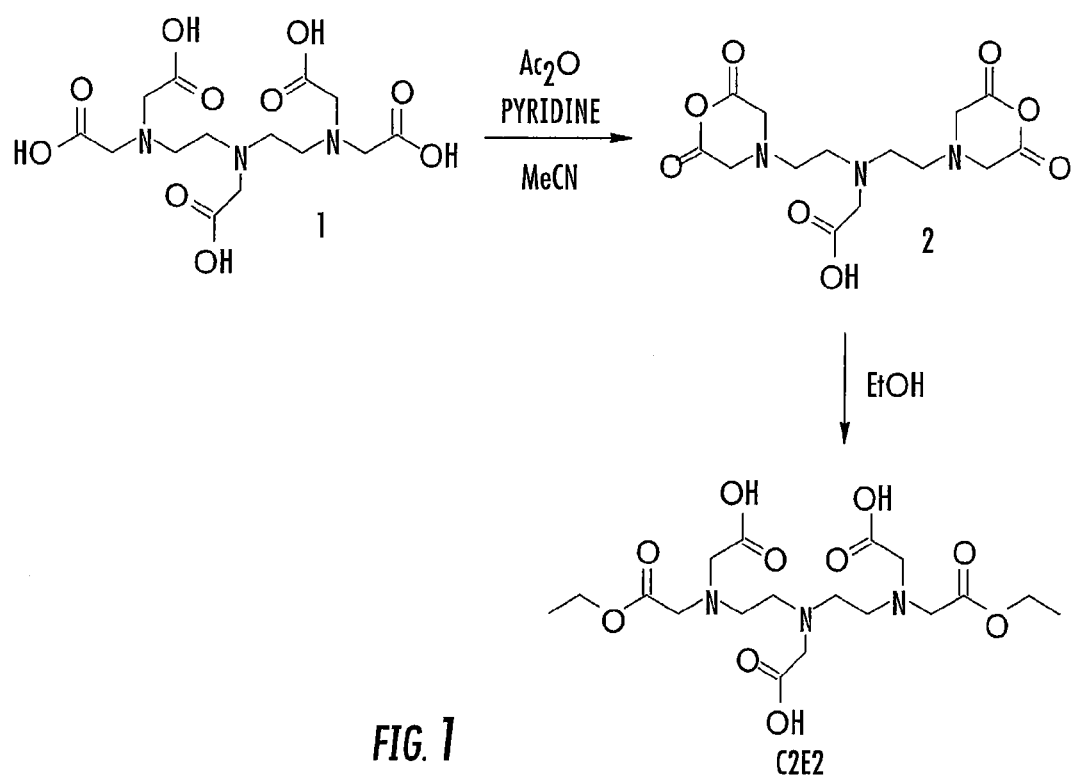
FIG. 1 shows a synthetic scheme for C2E2.

FIG. 8 shows an overlay of the XRD patterns for C) Lot 005-2 and D) Lot 050.

FIG. 9 shows the scanning electron micrographs of C2E2 preparations. Left: C2E2 MTD Lot; right: C2E2 Lot 050.

FIG. 10 shows the chromatogram of C2E2 of Lot 050.

FIG. 11 shows the chromatogram of C2E2 crystals produced from water.

FIG. 12 shows the chromatogram of C2E2 solid material from 1 hour heating in ethanol.

FIG. 13 shows the chromatogram of C2E2 filtrate from 1 hour heating in ethanol.

FIG. 14 shows the cumulative transport of C2E2 from the apical to basolateral compartment over two hours. Error bars represent the 95% confidence interval.

FIG. 15 shows the change in flux at increasing concentrations of C2E2. Error bars represent the 95% confidence interval.

FIG. 16 shows the change in apparent permeation coefficient with increasing concentration of C2E2. Error bars represent the 95% confidence interval.

FIG. 17 shows the daily $^{241}$Am clearance in male Sprague Dawley rats.

FIG. 18 shows the daily $^{241}$Am clearance in female Sprague Dawley rats.

FIG. 19 shows the total decorporation C2E2 dose response curve showing total $^{241}$Am decorporation in male and female Sprague Dawley rats seven days after contamination.

FIG. 20 shows the liver burden C2E2 dose response curve showing $^{241}$Am liver burden in male and female Sprague Dawley rats seven days after contamination.

FIG. 21 shows the skeletal burden C2E2 dose response curve showing $^{241}$Am liver burden in male and female Sprague Dawley rats seven days after contamination.

FIG. 22 shows the wound site burden C2E2 dose response curve showing $^{241}$Am content at the wound site in male and female Sprague Dawley rats.

FIG. 23A shows the average percent of recovered activity of $^{241}$Am in urine per day in dogs after administration of $^{241}$Am by inhalation exposure.

FIG. 23B shows the average percent of recovered activity of $^{241}$Am in feces per day in dogs after administration of $^{241}$Am by inhalation exposure.

FIG. 24A shows the average percentage of recovered activity of $^{241}$Am for cumulative urinary excretion of dogs administered different doses of C2E2 at 24 h after $^{241}$Am inhalation exposure.

FIG. 24B shows the average percentage of recovered activity of $^{241}$Am for cumulative fecal excretion of dogs administered different doses of C2E2 at 24 h after $^{241}$Am inhalation exposure.

FIGS. 25A-D show the average percentage of recovered activity of $^{241}$Am in A) liver, B) spleen, C) kidney, and D) lung of dogs administered different doses of C2E2 at 24 h after $^{241}$Am inhalation exposure.

FIGS. 26A-F show the average percentage of recovered activity of $^{241}$Am in A) ovaries, B) testes, C) GIT, D) TBLN, E) soft tissue, and F) total bone content in dogs administered different doses of C2E2 at 24 h after $^{241}$Am inhalation exposure.

FIG. 27 shows the relative concentration of C2E2 over time in samples prepared at 60, 70 and 100 mg/mL.

FIGS. 28A-C show the stability of C2E2 in A) rat, B) dog, and C) human plasma with each column in the graph representing (from left to right) normal plasma; heat inactivated plasma; a control substrate, diltiazem, in normal plasma; and the control substrate, diltiazem, in heat inactivated plasma over time.

FIG. 29 shows the americium burden in liver, skeletal, and injection site tissue seven days after contamination with each column in the graph representing (from left to right) control, C2E2 once daily (OD), C2E2 twice daily (BD), and DTPA.

FIGS. 30A and 30B show the percentage of initial americium injection eliminated in the urine per hour with A) showing the profile over the duration of the whole study and B) showing the expanded view starting 24 hours after americium contamination as the first C2E2 doses were administered. The percent decorporation per hour at time zero reflects the average hourly decorporation over the first 24 hours of the study. ♦ is the untreated control group, ■ is the C2E2 600 mg/kg OD group, ▲ is the C2E2 300 mg/kg BD group.

FIG. 31 shows a titration curve for C2E2 with 1 N potassium hydroxide.

FIG. 32 shows a titration curve for C2E2 (solid line) and C2E2-Gd (dotted line) with 0.1 N hydrochloric acid.

DETAILED DESCRIPTION

The present invention will now be described more fully hereinafter. This invention may be embodied in different forms and should not be construed as limited to the embodiments set forth herein. Rather, these embodiments are provided so that this disclosure will be thorough and complete, and will fully convey the scope of the invention to those skilled in the art.

The terminology used in the description herein is for the purpose of describing particular embodiments only and is not intended to be limiting of the invention. As used in the description and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description herein is for the purpose of describing particular embodiments only and is not intended to be limiting of the invention.

All patents, patent applications and publications referred to herein are incorporated by reference in their entirety for the teachings relevant to the sentence and/or paragraph in which the reference is presented. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the embodiments of the invention described herein may be used in any combination. For example, features described in relation to one embodiment may also be applicable to and combinable with other embodiments and aspects of the invention.

Moreover, the embodiments of the present invention also contemplate that in some embodiments, any feature or combination of features set forth herein may be excluded or omitted. To illustrate, if the specification states that a complex comprises components A, B and C, in some embodiments, any of A, B or C, or a combination thereof, may be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value, such as, for example, an amount or concentration, is meant to encompass variations of ±20%, ±10%, ±5%, ±1%, ±0.5%, or even ±0.1% of the specified amount. A range provided herein for a measureable value may include any other range and/or individual value therein.

"Substituted" as used herein to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group. The substituted group may contain one or more substituents that may be the same or different.

"Substituent" as used herein references a group that replaces another group in a chemical structure. Typical substituents include nonhydrogen atoms (e.g., halogens), functional groups (such as, but not limited to, amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include, but are not limited to, alkyl, lower alkyl, halo, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silylalkyl, silyloxy, boronyl, and modified lower alkyl.

"Alkyl" as used herein alone or as part of another group, refers to a straight or branched chain hydrocarbon containing from 1 to 30 carbon atoms. In some embodiments, the alkyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups such as, but not limited to, polyalkylene oxides (such as PEG), halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where m=0, 1, 2 or 3.

"Alkenyl" as used herein alone or as part of another group, refers to a straight or branched chain hydrocarbon containing from 1 to 30 carbon atoms (or in loweralkenyl 1 to 4 carbon atoms) which include 1 to 10 double bonds in the hydrocarbon chain. In some embodiments, the alkenyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkenyl include, but are not limited to, methylene (=CH$_2$), vinyl (—CH=CH$_2$), allyl (—CH$_2$CH=CH$_2$), 2-butenyl, 3-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups such as those described in connection with alkyl and loweralkyl above.

"Alkynyl" as used herein alone or as part of another group, refers to a straight or branched chain hydrocarbon containing from 1 to 30 carbon atoms (or in loweralkynyl 1 to 4 carbon atoms) which include at least one triple bond in the hydrocarbon chain. In some embodiments, the alkynyl group may contain 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Aryl" as used herein alone or as part of another group, refers to a monocyclic carbocyclic ring system or a bicyclic carbocyclic fused ring system or higher having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino acid derivative" as used herein, refers to an amino acid substituted with one or more substituents. Exemplary substituents include, but are not limited to, alkyl, lower alkyl, halo, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silylalkyl, silyloxy, boronyl, and modified lower alkyl. Exemplary amino acid derivatives include, but are not limited to, alanine methyl ester, alanine ethyl ester, alanine tert-butyl ester, valine methyl ester, valine ethyl ester, valine tert-butyl ester, phenylalanine methyl ester phenylalanine ethyl ester, phenylalanine tert-butyl ester, phenylalainamide, N-acetyl-phenylalanine, N-ethoxycarbonyl-phenylalanine, tyrosine methyl ester, tyrosine ethyl ester, tyrosine tert-butyl ester, N-acetyl-tyrosine, and O-benzyl-tyrosine.

Described herein are DTPA prodrugs of Formula (I)

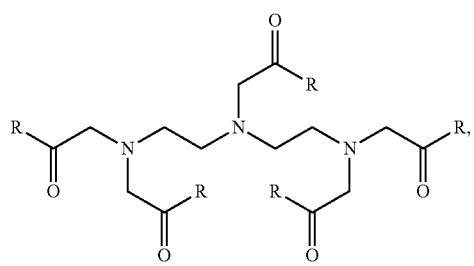

(I)

wherein:

R is —OR$^1$ or —NHR$^1$; and

R$^1$ is each independently selected from the group consisting of H, C$_1$-C$_{30}$ alkyl, C$_2$-C$_{30}$ alkenyl, C$_2$-C$_{30}$ alkynyl, benzyl, cycloalkyl, aryl, arylalkyl, arylalkenyl, arylalkynyl, heterocyclic, and amino acid derivative and wherein when R is —OR$^1$ at least one R$^1$ is not hydrogen.

In particular embodiments of the present invention, R is —OR$^1$ and R$^1$ is C$_1$-C$_{30}$ alkyl, e.g., C$_1$-C$_{12}$ and/or C$_1$-C$_6$. In certain embodiments of the present invention, the DTPA prodrug of Formula (I) is penta-substituted. When one or more R$^1$ is present, then R$^1$ at each occurrence may be the same as another R$^1$ and/or different than another R$^1$. Thus, all R$^1$ may be the same, all R$^1$ may be different, or some R$^1$ may be the same and some R$^1$ may be different. A DTPA prodrug of Formula (I) (i.e., a DTPA prodrug of the present invention) does not include trisodium diethylenetriamine pentaacetic acid (DTPA). Exemplary DTPA prodrugs of Formula (I) and their synthesis can be found in U.S. Pat. No. 8,030,358, which is incorporated herein by reference in its entirety. In some embodiments of the present invention, a DTPA prodrug of the present invention is a DTPA di-ethyl ester. In some embodiments of the present invention, a DTPA prodrug of the present invention has one of the following structures:

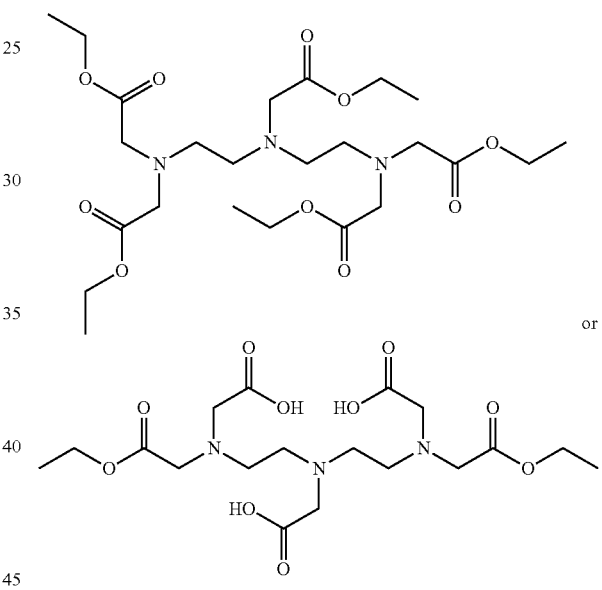

In particular embodiments of the present invention, a DTPA prodrug of Formula (I) has certain physical-chemical properties. For example, the DTPA prodrug of Formula (I) may have a molecular weight from about 400 to about 700 or any range and/or individual value therein, such as from about 400 to about 600 or from about 400 to about 500. In some embodiments of the present invention, the DTPA prodrug of Formula (I) may have an apparent solubility of about 100 mg/mL to about 200 mg/mL in an aqueous solution at a pH in a range of about 2 to about 3. In some embodiments of the present invention, the DTPA prodrug of Formula (I) may have an apparent solubility of about 150 mg/mL in an aqueous solution at a pH in a range of about 2 to about 3. Thus, the DTPA prodrug of Formula (I) may have a log P value of about −3.5 to about −1.5 at a pH of about 3.0, and in some embodiments a log P value of about −2.9 to about −2.1 at a pH of about 3.0.

In some embodiments, a DTPA prodrug of the present invention has a bioavailability of greater than 5%. In some embodiments, a DTPA prodrug of the present invention has a bioavailability of greater than 5% upon administration to a subject, such as, for example, when orally administered to a subject. In some embodiments of the present invention, a DTPA prodrug may be administered to a subject and may be resistant to hydrolysis prior to absorption in the gastrointestinal (GI) tract of the subject. In some embodiments of the present invention, the DTPA prodrug may have an apparent solubility of about 100 mg/mL to about 200 mg/mL in an aqueous solution at a pH in a range of about 2 to about 3 and may dissolve rapidly during transit through the GI tract of a subject. In some embodiments of the present invention, the dissolution of the DTPA prodrug in the GI tract of a subject may allow for absorption of the DTPA prodrug to occur.

In some embodiments, the present invention provides a polymorph of a DTPA di-ethyl ester having the chemical name 6,9-bis(carboxymethyl)-3-(2-ethoxy-2-oxoethyl)-11-oxo-12-oxa-3,6,9-triazatetradecan-1-oic acid (also referred to herein as C2E2) and having the following structure:

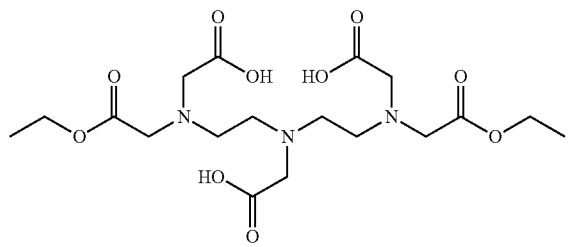 [SMILES: CCOC(=O)CN(CCN(CCN(CC(=O)O)CC(=O)OCC)CC(=O)O)CC(=O)O]

In some embodiments of the present invention, a polymorph of a DTPA di-ethyl ester of the present invention may be more stable than other known forms of C2E2. Stability can be measured by methods known to those of skill in the art. For example, in some embodiments, stability is determined by comparing the melting points of C2E2 polymorphs. In some embodiments of the present invention, a C2E2 polymorph of the present invention is more stable compared to other C2E2 polymorphs since the C2E2 polymorph of the present invention has a higher melting point than the melting points of the other C2E2 polymorphs. Stability may refer to the stability of a polymorph of the present invention during storage and/or in a solution, such as an aqueous solution.

In certain embodiments of the present invention, a polymorph of a DTPA di-ethyl ester of the present invention may be easier to formulate and/or prepare compared to other known forms of C2E2. For example, a polymorph of a DTPA di-ethyl ester of the present invention may have an improved solubility compared to other known forms of C2E2. In some embodiments of the present invention, a polymorph of a DTPA di-ethyl ester of the present invention may provide a better bioavailability after delivery to a subject compared to other known forms of C2E2 when administered in the same manner.

In certain embodiments of the present invention, a DTPA prodrug of the present invention may be de-esterified to form DTPA and/or a metabolite of C2E2, such as, but not limited to, a DTPA mono-ethyl ester (e.g., C2E1). In some embodiments of the present invention, a DTPA di-ethyl ester of the present invention may be a DTPA prodrug that may be de-esterified by an esterase to form DTPA and/or a metabolite of C2E2. Alternatively or in addition, in certain embodiments of the present invention, a DTPA di-ethyl ester of the present invention may be a chelating agent, such as, but not limited to, a chelating agent for radioactive elements and/or non-radioactive elements.

Figure 6A:
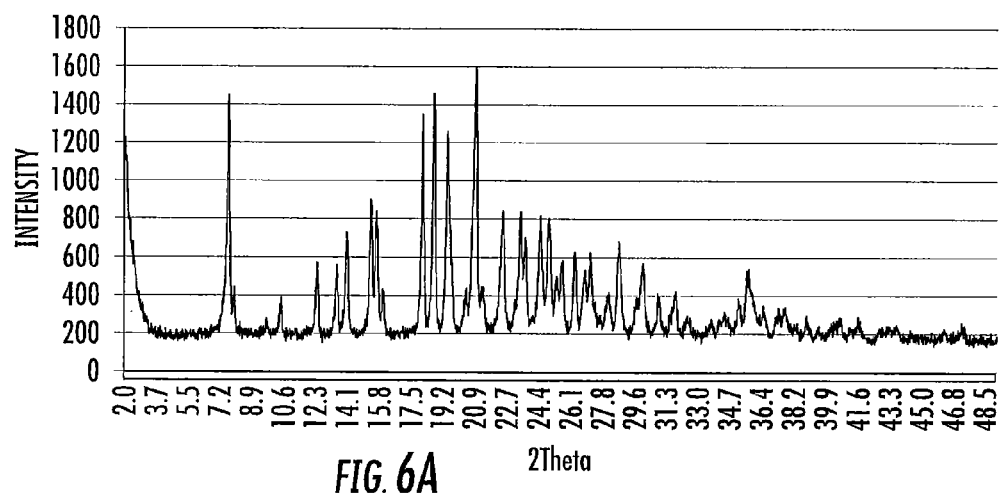
FIGS. 6A-6E show X-ray diffraction (XRD) patterns for C2E2 preparations: A) Reference standard; B) MTD Lot; C) Lot 005-2; D) Lot 050; and E) a comparison of XRD patterns A-D.
Figure 6B:
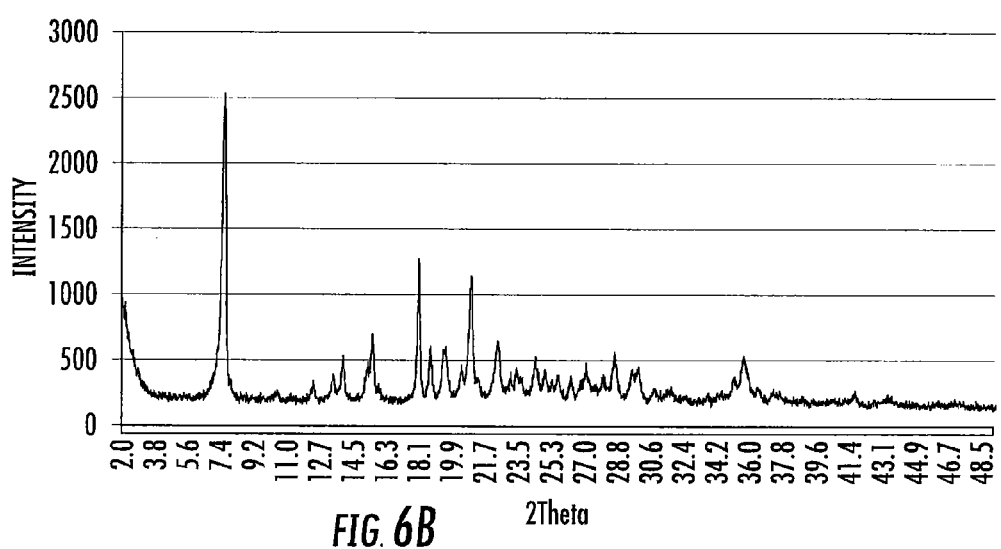
Figure 6C:
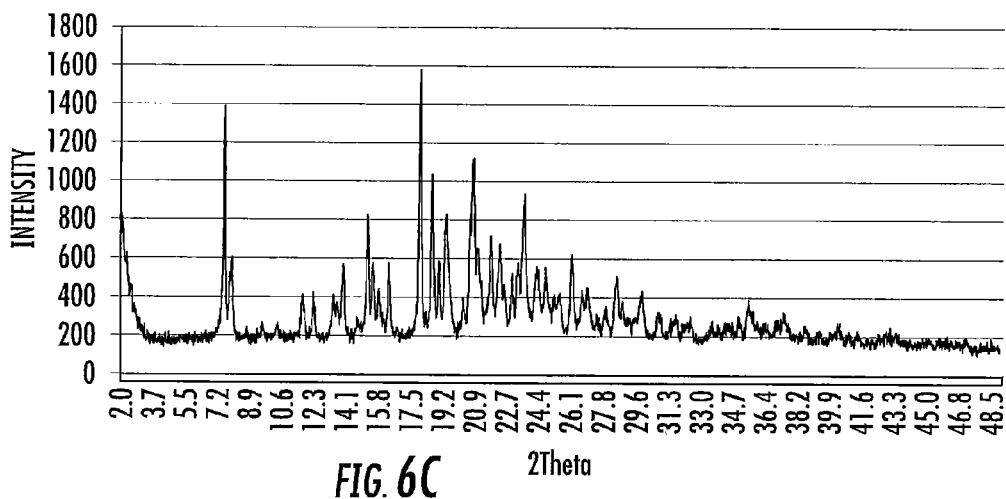
Figure 6D:
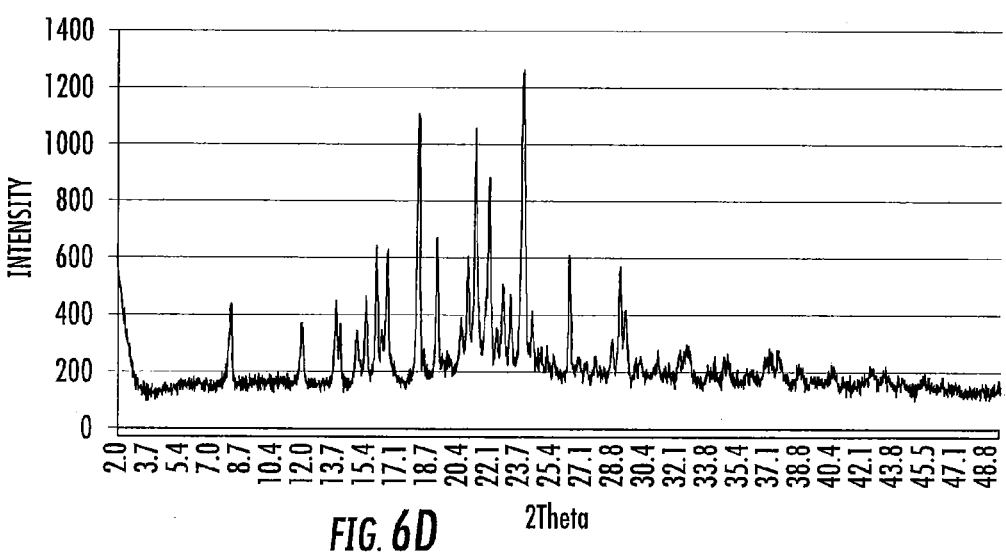
Figure 6E:
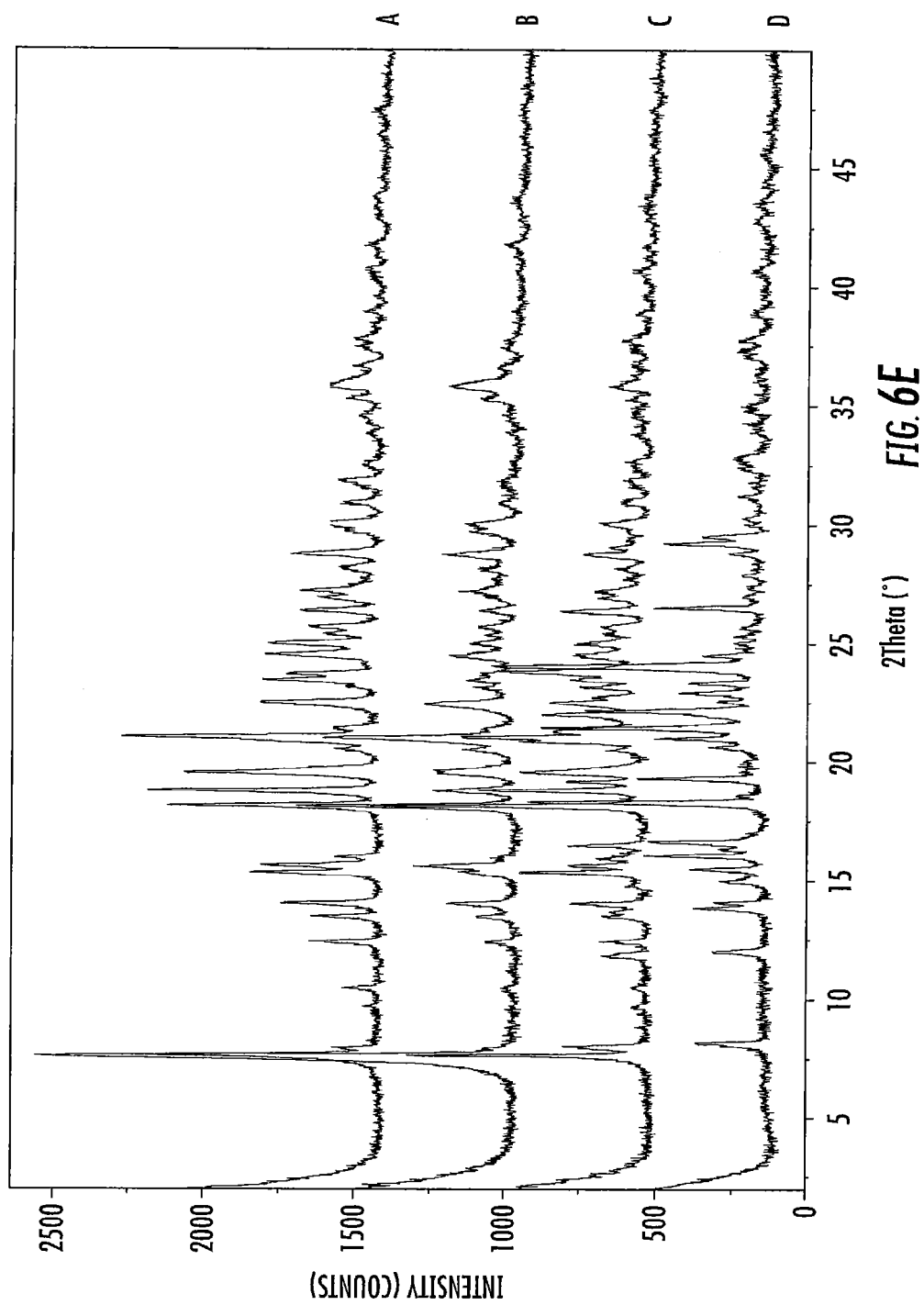
Figure 7:
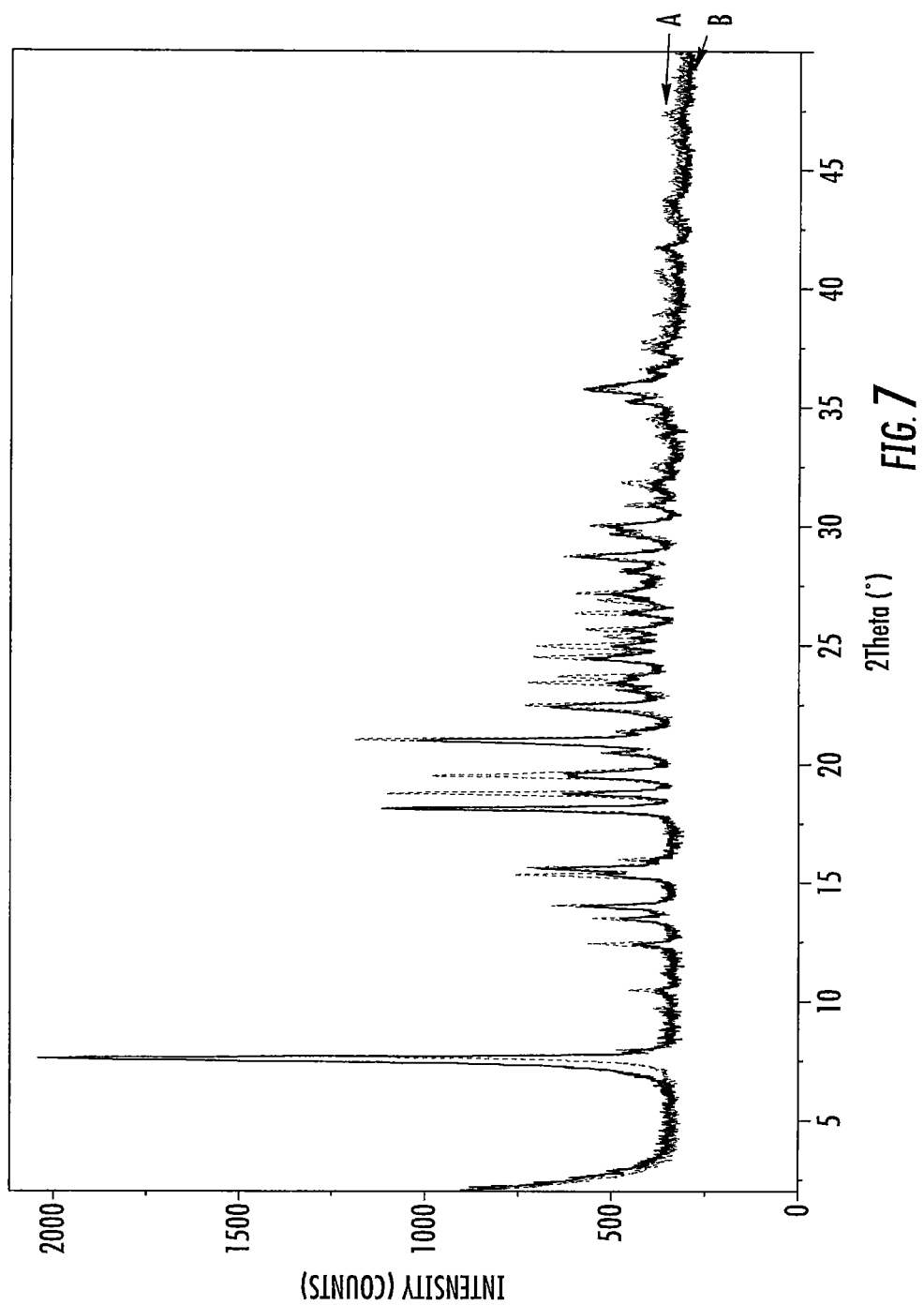
FIG. 7 shows an overlay of the XRD patterns for A) reference standard and B) MTD Lot.
Figure 8:
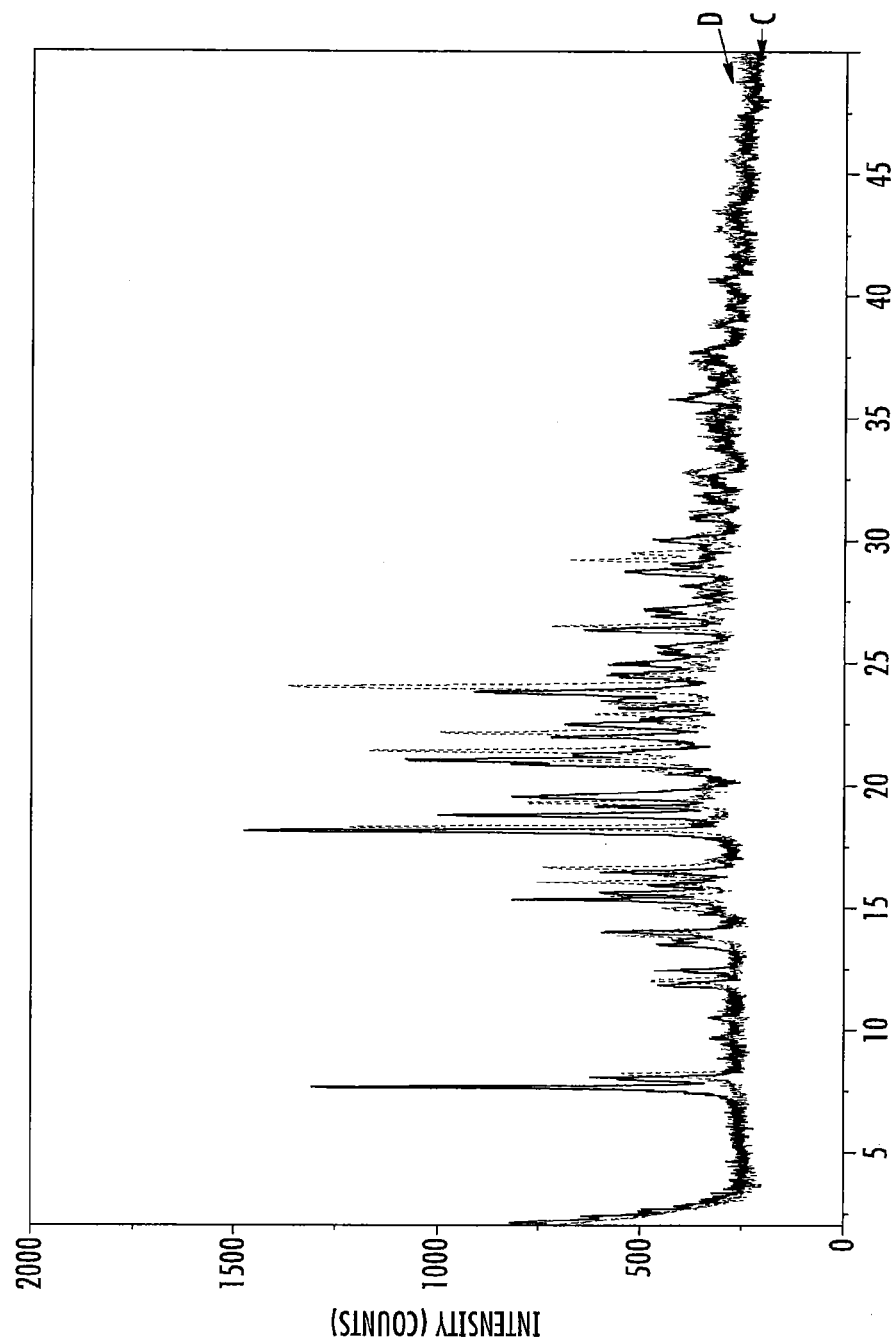

According to some embodiments of the present invention, a polymorph of a DTPA di-ethyl ester of the present invention may have a powder x-ray diffraction pattern corresponding to (e.g., substantially the same as, the same as, etc.) a powder x-ray diffraction pattern shown in any of FIGS. 6-8. In particular embodiments of the present invention, a polymorph of a DTPA di-ethyl ester of the present invention has a powder x-ray diffraction pattern corresponding to the powder x-ray diffraction pattern in FIGS. 6 A, B, C, and/or D.

In certain embodiments of the present invention, a polymorph of a DTPA di-ethyl ester of the present invention has a powder x-ray diffraction pattern corresponding to the powder x-ray diffraction pattern in FIG. 6A. The polymorph having a powder x-ray diffraction pattern corresponding to FIG. 6A is referred to herein as Form I. A DTPA di-ethyl ester of Form I may be characterized by a powder x-ray diffraction pattern having peaks at about 7.6, 12.4, 13.5, 14.0, 15.3, 18.1, 18.7, 18.8, 21.0, 22.5, 23.4, 24.5, 28.7, and 35.7±0.2 degrees 2 theta.

A DTPA di-ethyl ester of Form I is characterized by a melting point from about 109° C. to about 122° C., or any range and/or individual value therein, as measured using differential scanning calorimetry over a range of about 25° C. to about 320° C. with a heating rate of about 10.00° C./min. The rate, for example, may be between 8.00° C./min and 12.00° C./min or any other range and/or individual value therein. In some embodiments of the present invention, a DTPA di-ethyl ester of Form I may have a melting point of about 109° C., 110° C., 111° C., 112° C., 113° C., 114° C., 115° C., 116° C., 117° C., 118° C., 119° C., 120° C., 121° C., or 122° C., or any range therein. In certain embodiments of the present invention, a DTPA di-ethyl ester of Form I may have a melting point at about 111.8° C., 116.3° C., or 119.4° C.

DTPA di-ethyl ester of Form I may be obtained by precipitating DTPA di-ethyl ester in dichloromethane. In some embodiments, a DTPA di-ethyl ester of Form I is obtained by precipitating DTPA di-ethyl ester in dichloromethane while cooling at a temperature of about −20° C. The temperature, for example, may be between −16° C. and −24° C. or any other range and/or individual value therein.

According to some embodiments of the present invention, provided is a method of preparing a DTPA di-ethyl ester of Form I, the method comprising combining DTPA bis-anhydride, ethanol and pyridine to form a reaction mixture, stirring the reaction mixture under nitrogen or other inert gas(es) for, for example, about 24 hours, such as, for example, between 20 hours and 28 hours or any other range and/or individual value therein, adding the reaction mixture to dichloromethane to form a dichloromethane solution, cooling the dichloromethane solution to a temperature of about −20° C., such as, for example, between −16° C. and −24° C. or any other range and/or individual value therein, to form a precipitate of a polymorph of a DTPA di-ethyl ester of the present invention, filtering the dichloromethane solution to obtain the precipitate, optionally washing the precipitate with dichloromethane during the filtering step, and optionally drying the precipitate, thereby obtaining a DTPA di-ethyl ester of Form I.

In some embodiments of the present invention, a DTPA di-ethyl ester of Form I may be obtained during and/or after the cooling step in a method of preparing a DTPA di-ethyl ester of Form I of the present invention. In certain embodiments of the present invention, a method of preparing a DTPA di-ethyl ester of Form I of the present invention comprises washing the precipitate with dichloromethane during the filtering step and drying the precipitate, and a DTPA di-ethyl ester of Form I may be obtained during and/or after the drying step.

In other embodiments of the present invention, a polymorph of a DTPA di-ethyl ester of the present invention has a powder x-ray diffraction pattern corresponding to the powder x-ray diffraction pattern in FIG. 6D. The polymorph having a powder x-ray diffraction pattern corresponding to FIG. 6D is referred to herein as Form II. A DTPA di-ethyl ester of Form II may be characterized by a powder x-ray diffraction pattern having peaks at about 8.1, 12.0, 13.8, 15.4, 16.0, 16.6, 18.3, 19.3, 21.4, 22.1, 24.0, 26.5, and 29.2±0.2 degrees 2 theta.

A DTPA di-ethyl ester of Form II is characterized by a melting point from about 132° C. to about 143° C., or any range and/or individual value therein, as measured using differential scanning calorimetry over a range of about 25° C. to about 320° C. with a heating rate of about 10.00° C./min. The rate, for example, may be between 8.00° C./min and 12.00° C./min or any other range and/or individual value therein. In some embodiments of the present invention, a DTPA di-ethyl ester of Form II may have a melting point of about 132° C., 133° C., 134° C., 135° C., 136° C., 137° C., 138° C., 139° C., 140° C., 141° C., 142° C., or 143° C., or any range therein. In certain embodiments of the present invention, a DTPA di-ethyl ester of Form II may have a melting point at about 134.8° C., 136.4° C., 139.1° C., or 141.6° C.

DTPA di-ethyl ester of Form II may be obtained by precipitating DTPA di-ethyl ester in ethanol. In some embodiments, a DTPA di-ethyl ester of Form II is obtained by precipitating DTPA di-ethyl ester in ethanol while cooling to a temperature below about 20° C. The temperature, for example, may be between 16° C. and 24° C. or any other range and/or individual value therein.

According to some embodiments of the present invention, provided is a method of preparing a DTPA di-ethyl ester of Form II, the method comprising combining DTPA bis-anhydride and absolute ethanol to form a reaction mixture, heating the reaction mixture to reflux while stirring for, for example, about 1.5 hours, such as, for example, between 1.2 hours and 1.8 hours or any other range and/or individual value therein, filtering the reaction mixture to form a filtrate, cooling the filtrate to a temperature below about 20° C., such as, for example, between 16° C. and 24° C. or any other range and/or individual value therein, to form a precipitate of a polymorph of a DTPA di-ethyl ester of the present invention, filtering the filtrate to obtain the precipitate, and optionally drying the precipitate, thereby obtaining DTPA di-ethyl ester of Form II. In certain embodiments, following the filtering step and prior to the optional drying step, the method may further comprise one or more steps of washing the precipitate with cold ethanol and then methyl tert-butyl ether (MTBE) to form a filter cake, mixing the filter cake with ethanol to form a second slurry, heating the second slurry to a temperature of about 70° C., such as, for example, between 56° C. and 84° C. or any other range and/or individual value therein, filtering the second slurry to form a second filtrate, cooling the second filtrate to a temperature below about 20° C., such as, for example, between 16° C. and 24° C. or any other range and/or individual value therein, to form a second precipitate of a polymorph of a DTPA di-ethyl ester of the present invention, filtering the second filtrate to obtain the precipitate, and then optionally drying the precipitate, thereby obtaining DTPA di-ethyl ester of Form II.

In some embodiments of the present invention, a DTPA di-ethyl ester of Form II may be obtained during and/or after the first cooling step in a method of preparing a DTPA di-ethyl ester of Form II of the present invention. In certain embodiments of the present invention, a DTPA di-ethyl ester of Form II may be obtained during and/or after the second cooling step in a method of preparing a DTPA di-ethyl ester of Form II of the present invention. In some embodiments of the present invention, a method of preparing a DTPA di-ethyl ester of Form II of the present invention comprises drying the first and/or second precipitate, and a DTPA di-ethyl ester of Form II may be obtained during and/or after the drying step.

According to another aspect of the present invention, provided herein are pharmaceutical compositions comprising a DTPA prodrug of the present invention. In some embodiments, the DTPA prodrug is a DTPA di-ethyl ester of the present invention, such as, but not limited to, a polymorph of a DTPA di-ethyl ester of the present invention. In certain embodiments, a pharmaceutical composition of the present invention comprises a DTPA di-ethyl ester of Form I and/or Form II. One or more different DTPA prodrugs of the present invention may be present in a pharmaceutical composition of the present invention. The pharmaceutical composition may comprise at least about 50% or more of one DTPA prodrug (e.g., a DTPA di-ethyl ester of Form I or Form II) compared to the total amount of the one or more different DTPA prodrugs present in the composition, and, in some embodiments, at least about 55%, 60%, 65%, 70%, 75%, 80%, 85%, 90%, 95%, 98%, 99%, or more of one DTPA prodrug compared to the total amount of the one or more different DTPA prodrugs present in the composition. In some embodiments, a pharmaceutical composition of the present invention further comprises a pharmaceutically acceptable carrier. A pharmaceutically acceptable carrier is any carrier which is relatively non-toxic and innocuous to a subject at concentrations consistent with effective activity of a DTPA prodrug of the present invention so that any side effects ascribable to the carrier do not vitiate the beneficial effects of the DTPA prodrug.

A pharmaceutical composition of the present invention may be formulated to administer in a single dose and/or unit about 1 mg to about 2,000 mg of a DTPA prodrug of the present invention per kilogram of a subject's total body weight, or any range and/or individual value therein, such as, but not limited to about 10 mg to about 1,000 mg, about 1,000 mg to about 2,000 mg, about 200 mg to about 600 mg, about 1 mg to about 500 mg, about 5 mg to about 250 mg, about 5 mg to about 100 mg, about 15 mg to about 45 mg, or about 10 mg to about 40 mg per kilogram of a subject's total body weight. A DTPA prodrug of the present invention may be administered with a pharmaceutically acceptable carrier using any effective conventional dosage unit form, such as, but not limited to, immediate and timed release preparations, orally, parenterally, topically, or the like. Exemplary pharmaceutical compositions include, but are not limited to, those described in U.S. Pat. No. 8,030,358, International Application No. PCT/US12/60985, and U.S. Patent Application Publication No. 2014/0243411, the contents of each of which are incorporated herein by reference in their entirety for the contents related to formulations and drug delivery systems and methods of preparing such formulations and systems. In certain embodiments of the present invention, a pharmaceutical composition of the present invention is suitable for oral administration.

For oral administration, a DTPA prodrug of the present invention may be formulated into solid or liquid preparations such as, but not limited to, capsules, pills, tablets, troches, lozenges, chewing gum, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment of the present invention, a DTPA prodrug of the present invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They may provide a DTPA prodrug of the present invention in admixture with a dispersing or wetting agent, a suspending agent, and/or one or more preservatives. Suitable dispersing or wetting agents and suspending agents are exemplified by those already mentioned above. Additional excipients, for example, those sweetening, flavoring and coloring agents described above, may also be present.

A pharmaceutical composition of the present invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending a DTPA prodrug of the present invention in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

A DTPA prodrug of the present invention may also be administered parenterally, that is, subcutaneously, intravenously, intramuscularly, or interperitoneally, as injectable dosages of the DTPA prodrug in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which may be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

A parenteral composition of the present invention may contain from about 0.5% to about 90% or more by weight of a DTPA prodrug of the present invention in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

A pharmaceutical composition of the present invention may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A further aspect of the present invention provides a method of removing a radioactive element and/or non-radioactive element from a subject comprising administering a DTPA prodrug and/or composition of the present invention. "Radioactive element" as used herein, refers to a chemical element that emits particulate radiation such as, but not limited to, alpha particles, beta particles, Auger electrons, etc., or a chemical element that emits photons such as, but not limited to, x-rays, gamma rays, etc. The radioactive element may be present in its elemental form or as part of a chemical compound. The radioactive element can have an atomic number of 1 to 103. In certain embodiments of the present invention, the radioactive element is in the actinide series (i.e., has an atomic number of 89-103) of elements. In particular embodiments, the radioactive element is an isotope of plutonium (Pu), americium (Am), or curium (Cm). "Non-radioactive element" as used herein refers to a chemical element that is not a radioactive element and has an atomic number of 1 to 103. In certain embodiments, the non-radioactive element is a heavy metal and/or an element present in a subject at a dose detrimental and/or toxic to the subject. Exemplary non-radioactive elements include, but are not limited to, lead, mercury, plutonium, vanadium, tungsten, cadmium, arsenic, zinc, copper, manganese, selenium, chromium, molybdenum, aluminum, bismuth, gold, gallium, gadolinium, lithium, silver, cobalt, iron, nickel, selenium, thallium, and any combination thereof.

In some embodiments, the radioactive element and/or non-radioactive element is in ionic form and/or is bound and/or complexed to a chemical moiety. For example, in some embodiments, gadolinium ions, linear gadolinium-based contrast agents (GBCAs), and/or macrocyclic GBCAs may be removed from a subject by administering a DTPA prodrug of the present invention, such as, but not limited to, C2E2. A DTPA prodrug of the present invention and/or DTPA may bind and/or be complexed to a radioactive and/or non-radioactive element to facilitate its removal from the subject. In some embodiments, a DTPA prodrug of the present invention and/or DTPA may bind and/or be complexed to a radioactive and/or non-radioactive element in the bloodstream of a subject and/or in one or more tissues of a subject. In some embodiments, a DTPA prodrug of the present invention and/or DTPA may remove a radioactive and/or non-radioactive element through urinary and/or fecal excretion.

The term "administering", "administration", and grammatical variants thereof, as used herein, refer to any mode of delivery to a subject. A DTPA prodrug of the present invention may be administered to a subject by any suitable route, including, but not limited to, orally (inclusive of administration via the oral cavity), parenterally, by inhalation spray, topically, transdermally, rectally, nasally, sublingually, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In certain embodiments of the present invention, a DTPA prodrug and/or composition of the present invention is administered orally.

Another aspect of the present invention provides a method of treating a subject comprising administering a DTPA prodrug and/or composition of the present invention to the subject. The term "treating" and grammatical variants thereof, as used herein, refer to any type of treatment that imparts a benefit to a subject, including delaying and/or reducing the onset and/or progression of one or more symptom(s) and/or condition(s), reducing the severity of one or more symptom(s) and/or condition(s), etc. Those skilled in the art will appreciate that the benefit imparted by the treatment according to the methods of the present invention is not necessarily meant to imply cure (e.g., no detectable incorporation of a radioactive and/or non-radioactive element into a subject's tissue, such as, for example, bones, and/or organs) and/or abolition of the symptom(s) and/or condition(s). The symptoms and/or conditions may include those occurring after exposure of the subject to a radioactive and/or non-radioactive element.

In some embodiments of the present invention, a method of treating a subject exposed to a radioactive and/or non-radioactive element is provided comprising administering a DTPA prodrug and/or composition of the present invention. Thus, in some embodiments of the present invention, methods are provided for the removal of a radioactive and/or non-radioactive element from a subject exposed to the radioactive element and/or non-radioactive element. Those skilled in the art will appreciate that the removal of the radioactive and/or non-radioactive element from the subject may be partial or complete.

Another aspect of the present invention provides a method of preventing the incorporation of a radioactive and/or non-radioactive element in a subject comprising administering a DTPA prodrug and/or composition of the present invention to the subject. In some embodiments, a method of preventing the incorporation of a radioactive and/or non-radioactive element in a subject may comprise administering a DTPA prodrug and/or composition of the present invention to the subject prior to the subject's exposure to the radioactive and/or non-radioactive element.

The term "preventing" and grammatical variants thereof, as used herein, refer to any type of prevention that imparts a benefit to a subject, including avoiding, delaying, and/or reducing the onset and/or progression of one or more symptom(s) and/or condition(s), reducing the severity of the onset of one or more symptom(s) and/or condition(s), etc. Those skilled in the art will appreciate that the benefit imparted by the methods of the present invention is not necessarily meant to imply complete prevention (e.g., no detectable incorporation of a radioactive and/or non-radioactive element into a subject's tissue, such as, for example, bones, and/or organs) and/or abolition of the symptom(s) and/or condition(s). The symptoms and/or conditions may include those occurring after exposure of the subject to a radioactive and/or non-radioactive element. In some embodiments, a method of preventing the incorporation of a radioactive and/or non-radioactive element in a subject comprising administering a DTPA prodrug and/or composition of the present invention may prevent, reduce, and/or limit the amount of the radioactive and/or non-radioactive element that is incorporated in the subject's tissue. Preventing, reducing, and/or limiting the amount of a radioactive and/or non-radioactive element incorporated in the subject's tissue may be determined compared to an untreated subject.

In other embodiments of the present invention, a method of treating a subject prior to exposure to a radioactive and/or non-radioactive element is provided comprising administering a DTPA prodrug and/or composition of the present invention. In a further aspect of the present invention, a method of preventing or reducing the incorporation of a radioactive and/or non-radioactive element in a subject is provided comprising administering a DTPA prodrug and/or composition of the present invention.

"Expose", "exposure", and grammatical variants thereof, as used herein, refer to a subject who may come into contact (e.g., a known and/or perceived threat of exposure) and/or has come into contact and/or become contaminated with a radioactive and/or non-radioactive element (e.g., the subject has internalized and/or incorporated a radioactive and/or non-radioactive element). For example, in some embodiments, a subject will be exposed to, has been exposed to, and/or is suspected to be exposed to ionizing radiation (e.g., alpha particles and/or beta particles) from a radioactive element such that the subject's body may absorb about 100 mrem or more of radiation in one year or less. Thus, the subject may receive an absorbed radiation dose of about 100 mrem, 500 mrem, 1 rem, 5 rem, 10 rem, 30 rem, 50 rem, 100 rem, 250 rem, 500 rem, 1,000 rem or more in one year or less. In some embodiments of the present invention, a subject is contaminated with a radioactive element (e.g., the subject has internalized and/or incorporated a radioactive element). The exposure to the ionizing radiation may be chronic (e.g., occurring over a long duration of time such as month(s) and/or one year) and/or acute (e.g., occurring in a short duration of time such as minute(s), hour(s), and/or day(s)).

In some embodiments, a subject will be exposed to, has been exposed to, and/or is suspected to be exposed to a non-radioactive element e.g., a heavy metal, a rare earth metal, etc. A subject may be administered and/or in contact with a non-radioactive element. For example, in some embodiments, a subject may be administered a gadolinium-based contrast enhancement agent (GBCA), such as a linear and/or macrocyclic GBCA (e.g., before and/or while undergoing a Magnetic Resonance Imagining (MRI) procedure). In some embodiments of the present invention, a subject may be administered a DTPA prodrug of the present invention prior to exposure to a non-radioactive element, such as, but not limited to, gadolinium, and/or concurrently with and/or upon exposure to a non-radioactive element. In some embodiments of the present invention, a DTPA prodrug of the present invention is prophylactically administered to a subject.

Some embodiments include a method of treating a subject to remove a non-radioactive element, such as, but not limited to, gadolinium from a subject and/or a method of preventing the incorporation of a non-radioactive element, such as, but not limited to, gadolinium in a subject The method may comprise administering a DTPA prodrug and/or composition of the present invention to the subject. In some embodiments, a method of increasing the removal of the non-radioactive element, such as, but not limited to, gadolinium, from the subject may be provided. A method of the present invention may increase the removal of a non-radioactive element, such as, but not limited to, gadolinium, from a subject compared to an untreated subject. The administering step may be before, during, and/or after exposure to the non-radioactive element. For example, a DTPA prodrug and/or composition of the present invention may be administered to a subject before, during, and/or after the subject has received a GBCA. In some embodiments, a method of the present invention may treat and/or prevent nephrogenic systemic fibrosis (NSF).

The present invention finds use in both veterinary and medical applications. Suitable subjects of the present invention include, but are not limited to avians and mammals. The term "avian" as used herein includes, but is not limited to, chickens, ducks, geese, quail, turkeys, pheasants, ratites (e.g., ostrich), parrots, parakeets, macaws, cockatiels, canaries, finches, and birds in ovo. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), and mammals in utero. In some embodiments of the present invention the subject is a mammal and in certain embodiments the subject is a human. Human subjects include both males and females of all ages including fetal, neonatal, infant, juvenile, adolescent, adult, and geriatric subjects as well as pregnant subjects.

In particular embodiments of the present invention, the subject is "in need of" the methods of the present invention, e.g., the subject has been exposed to a radioactive and/or non-radioactive element, it is believed that the subject will be exposed to a radioactive and/or non-radioactive element, and/or it is believed that the subject has been exposed to a radioactive and/or non-radioactive element. A DTPA prodrug, composition, and/or method of the present invention may be particularly suitable for children at or younger than about 10 years of age, such as children at or younger than about 5 years of age or 1 year of age. The present invention may also be particularly suitable for geriatrics.

The administration step may be carried out prior to, during, and/or after exposure to a radioactive and/or non-radioactive element or a threat thereof. The administration step may be carried out to deliver one or more doses of a DTPA prodrug and/or composition of the present invention, such as 1, 2, 3, 4, 5, 6, 7, 8, or more doses of the DTPA prodrug and/or composition. Exemplary dosage regimens include, but are not limited to, once a day, twice a day, every other day, once a week, etc. for one or more day(s), week(s), month(s), and/or year(s). In certain embodiments of the present invention, the administering step is carried out to remove a radioactive and/or non-radioactive element from a subject. In some embodiments of the present invention, the administering step is carried out to prevent incorporation of a radioactive and/or non-radioactive element in a subject's tissue and/or organs and/or to reduce and/or limit the amount of a radioactive and/or non-radioactive element incorporated in a subject's tissue and/or organs. In some embodiments of the present invention, the administering step is carried out to deliver a therapeutically effective amount of C2E2. In particular embodiments of the present invention, the administering step is carried out to deliver a therapeutically effective amount and/or prophylactically effective amount of a DTPA di-ethyl ester of Form I and/or Form II to a subject.

As used herein, the term "therapeutically effective amount" refers to an amount of a DTPA prodrug of the present invention that elicits a therapeutically useful response in a subject. Those skilled in the art will appreciate that the therapeutic effects need not be complete or curative, as long as some benefit is provided to the subject. In particular embodiments of the present invention, a therapeutically effective amount of a DTPA prodrug of the present invention results in the detectable elimination or removal of a radioactive and/or non-radioactive element from a subject. Detection of the elimination or removal of a radioactive and/or non-radioactive element may be accomplished by measuring the amount of the radioactive and/or non-radioactive element in the urine, feces, other bodily fluids, and/or exhaled gas from the lungs of the subject. Methods and instruments used to quantify the amount of a radioactive and/or non-radioactive element removed from a subject are known to those skilled in the art and include, but are not limited to, quantifying the amount of a radioactive element removed using radiation detection equipment such as a gamma scintillation counter, a liquid scintillation counter, a flow scintillation analyzer, an alpha spectrometer, a gas proportional counter, an ionization chamber, a Geiger-Muller counter, etc. and quantifying the amount of a non-radioactive element removed using equipment and methods such as inductively coupled plasma mass spectrometry, atomic absorption spectroscopy, neutron activation analysis, X-ray fluorescence, etc.

It is appreciated by those in the field that radioactive elements are very poisonous and radiotoxic in the body, and that non-radioactive elements can also be very poisonous and toxic when present in the body. "Remove", "removing", "removal", and grammatical variants thereof, as used herein, refer to removing a portion or all of a radioactive and/or non-radioactive element from a subject who may become and/or is contaminated with the radioactive and/or non-radioactive element and may include removing a detectable or nondetectable amount of the radioactive and/or non-radioactive element from the subject. Removing a portion or all of a radioactive and/or non-radioactive element (including removing a detectable or nondetectable amount of the radioactive and/or non-radioactive element) from a subject will generally improve the medical condition of the subject. For example, in some embodiments of the present invention at least about 5%, 10%, 15%, 20%, 25%, 30%, 35%, 40%, 45%, 50%, 55%, 60%, 65%, 70%, 75%, 80%, 85%, 90%, 95%, or more of a radioactive and/or non-radioactive element present in a subject is removed according to the methods of the present invention.

Methods for quantifying a subject's exposure level to a radioactive and/or non-radioactive element are known in the art and include, but are not limited to, quantifying the amount of a radioactive and/or non-radioactive element in the area to which a subject was exposed, quantifying by estimating how much of a radioactive and/or non-radioactive element was absorbed or inhaled by a subject, quantifying using whole-body counting instruments, quantifying using external measurements of x-rays emitted from a subject's body, quantifying using physiological based pharmacokinetic models, and quantifying using radioassays of urine, feces, or tissue samples.

According to some embodiments of the present invention, administration of a DTPA prodrug and/or composition of the present invention to a subject may provide an increase in the amount of a radioactive and/or non-radioactive element removed from the subject as a whole and/or from a particular tissue and/or organ (e.g., liver, kidney, bone, muscle, etc.) of the subject compared to the corresponding amount of the radioactive and/or non-radioactive element removed from the subject if the subject was not administered a treatment to remove the radioactive and/or non-radioactive element and/or to the corresponding amount of the radioactive and/or non-radioactive element removed from the subject if the subject were administered a different treatment and/or different mode of administration to remove the radioactive and/or non-radioactive element (e.g., parenteral administration of DTPA). "Increase", as used herein in regard to the amount of removal, refers to an improvement in the amount of a radioactive and/or non-radioactive element removed by about 1% or more, such as, but not limited to, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300% or more.

The dosage regimen of a DTPA prodrug and/or composition of the present invention may be adjusted based on the exposure level and/or the subject. In some embodiments of the present invention, the amount of a DTPA prodrug of the present invention to be administered to a subject may vary according to considerations such as, but not limited to, the particular polymorphic form of the DTPA prodrug, the dosage unit employed, the mode of administration, the period of treatment, the age and/or sex of the patient treated, and/or the nature and extent of the condition treated.

In some embodiments of the present invention, a DTPA prodrug and/or composition of the present invention is designed to deliver about 1 mg to about 2,000 mg of DTPA, a DTPA metabolite, and/or a DTPA prodrug of the present invention per kilogram of a subject's total body weight per day, and in some embodiments, about 10 mg to about 1,000 mg, about 1,000 mg to about 2,000 mg, about 200 mg to about 600 mg, about 1 mg to about 500 mg, about 5 mg to about 250 mg, about 5 mg to about 100 mg, about 15 mg to about 45 mg, or about 10 mg to about 40 mg per kilogram of a subject's total body weight per day. In some embodiments, the dose or amount of a DTPA prodrug delivered to a subject may depend on the binding affinity of the DTPA prodrug for the radioactive and/or non-radioactive element to be removed from the subject. The duration of the administration may be day(s), week(s), month(s), and/or year(s). In certain embodiments of the present invention, the DTPA prodrug and/or composition is administered until there is no detectable amount of a radioactive and/or non-radioactive element present in the subject and/or no detectable amount of a radioactive and/or non-radioactive element removed from the subject for a certain period of time.

A DTPA prodrug and/or composition of the present invention may be used alone or in combination with other therapies and/or therapeutic agents. A DTPA prodrug and/or composition of the present invention may be administered before, during, and/or after administration of another therapy and/or therapeutic agent. In some embodiments of the present invention, a DTPA prodrug and/or composition of the present invention may be used as a follow-up therapy, such as after parenteral administration of a chelating agent, such as, but not limited to, DTPA.

The present invention is explained in greater detail in the following non-limiting Examples.

EXAMPLES

Example 1

Method 1 for Preparing C2E2

The first step in Method 1 for preparing C2E2 (also known as 6,9-bis(carboxymethyl)-3-(2-ethoxy-2-oxoethyl)-

11-oxo-12-oxa-3,6,9-triazatetradecan-1-oic acid) comprises providing DTPA bis-anhydride. DTPA bis-anhydride is commercially available and may be obtained from commercial suppliers, such as TCI America of Portland, Oreg., or may be prepared as follows.

Preparation of Bis-anhydride

Step 1—DTPA (3.93 g, 10 mmol) and acetic anhydride (5.72 g, 56.9 mmol) were added to 6.2 mL of pyridine and heated to reflux 65-70° C. for 14 hours. The material was filtered through a Buchner funnel and rinsed with diethyl ether. An off-white powder (DTPA-BA, 1) was collected and dried in a desiccator. $^{1H}$NMR (400 MHz, DMSO) δ 3.65 (8H, s), 3.44 (2H, d), 2.74 (4H, t), 2.59 (4H, t).

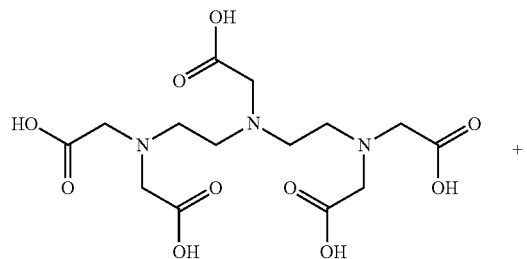

Once DTPA bis-anhydride is obtained, Step 2 is followed to prepare C2E2.

Preparation of C2E2

Step 2—DTPA-BA (1) is used to produce C2E2 (2) by reacting DTPA-BA (1) with ethanol. DTPA-BA (1.02 g, 2.8 mmol), ethanol (0.38 g, 8.2 mmol) and pyridine (0.67 g, 8.4 mmol) were stirred under nitrogen for 24 hours. The product was precipitated in dichloromethane (DCM) (200 mL) at −20° C., filtered while washing with DCM, and dried in a vacuum oven to give an off-white powder (Yield—81.3±13.3, n=4). $^{1H}$NMR (400 MHz, DMSO) δ 4.07 (4H, q), 3.53 (4H, s), 3.45 (2H, s), 3.43 (4H, s), 2.89 (4H, d), 2.84 (4H, d), 1.19 (6H, t). Elemental analysis: Predicted—C, 48.10; H, 6.95; N, 9.35; 0, 35.60; Actual—C, 47.59; H, 7.22; N, 8.67; 0, 36.29. The synthesis of C2E2 has also been successfully prepared on a 2 g scale.

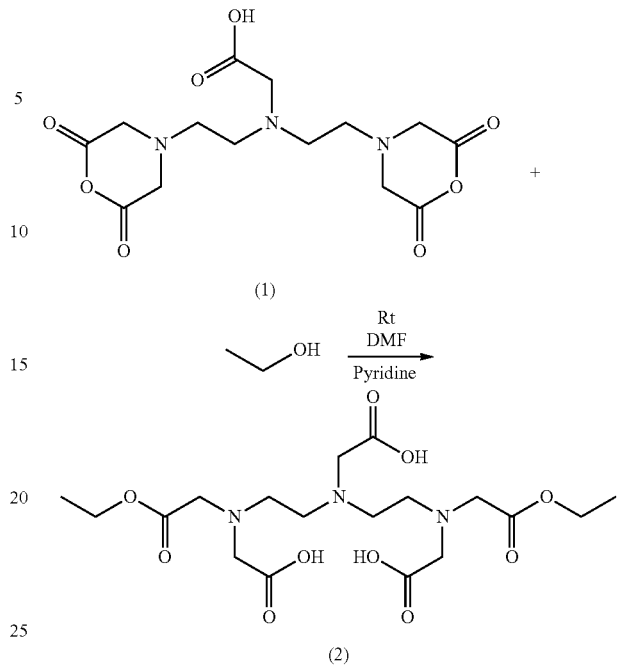

Method 2 for Preparing C2E2

According to Method 2 for preparing C2E2, C2E2 was manufactured on a 1.5 kg scale according to the synthetic scheme in FIG. 1. The synthesis of bis-anhydride 2 from DTPA (1) is described in European Application No. EP136134A1 (2003), International Publication No. WO 2007/142804 A2, and Chemistry, A European Journal, 2004, 10, 3252-3260, the contents of each of which are incorporated herein by reference in their entirely for the teachings relevant to this paragraph. In each case the penta-acetic acid was treated with acetic anhydride and pyridine either neat or in the presence of MeCN and the yield range observed was 95-97%. The bis-anhydride is then converted to C2E2 by reaction with ethanol. This conversion has been used to prepare 800 g as well as 1.5 kg of C2E2.

Preparation of Bis-anhydride (2):

Diethylenetriamine pentaacetic acid (2029 g, 5.16 mole) was dissolved in acetonitrile (1100 mL) with agitation. Acetic anhydride (1450 mL, 15.3 mole) and pyridine (1660 ml, 20.5 mole) were added and the reaction was heated to 60° C. for 4 hours. The reaction mixture was cooled to 22° C. and t-butylmethylether (MTBE) (800 mL) was added. The reaction mixture was filtered and the solid obtained was washed with MTBE (3000 mL). The solid was dried in a vacuum oven at 40° C. Yield: 1792 g, 97%.

Preparation of C2E2:

The bis-anhydride (1792 g, 5.02 mole) was slurried in absolute ethanol (9000 mL) and heated to reflux with agitation for 1.5 hour. The heated reaction mixture was filtered through Celite and cooled below 20° C. The resulting slurry was filtered and washed with cold ethanol (2800 mL) followed by methyl tert-butyl ether (MTBE) (3500 mL). The Celite cake was slurried in ethanol (800 mL) and heated to 70° C. and filtered. On cooling, the slurry obtained was filtered and washed with ethanol and MTBE. The combined isolated solids were dried in a vacuum oven at room temperature. Yield: 1488 g, 66%.

The Certificate of Analysis for the 1.5 kg lot of C2E2 is provided below. Since C2E2 has no chromophore, a reverse phase HPLC method with either evaporative light scattering detection (ELSD) or Charged Aerosol Detection (CAD) was developed and qualified for analysis of C2E2 and impurities.

Certificate of Analysis for C2E2

Structure:

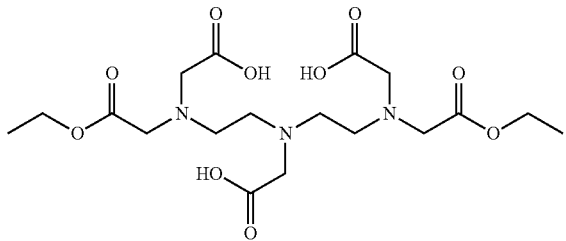

C2E2

Material: C2E2
Lot No: 020WM050
Batch Size: 1.72 kg
Appearance: A white solid.
Identity: Determined by $^1$H NMR. Data are consistent with the structure.
Chromatographic Purity: 97.5% (area %) by Reversed-Phase HPLC-ELSD
Unspecified Individual impurities (area %, average of duplicates):
RRT0.33 0.33%
RRT1.08 1.39%
RRT1.28 0.77%
Total Impurities: 2.49%
Moisture by KF: 0.17%
DSC: Single endotherm centered at 141.6° C. observed.
Polymorphs:

The possibility of multiple C2E2 polymorphs arose during the analysis of C2E2 dosing solutions. The C2E2 dosing solutions were prepared with C2E2 of Lot 050 obtained using Method 2. Investigating polymorphs is important as it affects the physiochemical properties of the bulk powder. Metastable crystalline solids have high chemical potential and are unstable. The difference in physiochemical properties, particle size and surface area can alter the bioavailability of the drug due to changes in dissolution rate. The goal of the following studies was to identify the most stable polymorphic form as any other polymorphs are metastable and could change during storage. This phase change could result in precipitation from solution or instability during storage.

Analysis of Dosing Solutions:

Samples from dosing were received for analysis and checked for leaks and labeling before storing at 4° C. The formulation samples (0, 20, 60, and 100 mg/mL) were diluted to an expected concentration of 0.40 mg/mL and analyzed by HPLC-CAD.

Figure 2:
FIG. 2 shows samples of dosing solutions containing C2E2 from Lot 050, from left to right: 20 mg/mL, 60 mg/mL and 100 mg/mL C2E2 dosing solutions.

During preparation for analysis, the 60 and 100 mg/mL solutions had noticeable solid precipitated from the formulations, as seen in FIG. 2. The diluted samples were prepared and analyzed as if the solutions contained the indicated amount of C2E2. The results shown below in Table 1, show poor percent recoveries with no clear trends related to concentration. Both 20 and 100 mg/mL solutions fall outside the accepted range of 85-115% recovery. The 60 mg/mL solution is technically within the recommended preparation range, but the formulation contained solid precipitate.

TABLE 1

Percent recovery of C2E2 from dosing formulations.

| Dosing formulation concentration (mg/mL) | Percent recovery (%) of C2E2 |
|---|---|
| 0 | 0 |
| 20 | 184.87 |
| 60 | 92.08 |
| 100 | 220.42 |

Stability Study in Water:

Method 2 was used to prepare the C2E2 for the dosing formulations. Specifically, Lots 050 and 005-2 were prepared using Method 2, whereas the Reference standard and MTD Lot were prepared using Method 1. For the dosing formulations, de-ionized water (DI water tap in room 18/19) was used with the C2E2 prepared using Method 2. The dosing formulations were compared with C2E2 formulations prepared using Milli-Q water. The pH of each sample was recorded and the values are listed below in Table 2.

TABLE 2 pH values of solubility samples.

| Formulation | pH of formulations prepared using de-ionized water | pH of formulations prepared using Milli-Q water |
|---|---|---|
| Vehicle (water) | 6.97 | 4.95 |
| 20 mg/mL (Lot 050) | 3.04 | |
| 60 mg/mL (Lot 050) | 2.93 | |
| 100 mg/mL (Lot 050) | 2.93 | 2.60 |
| 100 mg/mL (Lot 005-2) | | 2.54 |
| 100 mg/mL Purified C2E2 (Reference std) | | 2.43 |
| 100 mg/mL (MTD Lot) | | 2.35 |

The pH of the vehicles differs by nearly two units. The pH of the different 100 mg/mL preparations of Batch 050 differs by only 0.3 pH units, though the concentrations are likely not equivalent due the amount of precipitated material in the sample. The pH values of the different C2E2 preparations made using Method 1 range from 2.35 to 2.60. While these differences are small, it does seem likely that the C2E2 in Lots 050 and 005-2 have a slightly higher solution pH than that of the MTD Lot and Reference standard (the Reference standard is a purified C2E2 from the MTD Lot). While not wishing to be bound to any particular theory, this may be due to the presence of impurities in the Reference standard and MTD Lot.

In order to re-create the unusual solutions, 1-mL samples of C2E2 (Lots 005-2 and 050; MTD Lot; and Reference std) were made at concentrations of 100 mg/mL in Milli-Q water. A set of samples was stored at room temperature, in the refrigerator (4° C.), and in the −20° C. freezer. Observations of these solutions at various time points show that within 24 hours the reference material starts to precipitate as a fine powder, regardless of the storage temperature. Lot 050 also begins to come out of solution after three days, but as slightly clumpy materials. Storage at 4° C. exacerbates the precipitation of Lot 050. After 8 days, both the Reference Standard and Lot 050 have significant amounts of solid detected at 4° C. and room temperature and crystals have started to form. Freezing and thawing does not cause unreasonable precipitation. The two preparations that are relatively less pure (the MTD Lot and Lot 005-2) do not come out of solution. While not wishing to be bound to any particular theory, this is likely because more impurities increase the solubility.

Figure 3:
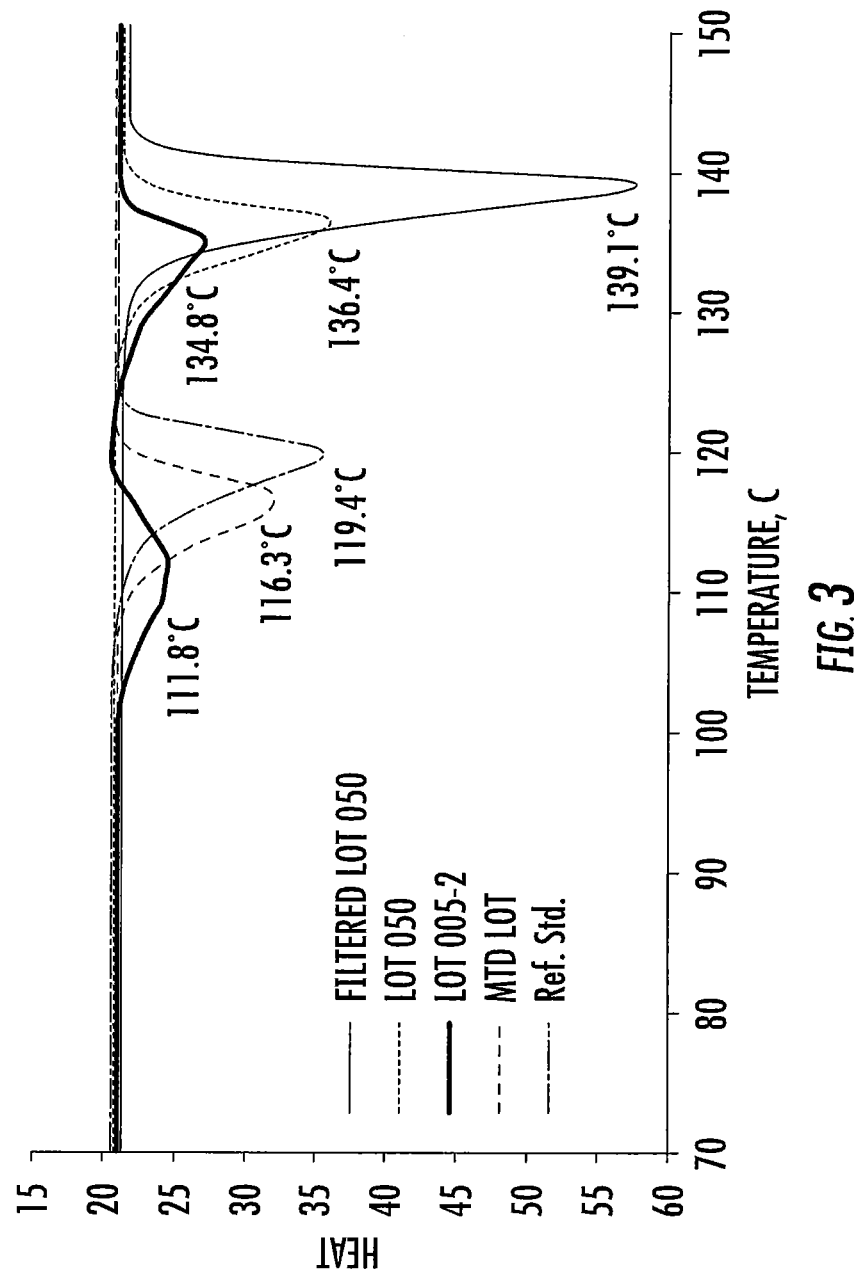
FIG. 3 shows differential scanning calorimetry (DSC) data for C2E2 preparations.

Differential Scanning Calorimetry (DSC):

Samples of C2E2 (~5 mg) were crimped and evaluated by DSC over a range of 25° C. to 320° C. with a heating rate of 10.00° C./min. A sample was also cycled three times from 25 to 150° C. with a heating rate of 10° C./min and a cooling rate of 5° C./min. The results of DSC analysis are shown in FIG. 3. Both the MTD Lot and the Reference Standard show a melting point near 120° C. Lot 050 has a melting point of about 140° C. The material filtered from the dosing formulation for Lot 050 also has a melting point of about 140° C., suggesting that the C2E2 used for dosing preparations has the same composition as that which comes out of solution. The differences in melting point suggest the presence of polymorphs possibly due to the presence of different solvates.

Interestingly, the impure batch of C2E2 (Lot 005-2) has two melting points, one near 120° C. and the other near 140° C. While initially it was assumed that the second peak was due to C2E3 detected by MS and HPLC, without wishing to be bound to any particular theory, it now seems likely that the two peaks are indicative of two types of C2E2 present. Both of these peaks are broadened, probably a result of impurities (such as the C2E3 detected by NMR/HPLC/MS).

Figure 4:
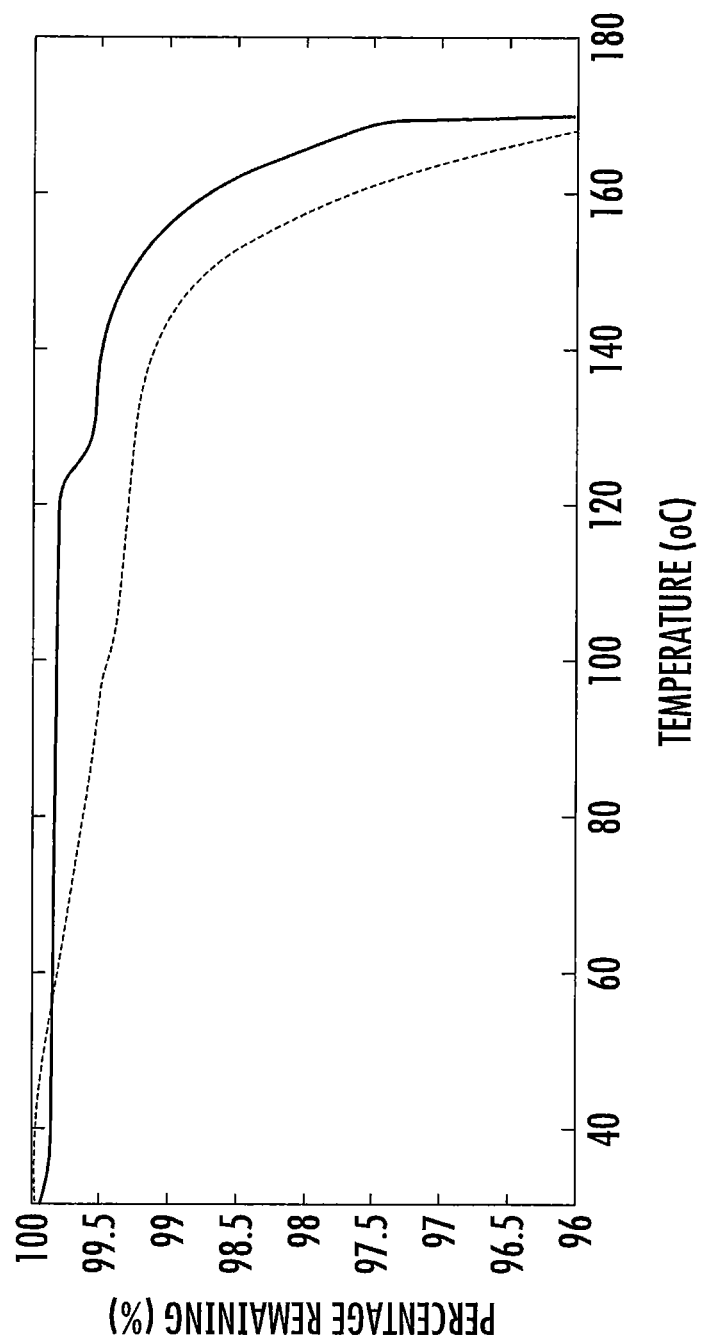
FIG. 4 shows the comparison of the thermogravametric data obtained for both C2E2 batches. Method 1 is the dotted line and Method 2 is the solid line.

C2E2 starts to combust at temperatures above 150° C. When the mixed batch of material (Lot 005-2) with two melting points is cycled slowly from 25 to 150° C., no shift from one melting point to another is seen. In fact, after one heating cycle, no other peaks were seen, though no combustion was seen on the endotherm. While not wishing to be bound to any particular theory, it had been anticipated that a shift from the lower temperature to the higher would occur, but it is likely that the cycling conditions were not ideal.

function of temperature and thus can be used to study the desolvation or decomposition of the compound. This information is useful in combination with the DSC data, as desolvation processes are accompanied by a weight change, whereas solid-liquid or solid-solid phase transitions are not associated with a change and therefore not present on the TGA thermogram. Solids from both synthesis methods were placed on the TGA and heated using the following method. Initial temperature was set to 25° C. and the temperature was increased at 10° C./min to 100° C. An isothermal step was introduced at 100° C. for 5 min to ensure all water loss had occurred, and then the temperature was further increased at 10° C./min to 170° C. (FIG. 4).

Firstly, the TGA data confirms that the endotherms observed on the DSC are melting points as there is no significant weight change observed on the TGA thermogram for either compound at the associated temperature, which is indicative of a phase change rather than decomposition or desolvation. Lot 050 exhibits a gradual weight loss that may be due to the presence of surface water. The MTD Lot has no significant loss in weight aside from a 0.5% decrease between 116-123° C. While not wishing to be bound to any particular theory, due to the fact that there is no stoichiometric weight loss seen, it is unlikely that this is caused by the presence of a hydrate or solvate. The small weight loss may be an impurity that is released as the polymorph begins to melt. Both polymorphs begin to decompose around 170° C. as seen by the rapid weight loss.

Elemental Analysis:

Elemental analysis was performed on the Reference Standard and Lot 050 samples. The elements requested for analysis were C, H, N, and O. The results of the elemental analysis C2E2 are shown in Table 3. The Reference Standard sums to 98.92% of the total weight, indicating a very small level of contamination. On the other hand, the Lot 050 sample has 1.93 weight percent unaccounted for. Thus, it is unlikely for solvent to account for the difference seen between synthetic lots.

TABLE 3

Percent composition of C2E2 preparations.

| Sample ID | Carbon wt % | Percent of theoretical | Hydrogen wt % | Percent of theoretical | Nitrogen wt % | Percent of theoretical | Oxygen wt % | Percent of theoretical |
| --- | --- | --- | --- | --- | --- | --- | --- | --- |
| UNC Ref. std | 48.1 | 100 | 6.57 | 94.5 | 9.40 | 100.53 | 34.85 | 97.89 |
| Lot 050 | 48.3 | 100.42 | 6.60 | 94.96 | 9.31 | 99.57 | 33.86 | 95.11 |
| Theoretical | 48.10 | | 6.95 | | 9.35 | | 35.60 | |

Competitive Ripening Experiment:

A brief competitive ripening experiment was conducted to determine the more stable melting point. 50 mg each of Lot 050 and the Reference standard were combined in 500 μL of water and stirred at room temperature overnight. After stirring, the remaining solid was filtered from the liquid, allowed to dry and analyzed by DSC. The competitive ripening experiment showed that the solid material recovered from a stirred mixture of two materials had only a single melting point of 140° C. While not wishing to be bound to any particular theory, the favoring of the higher temperature suggests that the material with the higher melting point is the more stable compound.

Thermogravimetric Analysis:

A second thermal analysis method, thermogravimetric analysis (TGA) was used to characterize the compounds. TGA measures the thermally induced weight loss as a

Figure 5:
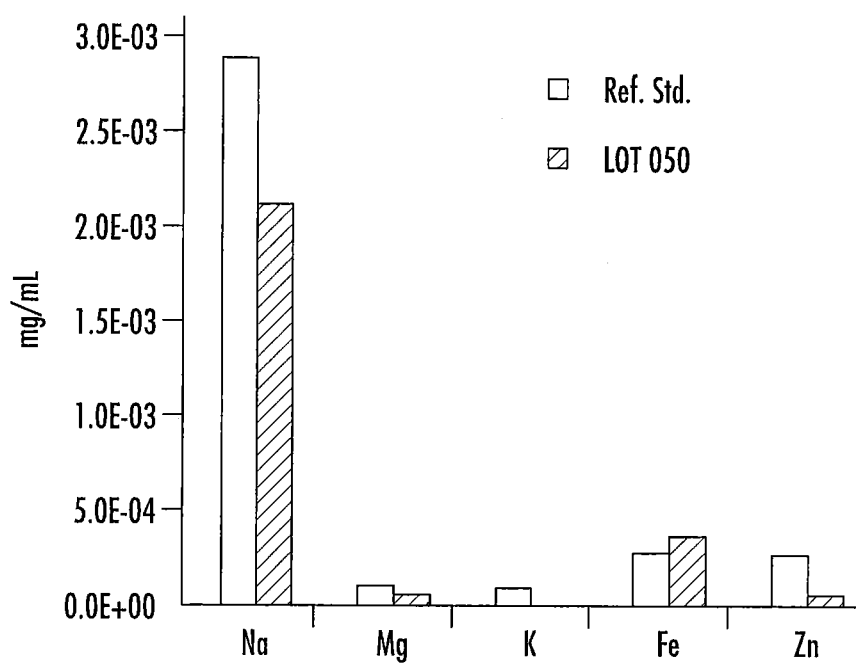
FIG. 5 shows a graph of the concentrations of metal ions in C2E2 preparations as detected by inductively coupled plasma mass spectrometry (ICP-MS).

IPC/MS:

To eliminate a metal chelate as a possibility for the differences in the C2E2, each preparation was analyzed by ICP-MS. Dilutions of C2E2 (Reference Standard and Lot 050) were made in water to a concentration of 110 mg/mL. The results are shown in FIG. 5. There are no differences of note between the two C2E2 samples. Sodium has the highest concentration detected, between 2 and 3 μg/mL for the 110 mg/mL C2E2. Other elements (magnesium, potassium, iron and zinc) are present at concentrations less than 500 ng/mL, and are nearly equal between the two samples. This small amount of metal is possibly due to the water or glassware used and is unlikely to be responsible for the distinct differences in the melting points seen on the DSC.

X-Ray Powder Diffraction:

Samples of C2E2 (Reference Standard, MTD Lot, Lot 050 and Lot 005-2) were analyzed by X-ray powder diffraction by K Sueda at GSK. Analysis of C2E2 samples was conducted by K Sueda and results are shown in FIGS. 6-8. All four spectra are shown in FIG. 6. Overlays of the Reference Standard and MTD Lot show the same crystal structure with only minor differences (FIG. 7) and are distinctly different from the crystal structure of Lots 050 and 005-2. Lots 050 and 005-2 are different from each other (confirming the HPLC and DSC data) (FIG. 8). Lot 005-2 more closely resembles the Reference Standard and MTD Lot and, without wishing to be bound to any particular theory, may be a mixture of crystals.

While not wishing to be bound to any particular theory, the differences between the C2E2 samples is not due to solvation or chelation, and is most likely a case of polymorphism. It appears that Lot 050 is more stable (higher melting point) in its solid state.

Figure 9:
Figure 9:

Scanning Electron Microscopy:

Final confirmation of the presence of two polymorphs was obtained using scanning electron microscopy. Powdered samples were sputter coated with a 5 nm thick coating and imaged. The C2E2 MTD Lot is scaly in nature, as opposed to the divergent habit of Lot 050, which possesses a distinct crystal form as shown in FIG. 9.

While not wishing to be bound to any particular theory, the data discussed above suggest that C2E2 has at least two polymorphic forms. The higher melting point and lower solubility (observed as precipitating out during storage in the refrigerator) suggests that the polymorph seen in Lot 050 is the most stable.

Figure 10:
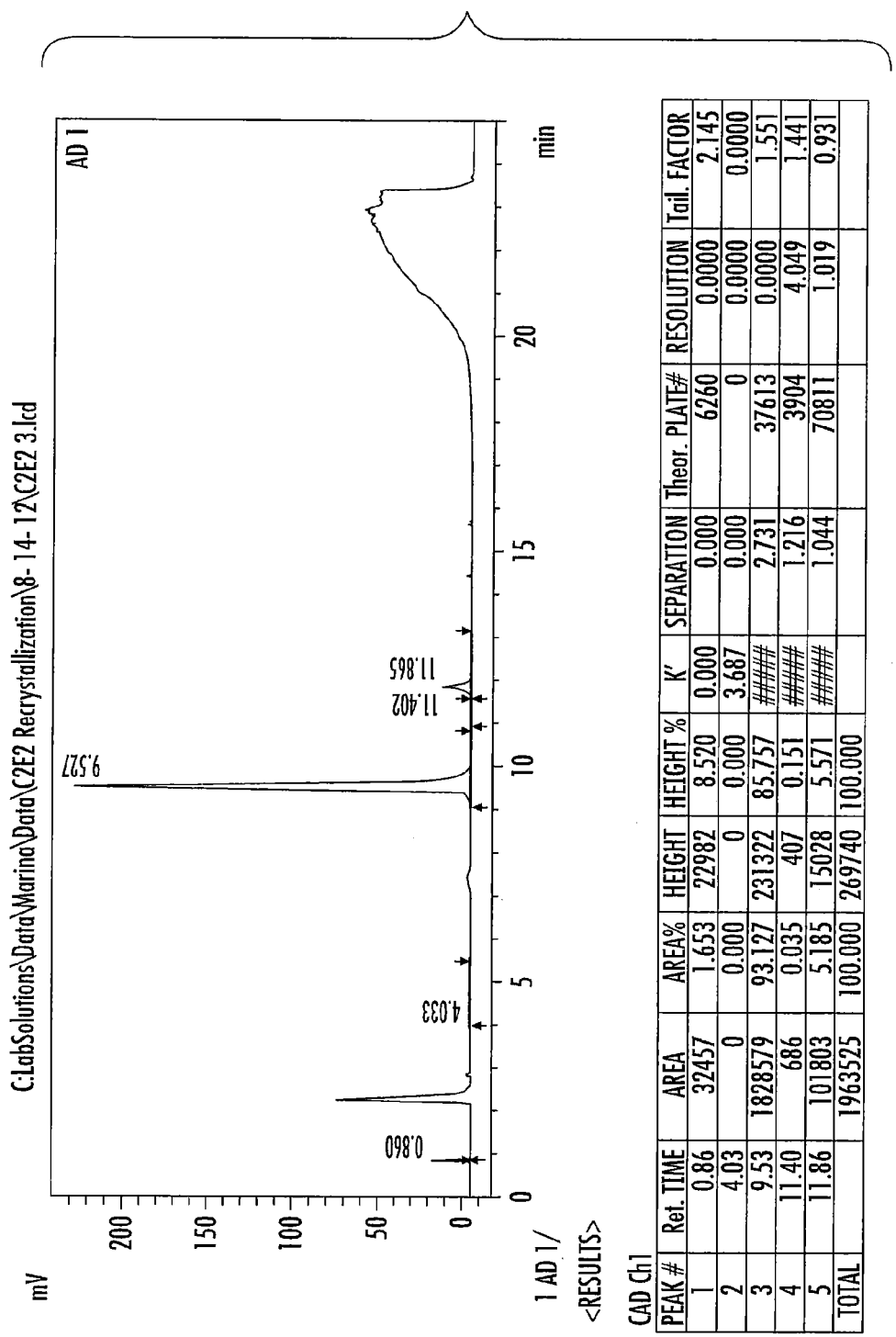

Recrystallization Studies of C2E2:

Lot 050 has known impurities of ethanol and API related material, likely small amounts of C2E3 and C2E1. The chromatogram of this material is shown in FIG. 10. The small peak with RT of 11.86 min has an approximate area of 5.2% in this injection. There is no C2E1 detected (RT ~4.5 min), and the peak at 2.5 min is consistent with the injection dead volume.

Figure 11:
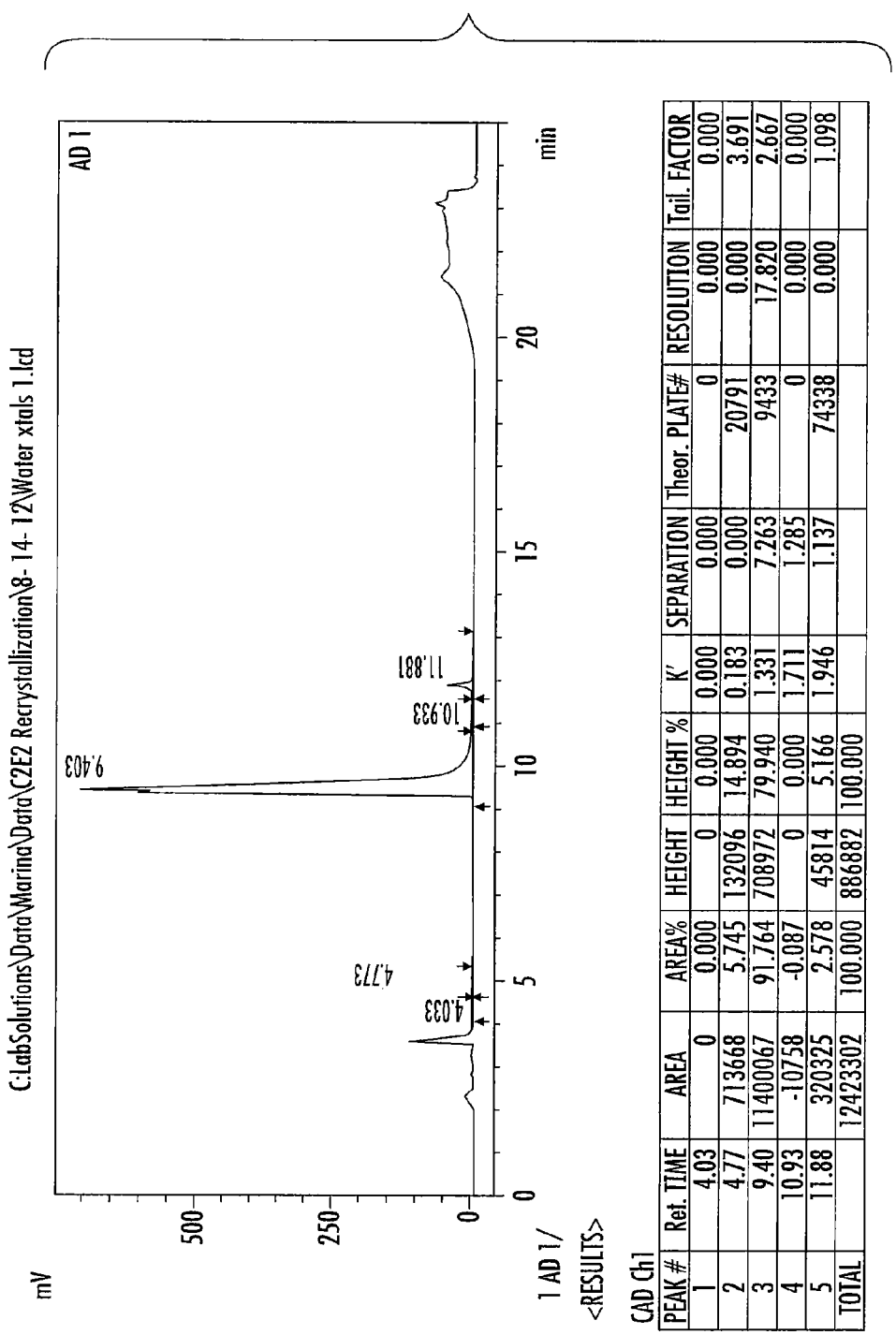

A solution of C2E2 (100 mg/mL) was prepared in water and upon sitting for several weeks produced clear cubic crystals. A small amount of these crystals were dissolved in water and analyzed by HPLC. The resulting chromatogram is shown in FIG. 11. The peak area of C2E3 (RT 11.8) decreased slightly to ~2.6%, but the C2E1 peak has increased to 5.7%.

Figure 12:
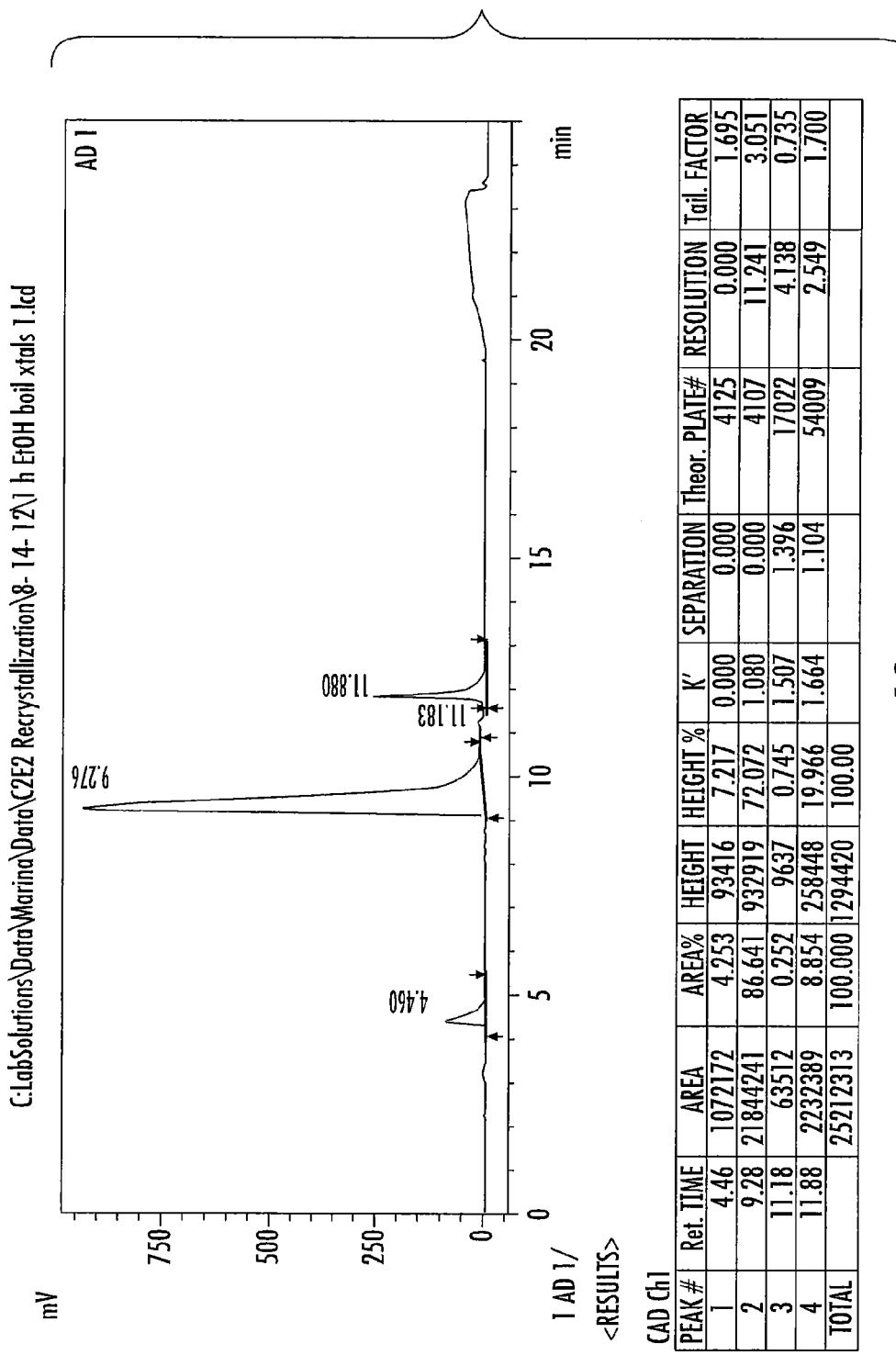
Figure 13:
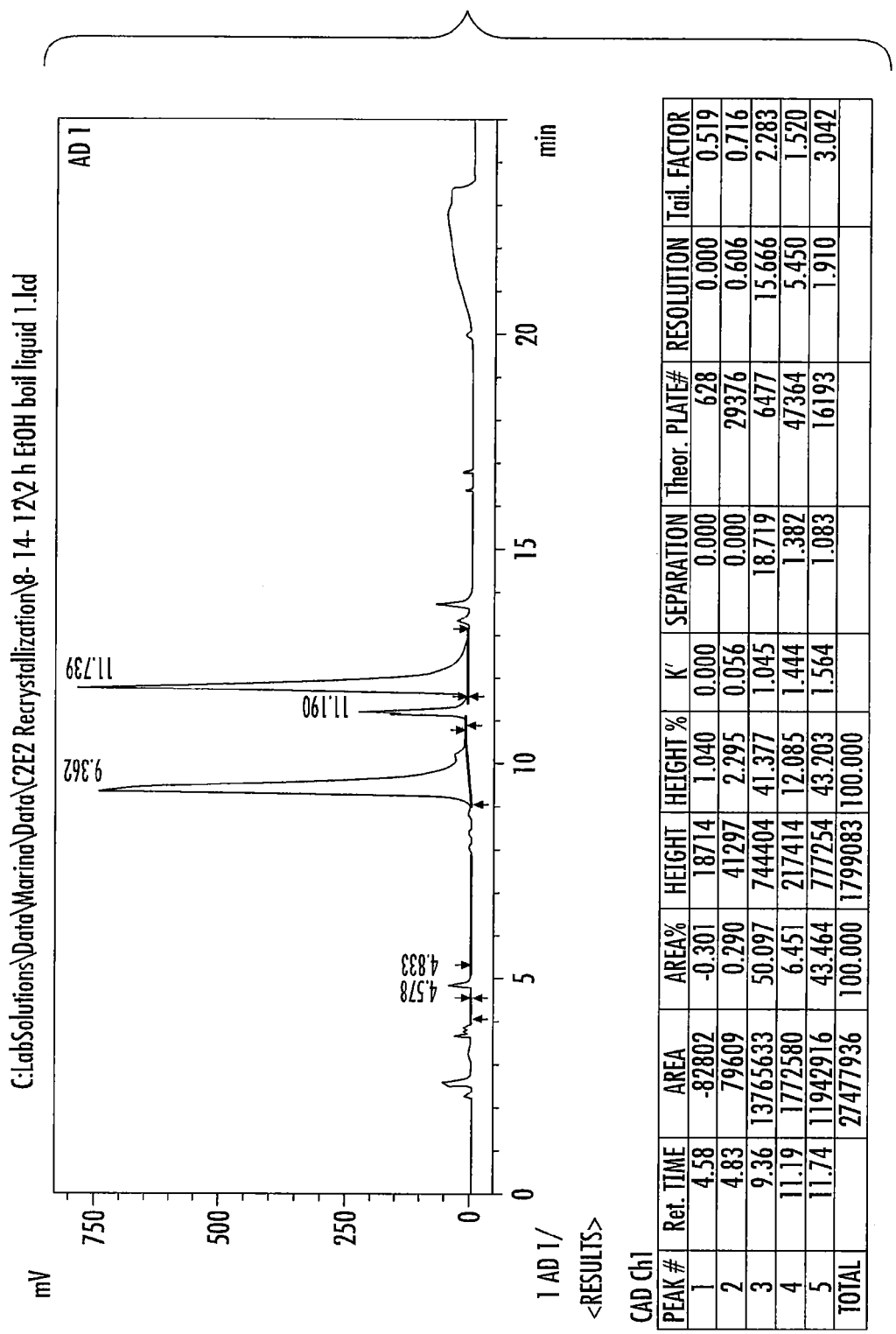

Recrystallization of C2E2 from ethanol was also identified as a possible route to improve purity. As such, small portions of C2E2 were heated in ethanol (200 proof) until all material was dissolved. The vials were cooled and C2E2 precipitated slowly. The material resulting from ethanol heating and cooling was white and powdery in nature, microcrystalline rather than discrete visible crystals. FIGS. 12 and 13 show chromatograms of the solid and liquid material from a one hour heating in ethanol (dissolution of C2E2 in ethanol is slow). The solid material recovered from this experiment shows increased percentages of C2E3 (8.8%) and C2E1 (4.3%), suggesting that this route of 'purification' is unlikely to result in a reference standard quality material. The filtrate, while enriched in C2E3 (RT 11.8) also contains a significant amount of C2E2. This residual material suggests that a significant amount of C2E2 would be sacrificed while not generating C2E2 in the desired purity.

While not wishing to be bound to any particular theory, this study shows that the recrystallization of C2E2, while seemingly simple, is likely to introduce larger amounts of additional impurities while decreasing the C2E3 present. While C2E2 is relatively stable in solution, the addition of heat or moisture leads to esterification or de-esterification and is likely to produce C2E3 or C2E1 and DTPA.

Aqueous Solubility

Preliminary Test:

A small sample of C2E2 (0.1 g, JH012B) was weighed out and placed in a 25 mL graduated cylinder. Increasing volumes of distilled water were added according to the chart below:

| Volume water added (mL) | 0.1 | 0.5 | 1 | 2 | 10 | 100 | >100 |
|---|---|---|---|---|---|---|---|
| Approximate solubility (g/L) | >1000 | 200-1000 | 100-200 | 50-100 | 10-50 | 1-10 | <1 |

After each addition of the indicated amount of water, the mixture was stirred for 10 minutes and visually checked for any dissolved parts of the sample. The preliminary test showed that C2E2 was soluble in 10 mL of water after 10 minutes. The approximate solubility is therefore 10-50 g/L.

ADME

Metabolic Stability:

Caco-2 cells are a human colon epithelial cancer cell line that expresses transporters, efflux proteins and phase II enzymes and can be used to correlate cell permeability with drug absorption. In addition to determining the apparent permeability coefficient, an estimation of C2E2 metabolism during transport can be obtained. The aim of these preliminary studies was to evaluate a range of C2E2 concentrations (25, 50 & 100 µM) in order to determine a linear concentration range in which further studies could be performed.

Caco-2 cells (passage #39) were cultured in 75 $cm^2$ T-flasks at 37° C. in a 5% $CO_2$ constant humidity environment. The medium was replaced 3 times a week and the monolayers were sub-cultured to passage #41. When plating the cells 0.5 mL of a 120,000 cells/mL suspension was added to each apical (AP) compartment of the first and then 1.5 mL of cell culture medium was placed into the basolateral (BL) compartment of the Transwells®. Following 21-24 days on the Transwell® plates with media changes 2-3 times a week the Caco-2 transport studies were performed.

Prior to the transport experiments the transport medium was warmed to 37° C. Transport medium consisted of Hank's Balanced Salt Solution (HBSS) (1×) with calcium and magnesium 500 mL with the addition of 1M HEPES buffer (5 mL) and 1.25M D-Glucose solution in HBSS (10 mL). The cell culture medium was removed from the Transwells® to be used for the experiment and each well was washed twice with warm transport medium. The Transwells® were then pre-incubated for 30 min with transport medium. Finally, the trans-epithelial resistance (TEER) values for each Transwell® were measured using a voltohmmeter and chopstick electrode. The TEER values should be in the range of 300-750 and should vary as little as possible. Dosing solutions were prepared in warm (37° C.) transport medium. Pre-incubated transport medium was removed from the Transwells® and 1.5 mL fresh 37° C. transport medium was pipetted into the acceptor compartment. At time zero 0.5 mL of the dose was pipetted into the donor compartment. The Transwells® were then placed in a 37° C. incubator for the duration of the experiment. At each time point (20, 40, 60 & 120 min) the transport medium was collected and diluted with acetonitrile. The Transwell® was transferred into a new acceptor compartment containing 1.5 mL of fresh pre-heated transport medium. The concentration of C2E2 was then determined by LC-MS/MS. The concentration of the dosing solutions was also measured to determine the concentration in the donor compartment at time zero. During these preliminary studies, the transport from the apical to the basolateral compartment was investigated.

Figure 14:
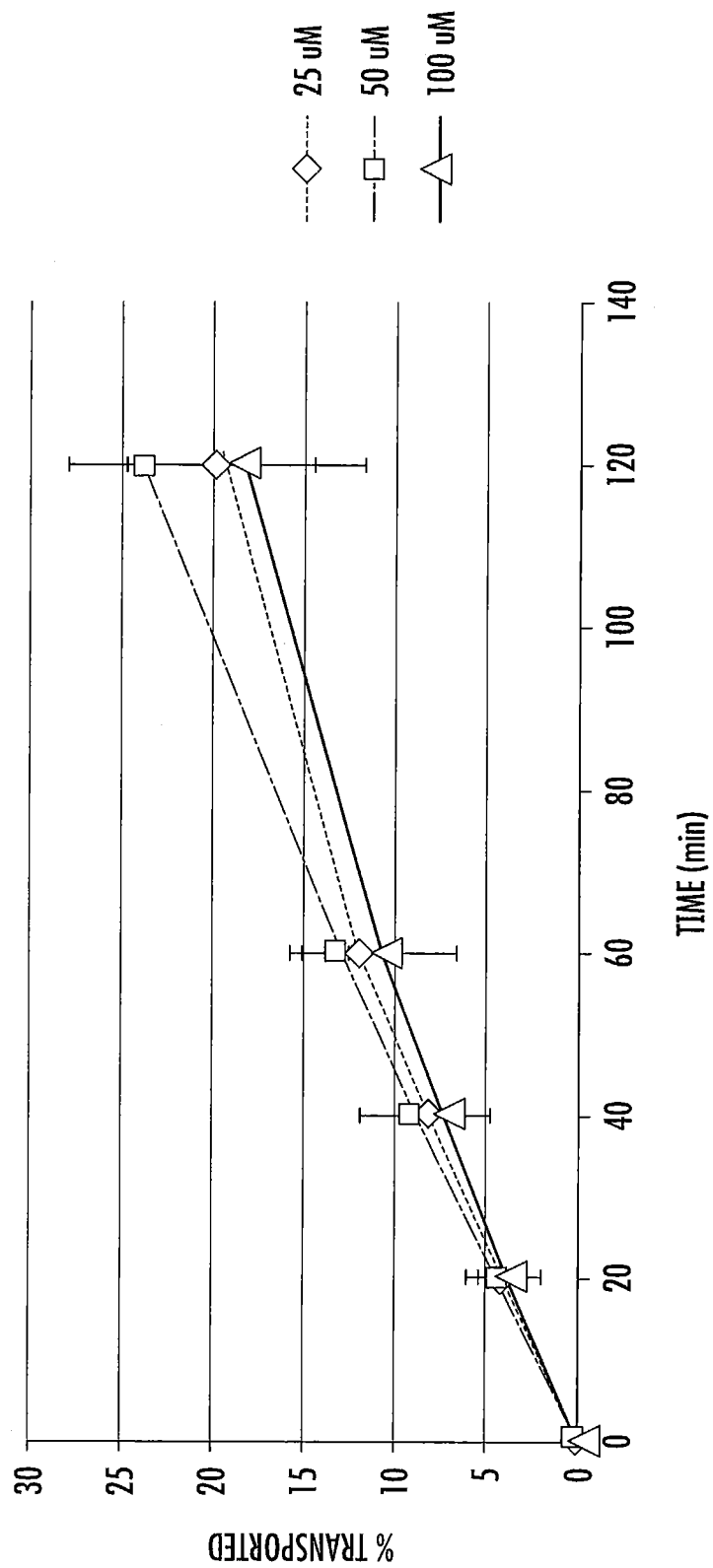

C2E2 was detected in the basolateral receiver compartment at all concentrations tested. The percentage of dose that passed through the membrane was similar for all three concentrations as shown in FIG. 14. Between 18-22% of the dose was detected in the receiving compartment. Although none of the lines are statistically different, the 100 µM plates exhibited the lowest percentage transport.

Figure 15:
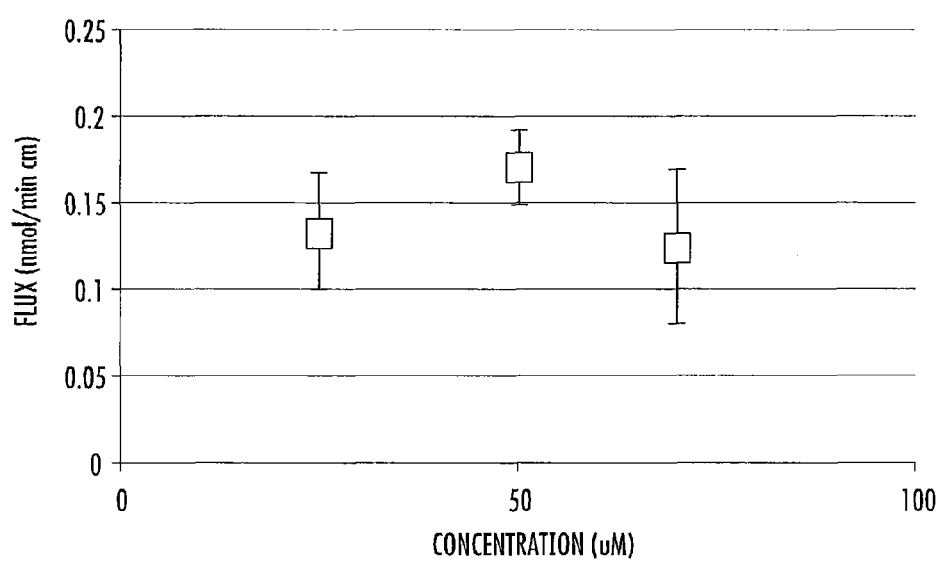

One of the goals of these experiments was to determine if at these doses there was a linear response. FIG. 15 shows the flux calculated for each concentration. As the flux is a measure of the mass of material moving through the membrane per unit time if the dose response was linear then higher concentrations should exhibit a higher flux. In these experiments the highest dose level had the lowest flux. While not wishing to be bound to any particular theory, this could be because the concentration is no longer in the linear range; alternatively it may be due to the processing of this data on the mass spectrometer as the 100 µM samples were run in a separate run. The data from all the sample concentrations should be combined and reprocessed to ensure that the data was processed identically.

Figure 16:
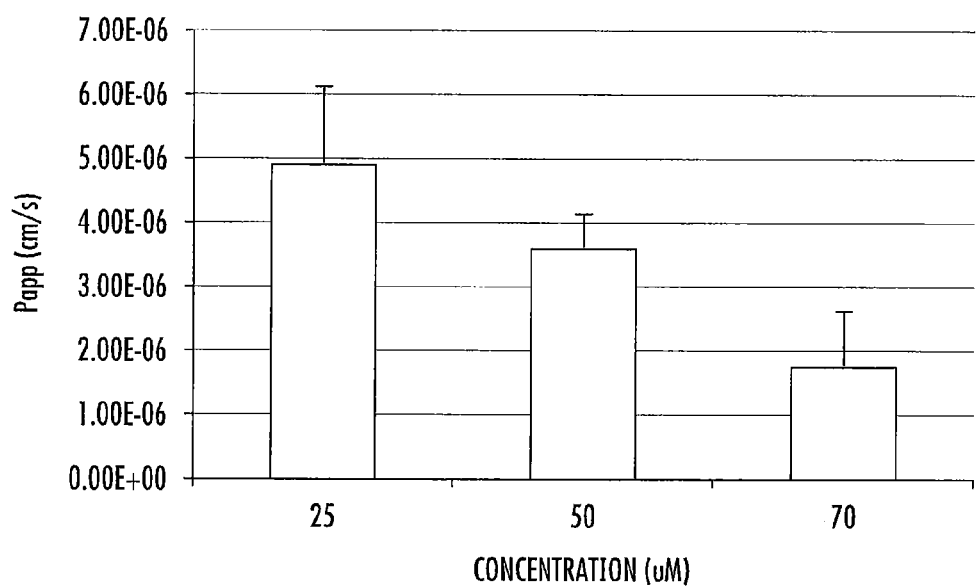

FIG. 16 shows a decrease in the apparent permeability coefficient with increasing dose of C2E2. If the C2E2 was absorbed by passive diffusion then the permeability coefficient should be constant. Thus the decrease may be due to a number of reasons. The absorption may be transport mediated and at increasing concentrations of C2E2 either apical uptake into the Caco-2 cell or basolateral efflux becomes saturated. Alternatively p-gp may efflux the C2E2 on the apical membrane thereby limiting absorption. Additional experiments such as measuring the transport of C2E2 from the basolateral to the apical side and assessing the effect of p-gp inhibitors on the transport of C2E2 are required to determine the cause of the decrease in $P_{app}$ with increasing concentration.

The relationship between the apparent permeation coefficient determined in Caco-2 experiments with the percentage dose absorbed in humans is described in Shiyin Yee (*Pharm. Res.*, 1997 June; 14(6):763-6.), the contents of which is incorporated herein by reference in its entirety for the teachings relevant to this paragraph. Based on the data of Shiyin Yee, the observed apparent permeation coefficient of $4.88 \times 10^{-6}$ cm/sec suggests that C2E2 would be moderately (20-70%) absorbed in humans providing that dissolution and GI metabolism are not limiting factors.

Efficacy

Summary of C2E2 Single Dose Decorporation in Rats:

This study was to assess the efficacy of a single oral gavage dose of C2E2 in $^{241}$Am contaminated rats. A 200 µL aliquot was withdrawn from a stock solution of $^{241}$Am nitrate (0.1 mCi in 5 mL 1 M $HNO_3$), evaporated to dryness, dissolved in concentrated $HNO_3$ (15 M, 5 mL) then evaporated to dryness and dissolved in dilute $HNO_3$ (0.1 M, 8 mL) to form the injection solution. Groups of 4 female Sprague-Dawley rats were contaminated with 250 nCi of $^{241}$Am nitrate by IM injection (0.1 µL) then were administered single doses of C2E2 by gavage at 200, 600, or 1000 mg/kg under ad lib feeding conditions utilizing a 10% w/w solution in sterile water (dose volumes were 2, 6, and 10 mL/kg, for the 200, 600, and 1000 mg/kg doses, respectively). For the fasted component of the study, the animals were fasted 24 hours before treatment then for 2 hours post drug administration. Control groups with ad lib access to food and water were either untreated or administered an IV dose of the calcium salt of DTPA (Ca-DTPA) at 14 mg/kg (target dose volume of 0.7 mL/kg and concentration of 20 mg/mL). Treatment was administered 1 day after contamination. All animals were euthanized 7 days after contamination and the following tissues were collected: liver, both kidneys, both femurs as well as the ipsilateral and the contralateral hind leg muscle tissue and the pelt from the injection site. Urine and feces were collected from the time of contamination through euthanasia. Cage washings were also collected at the end of the study and considered part of total urine collection. Two aliquots (100 µL) of the injection solution were removed and $^{241}$Am gamma activity was determined using radiomatic detection. The average of these standards is the injected dose used for all animals. All tissues and samples were counted in a similar manner. Americium content was expressed as a percentage of the injected dose. Overall recovery of radioactivity across all groups in this study was approximately 90%. Table 4 shows total decorporation and residual liver burden at euthanasia in untreated controls and after a single dose of Ca-DTPA or C2E2. The primary route by which both DTPA and C2E2 enhanced elimination of $^{241}$Am occurred was by urinary clearance. Results suggest feeding state did not affect total $^{241}$Am clearance. Fecal clearance of $^{241}$Am was not altered by feeding status, an observation that is consistent with the similar liver burden between the two groups at the end of the study. This study demonstrated C2E2 increased total body decorporation in female rats and reduced $^{241}$Am liver burden in a dose-dependent manner. As with DTPA, enhanced decorporation by C2E2 occurred through enhanced urinary clearance.

TABLE 4

Americium Decorporation 7 days After IM Contamination: Treatment with a Single Dose of C2E2 24 h after Contamination.

| | Urine (%) | Feces (%) | Cage Wash (%) | Total Decorporation (% injected) | Liver burden (% injected) |
|---|---|---|---|---|---|
| DTPA Dose (mg/kg) | | | | | |
| 14 | 22.1 ± 2.6 | 10.3 ± 1.7 | 3.6 ± 0.8 | 36.1 ± 4.6 | 12.3 ± 1.2 |
| C2E2 Dose (mg/kg) | | | | | |
| 0 | 4.7 ± 1.0 | 4.9 ± 1.0 | 1.6 ± 0.5 | 11.2 ± 2.1 | 21.4 ± 2.5 |
| 200 | 6.7 ± 1.5 | 5.9 ± 0.8 | 1.8 ± 0.5 | 14.4 ± 0.7 | 17.7 ± 2.1 |
| 200 (fasted) | 8.4 ± 1.3 | 4.7 ± 2.1 | 1.3 ± 0.5 | 14.3 ± 3.2 | 20.9 ± 3.5 |
| 600 | 12.4 ± 1.3 | 7.7 ± 2.0 | 2.2 ± 0.8 | 22.3 ± 3.1 | 18.6 ± 4.5 |

TABLE 4-continued

Americium Decorporation 7 days After IM Contamination: Treatment with a Single Dose of C2E2 24 h after Contamination.

|  | Urine (%) | Feces (%) | Cage Wash (%) | Total Decorporation (% injected) | Liver burden (% injected) |
|---|---|---|---|---|---|
| 600 (fasted) | 14.3 ± 2.9 | 7.3 ± 1.5 | 2.6 ± 0.8 | 24.2 ± 3.3 | 18.9 ± 2.3 |
| 1000 | 13.5 ± 1.7 | 6.9 ± 1.7 | 3.4 ± 0.3 | 23.8 ± 3.0 | 14.5 ± 1.5 |
| 1000 (fasted) | 19.8 ± 3.9 | 7.1 ± 1.3 | 4.5 ± 0.7 | 31.3 ± 5.5 | 13.7 ± 3.1 |

The Full Details of this Study are as Follows:

Male and female Sprague Dawley rats (n=4/gender/dose) were administered single oral doses of diethylenetriaminepentaacetic acid diethyl ester (C2E2) by gavage 24 hours after intramuscular contamination with $^{241}$Am(NO$_3$)$_3$ (250 nCi) under ad libitum and fasted conditions. Animals received single oral nominal doses of 200, 600, or 1000 mg/kg C2E2. Untreated animals and animals treated with an intravenous dose of Ca-DTPA (13.3 mg/kg) 24 hours after contamination served as controls; only ad libitum conditions were used for control animals. Total radionuclide decorporation and radionuclide tissue burden were evaluated seven days after contamination.

C2E2-dose dependant americium decorporation was observed in both male and female rats following C2E2 treatment, with benefits of C2E2 treatment evident at doses of 600 mg/kg and above. At 1000 mg/kg, a single C2E2 oral dose is comparable, in terms of efficacy, to an intravenous dose of Ca-DTPA (13.3 mg/kg), although equivalence analysis has not been conducted. Of the other effects examined, the study established that rat gender significantly influences americium decorporation and tissue burden, but fasting prior to administration of the C2E2 dose does not. This determination resulted in data from ad libitum and fasted groups being combined for statistical analysis; male and female groups still required separate analysis. Consistent with a previous single dose toxicology study (UNC-11.240-RMTD), no C2E2-related clinical signs were observed over the 7-day period.

By reducing the amount of americium in key tissues and increasing the amount of americium that is removed from the body, a single oral C2E2 dose can effectively treat americium contamination in a rat wound model of contamination. C2E2 efficacy has been demonstrated at doses considerably below the maximum tolerated single dose (2000 mg/kg) for the species.

Introduction and Objective:

The objective of this study was to investigate effects of food, gender, and dose, on the tissue burden and decorpoartion of $^{241}$Am following a single oral dose of C2E2. The delay between contamination and treatment selected for this study was 24 hours; this reflects a realistic treatment delay for an orally administered drug in a mass casualty situation. Results obtained from this study will be used to design dose regimen pharmacology studies in rats.

Materials and Methods:

This study was conducted under The University of North Carolina at Chapel Hill Protocol UNC-10086-E7SD.

Test and Control Article:

The Test Article, C2E2 from the MTD Lot, was documented to be 98% pure, no correction for purity was made in preparing dose solutions. The Test Article was stored at room temperature. Control Article (Ca-DTPA; Hameln Pharmaceuticals) was stored at room temperature. The records of disposition are maintained in the study file.

Test and Control Article Formulation:

The Test Article was dissolved on each day of dosing in sterile water (Hospira Inc.) to achieve a 10% w/w solution. Control article (Ca-DTPA) was diluted in 0.9% Saline (Baxter International) on the day of dosing. Analysis of dosing solutions was not performed.

Radionuclide Preparation:

The $^{241}$Am injection solution was prepared. A 200 μL aliquot of the stock $^{241}$Am(NO$_3$)$_3$ solution (0.1 mCi/mL in 1 M HNO$_3$) was removed and placed in a 20-mL glass vial. The aliquot was evaporated to dryness in a stirred oil bath. Concentrated nitric acid (15 M, ≈5 mL) was added to the dry americium nitrate and the resultant solution evaporated to dryness. To form the injection solution, dilute nitric acid (0.1 M, 8 mL) was added to the dry 20-mL vial, the solution was then filtered into a 10 mL injection vial, capped and stored securely until use.

Test System:

Naive and jugular catheterized male and female Sprague Dawley rats were purchased from Charles River Laboratories (Raleigh, N.C.). Shortly after their arrival at the laboratory, the animals were removed from the shipping cartons and examined. No evidence of disease or physical abnormalities was identified. At contamination, the animals were 260-310 g male and 210-320 g female. The fate of all animals is documented in the study records.

Allocation:

Body weights were measured prior to $^{241}$Am administration. Individual weights of animals placed on study were within ±20% of the mean weight for each gender with one exception (female with body weight −20.5% of the mean). Animals considered suitable for the study based on the pre-study observations were assigned to test or control article groups. Animals were not randomized due to space limitations.

Identification:

Each animal was assigned a temporary identification number and cage location upon receipt. Immediately after contamination, animals were assigned a cage number and location and a unique number assigned by the Testing Facility (Table 5).

Animal Husbandry:

Animals were individually housed in metabolic cages (Techniplast USA). Environmental parameters were recorded and are included in the study file. Temperature (desired range of 68±3° F.), humidity (approximately of 30 to 70%), lighting (12 hour light/dark cycle; 0700-1900 hrs), and air exchanges (20-30 air changes per hour) in the housing area were monitored to ensure that the conditions were maintained to the maximum extent possible. Room sanitation and opening/closing room door may have temporarily created excursions. Drinking water from the Chapel Hill, N.C. municipal water system and standard rodent chow (Labdiet, Prolab RMH 3000) were provided ad libitum except where indicated.

Experimental Groups:

Individual animal number assignments and experimental groups are shown in Table 5.

TABLE 5

Animal Number Assignments.

| Dose (mg/kg) | Food Access | Animal Identification Number UNC-10086-E7SD | |
|---|---|---|---|
| | | Male | Female |
| Untreated | ad libitum | 447-450 | 443-446 |
| 200 | ad libitum | 475-478 | 431-434 |
| 600 | ad libitum | 459, 460, 462, 492 | 487-490 |
| 1000 | ad libitum | 465, 466, 496, 497 | 491-494 |
| 14 (i.v.Ca-DTPA) | ad libitum | 471-474 | 467-470 |
| 200 | Fasted | 479-482 | 483-486 |
| 600 | Fasted | 451-454 | 435-438 |
| 1000 | Fasted | 455-458 | 439-442 |
| Total | | 32 | 32 |

Americium Contamination:

Male and female Sprague Dawley rats were contaminated with $^{241}Am(NO_3)_3$ (0.25 µCi) by intramuscular injection (0.1 mL, 0.1 M $HNO_3$) into the right hind leg, under isoflurane anesthesia. Immediately after injection, body weights were recorded (Day 0 weight) and animals were placed in individual metabolic cages.

Fasting:

Approximately eight hours after contamination—and 16 hours before test article administration—rats assigned to the Fasted groups had access to food restricted by removing the food chamber from their metabolic cages and collecting all loose chow from their housing chambers. Food chambers were replaced 1 hour after oral gavage treatment, restoring access to food. At all other times all animals had ad libitum access to food.

Administration of Test Article:

Male and female Sprague-Dawley rats assigned to test groups each received a single oral gavage dose of 0, 200, 600, or 1000 mg/kg of C2E2 utilizing a 10% w/w solution in water 24 hours after contamination. In some animals, brief exposure isoflurane (5% by vaporizer) was required during dosing to reduce the spread of radionuclide. Dose volume in these groups ranged from 2-10 mL/kg. Doses were based upon the Day 0 weight (immediately after contamination). Mass of the dosing solution administered to each rat was recorded.

Administration of Control Article:

Under isoflurane anesthesia four male and four female Sprague-Dawley rats each received a single intravenous dose of the Ca-DTPA solution (13.3 mg/kg) via a jugular vein catheter 24 hours after contamination utilizing a 0.67 mL/kg followed by a 0.2 mL flush of 0.9% sterile saline. The mass of the administered Ca-DTPA dosing solution was recorded. Doses were based upon the Day 0 weight (recorded immediately after contamination).

Euthanasia:

Scheduled euthanasia by isoflurane overdose and thoracotomy was performed seven days after contamination.

Viability Checks:

All animals were observed at least once daily for morbidity, mortality, and general appearance.

Excreta:

Excreted urine and feces were collected daily, allowed to dry overnight, transferred to 20-mL scintillation vials, weighed and placed in a gamma counter (Wizard2 2480, Perkin Elmer) for detection of $^{241}Am$ gamma activity.

Body Weights:

Each rat was weighed at contamination (Day 0) and the terminal body weight (Day 7) was taken at necropsy.

Food Consumption:

Food consumption was monitored daily by visual inspection to be sure there was a sufficient amount of feed. The animals had a continuous supply of feed available to them except where indicated.

Post Mortem:

Scheduled animals were brought to the necropsy room, euthanized by isoflurane overdose followed by thoracotomy, their terminal body weights were recorded and selected tissues removed, weighed and placed in a gamma counter (Wizard$^2$ 2480, Perkin Elmer) for detection of $^{241}Am$ gamma activity.

Sample Analysis:

The total amount of $^{241}Am$ administered to the animals was determined by quantifying the 59.7 keV photons emitted by $^{241}Am$ in duplicate aliquots (100 µL) of the injection solution using a gamma counter (wizard series, Perkin-Elmer). A counting window from 40-80 keV and a 60-second counting time were used for acquisition and each reading was corrected for background at acquisition. All experimental tissues and samples were counted using the same gamma counter and protocol. For all the samples, $^{241}Am$ content was expressed as a percentage of the initial dose. The femur from the leg opposite to the injection site was scaled by a factor of 20 to estimate total skeletal $^{241}Am$ burden.

Statistics:

Statistical analysis was performed for final decorporation parameters—total decorporation, liver burden, wound retention and estimated skeletal burden. All animals treated with C2E2 were analyzed by ANOVA to evaluate the effects of gender, dose and fed state. Non-contributing effects were removed from the model and control data (untreated and Ca-DTPA treatment groups) were included for subsequent analysis. ANOVA was performed and Least squares means calculated for all the groups in this model. Comparison of means was made using the Tukey-Kramer adjustment for multiple comparisons, with $p<0.05$ considered significant.

Results

Animals:

Contamination and subsequent treatment of male and female rats occurred in nine cohorts between June $9^{th}$ and August $24^{th}$. Three male rats in a cohort started August $2^{nd}$ died as a result of experimenter error during gavage treatment, additional animals were added to the August $24^{th}$ cohort to replace these lost animals. Some difficulty was experienced in dosing female rats. Specifically, the dosing solution was observed in the mouth during gavage in five female rats. In the two instances where dosing solution remained confined to the mouth, the observed volume was considered insignificant with no adverse effects noted; these rats were retained in the analysis. However, in three rats some loss of dose from the mouth occurred and partial aspiration of the dose may have occurred as brief difficulty breathing was observed. Although no adverse effects of dosing in these animals were observed at one hour after dosing and they completed the in-life portion of the study these animals were excluded from data analysis.

Clinical Observations:

No adverse C2E2 exposure-related clinical observations for male rats or female rats were identified in any of the dose groups. Individual animal clinical observation data are included with daily excreta data on Daily Cage Observations sheets in the study file.

Body Weights:

Body weights were recorded at contamination and at euthanasia for all animals. Mean body weights and percentage change in body weight during the study are shown in Table 6 and Table 7. Although significant differences are observed between different groups in both male and female animals, these are not anticipated to influence the outcomes of the study. One female animal (body weight −20.5% of mean) was included in the study despite being outside the ideal weight range (20% of mean weight for gender).

TABLE 6

Mean Body Weights of Male and Female Sprague-Dawley Rats

| C2E2 Treatment | ad libitum | | Fasted | |
| --- | --- | --- | --- | --- |
| (mg/kg) | Day 0 | Day 7[1] | Day 0 | Day 7[1] |
| Male | | | | |
| Untreated | 276.3 ± 8.5 | 310.2 ± 19.4 | ND | ND |
| 200 | 296.3 ± 9.4 | 326.5 ± 25.7 | 291.3 ± 12.7 | 314.2 ± 14.4 |
| 600 | 292.8 ± 5.1 | 322.2 ± 6.4 | 275.9 ± 9.7 | 310.6 ± 9.1 |
| 1000 | 290.5 ± 6.6 | 321.2 ± 6.5 | 270.3 ± 5.8 | 302.8 ± 14.2 |
| 14 (iv Ca-DTPA) | 301.0 ± 4.0 | 314.6 ± 20.4 | ND | ND |
| Female | | | | |
| Untreated | 294.8 ± 11.4 | 279.3 ± 19.1 | ND | ND |
| 200 | 276.8 ± 17.3 | 276.5 ± 15.1 | 245.0 ± 11.6 | 246.8 ± 9.6 |
| 600 | 247.0 ± 13.8 | 249.7 ± 14.5 | 280.5 ± 28.0 | 273.5 ± 19.2 |
| 1000 | 232.5 ± 19.3 | 234.2 ± 21.4 | 276.3 ± 17.9 | 262.7 ± 23.8 |
| 14 (iv Ca-DTPA) | 273.6 ± 7.7 | 273.3 ± 11.2 | ND | ND |

[1]Mean body weights are terminal weights

TABLE 7

Mean Percentage Body Weight Change.

| C2E2 Treatment | Male | | Female | |
| --- | --- | --- | --- | --- |
| (mg/kg) | ad libitum | Fasted | ad libitum | Fasted |
| Untreated | 12.4 ± 7.8 | ND | −5.3 ± 3.1 | ND |
| 200 | 10.4 ± 11.0 | 8.1 ± 8.4 | 0.0 ± 2.5 | 0.8 ± 2.2 |
| 600 | 10.1 ± 3.1 | 12.6 ± 3.1 | 1.1 ± 1.2 | −2.3 ± 3.3 |
| 1000 | 10.6 ± 0.8 | 12.0 ± 4.8 | 0.7 ± 2.1 | −5.0 ± 2.9 |
| 14 (iv Ca-DTPA) | 4.5 ± 6.1 | ND | −0.1 ± 1.9 | ND |

Data Analysis of $^{241}$Am Excretion:

Sixty-four rats completed the study, of these 61 rats (32 male and 29 female) were included in data analysis. Three fasted female rats (1×600 mg/kg; 2×1000 mg/kg) were excluded from the dataset as they did not receive a complete dose.

Effect of Food on $^{241}$Am Decorporation:

The americium content in daily urinary and fecal output from male (FIG. 17) and female (FIG. 18) rats indicate that the efficacy of the C2E2 dose was not altered by fasting rats prior to their C2E2 treatment.

Figure 17:
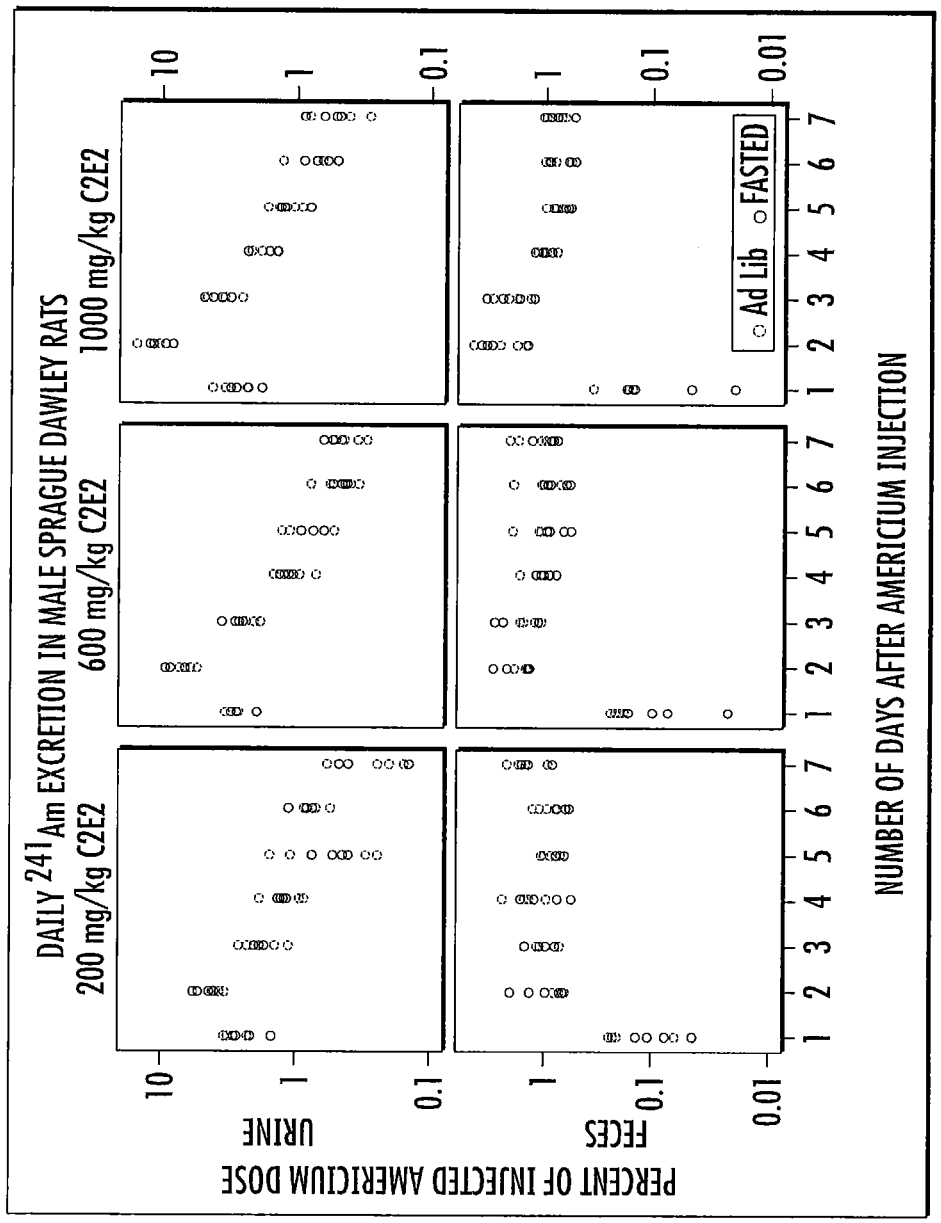
Figure 18:
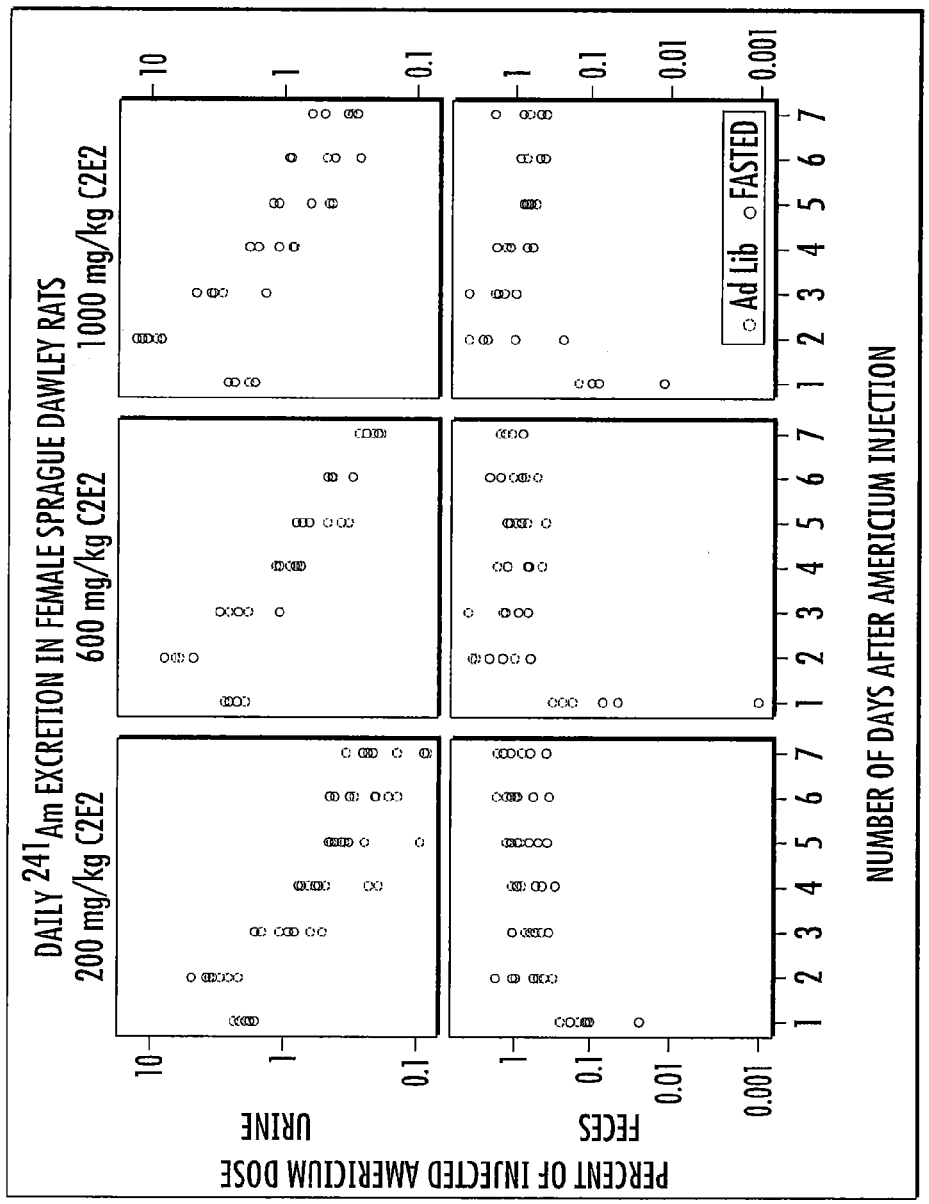

Analysis of the total decorporation achieved in the seven days after contamination for all the rats treated with C2E2 showed significant effects for gender ($F_{(1,44)}=17.54$, $p<0.001$) and C2E2 dose ($F_{(2,44)}=40.71$, $p<0.001$) but not for Fed state at treatment ($F_{(1,44)}=1.51$, $p=0.23$), confirming the observations in FIGS. 17 and 18. Interactions between effects were not considered significant and therefore, for subsequent analysis ad libitum and fasted groups were combined. Statistical analysis has not been applied to daily data.

Figure 19:
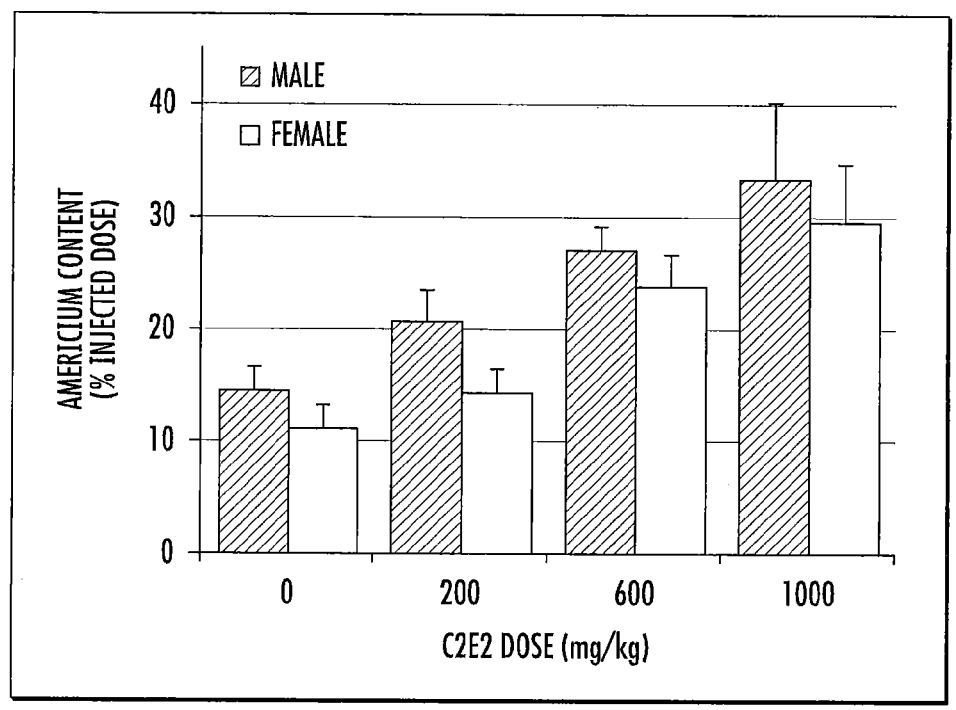

Effect of Gender on $^{241}$Am Decorporation:

Americium decorporation in male rats is significantly greater over the seven days of the study than in female rats ($F_{(1,60)}=21.37$, $p<0.001$; FIG. 19). The observed difference between genders is consistent across all the different treatment groups (untreated, three C2E2 doses and Ca-DTPA) and is not statistically significant at any individual treatment level.

Effect of C2E2 Dose on $^{241}$Am Decorporation: C2E2 enhanced the elimination of americium in a dose dependent manner in male and female rats. In male rats total decorporation was significantly increased compared to untreated controls at doses of 600 mg/kg and above ($p<0.001$) and increasing the dose from 600 mg/kg to 1000 mg/kg also significantly increased decorporation ($p<0.05$). A similar trend was observed in female rats with doses above 600 mg/kg inducing significantly enhanced decorporation ($p<0.001$), the 1000 mg/kg dose appears to be more effective than the 600 mg/kg dose although this did not reach statistical significance.

Data Analysis of $^{241}$Am Tissue Burden:

Tissues and organs were collected from all 64 rats that completed the study, of these 61 rats (32 male and 29 female) were included in data analysis. Three fasted female rats (1×600 mg/kg; 2×1000 mg/kg) were excluded from the dataset as they did not receive a complete dose.

Effect of Food on $^{241}$Am Tissue Burden:

Americium burden in liver, wound site tissue were determined and the skeletal burden was estimated seven days after contamination in animals treated with 200, 600, or 1000 mg/kg C2E2 one day after intramuscular contamination. For all of the tissues no difference in americium burden was observed between rats with ad libitum access to food and rats fasted overnight prior to C2E2 treatment (Liver, $F_{(1,44)}=0.02$, $p=0.88$; Wound, $F_{(1,44)}=0.84$, $p=0.37$; Skeleton, $F_{(1,44)}=0.02$, $p=0.88$). In contrast, in these animals gender was a significant factor with male rats having lower retention than female rats (Liver, $F_{(1,44)}=72.97$, $p<0.001$; Wound, $F_{(1,44)}=12.87$, $p<0.01$; Skeleton, $F_{(1,44)}=48.29$, $p<0.001$). C2E2 dose also influenced tissue burden (Liver, $F_{(2,44)}=8.52$, $p<0.01$; Wound, $F_{(2,44)}=10.03$, $p<0.001$; Skeleton, $F_{(1,44)}=4.79$, $p<0.05$). Interactions between effects were not considered significant and for subsequent analysis ad libitum and fasted groups were combined.

Figure 20:
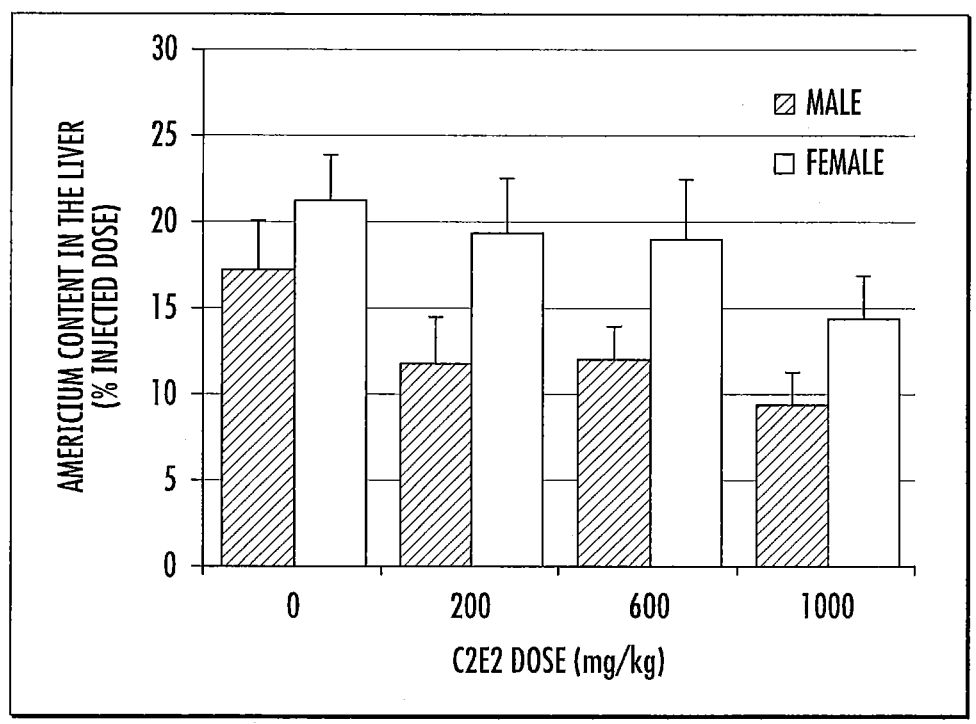

Effect of Gender on $^{241}$Am Tissue Burden:

For all animals in the study, lower liver and wound site americium burdens were observed in male rats than in female rats (Liver, $F_{(1,60)}=91.24$, $p<0.001$ and Wound, $F_{(1,60)}=18.59$, $p<0.001$). Although the trend for higher average americium retention at the wound site in female rats was observed across all groups (FIG. 20) it only reached statistical significance in the 200 mg/kg C2E2 dose ($p<0.05$). Ca-DTPA and C2E2 reduced americium burden in male rat livers compared to female rat livers (14 mg/kg Ca-DTPA, $p<0.05$; 200 and 600 mg/kg C2E2, $p<0.001$; and 1000 mg/kg C2E2, $p<0.05$), americium burdens in untreated rats were not significantly different between genders ($p=0.42$). In contrast to the liver and wound site, the estimated skeletal burden was lower in the female rats than in male rats ($F_{(1,60)}=58.51$, $p<0.001$). In the Ca-DTPA groups the estimated skeletal burden was not significantly influenced by gender ($p=1.00$) for all other groups estimates of female americium skeletal burden were lower than in comparable males (Untreated and 200 mg/kg C2E2, $p<0.001$; 600 and 1000 mg/kg C2E2, $p<0.05$).

Figure 21:
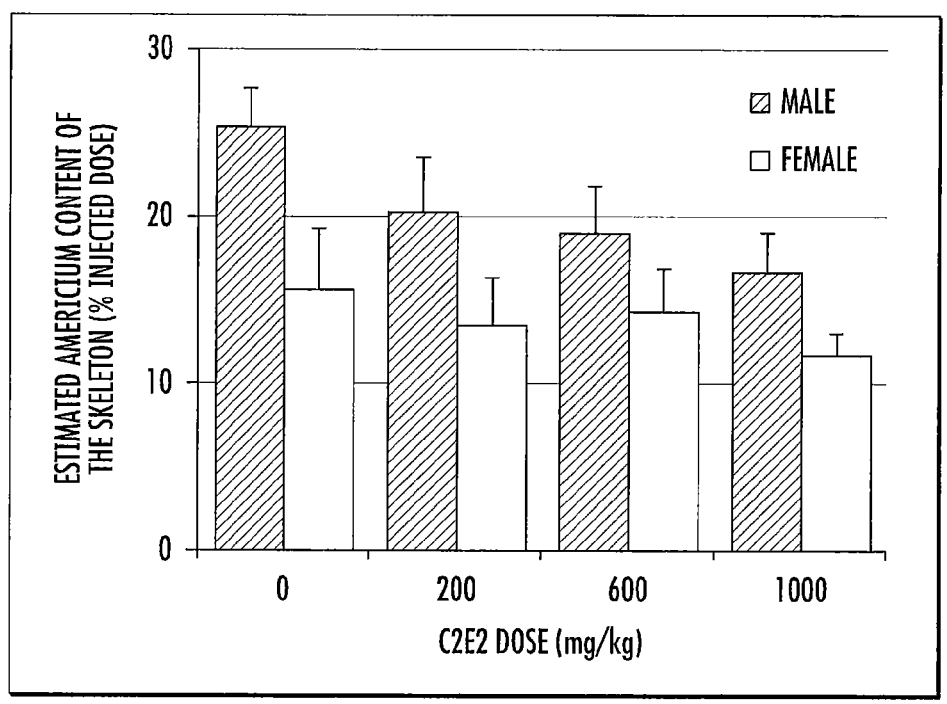
Figure 22:
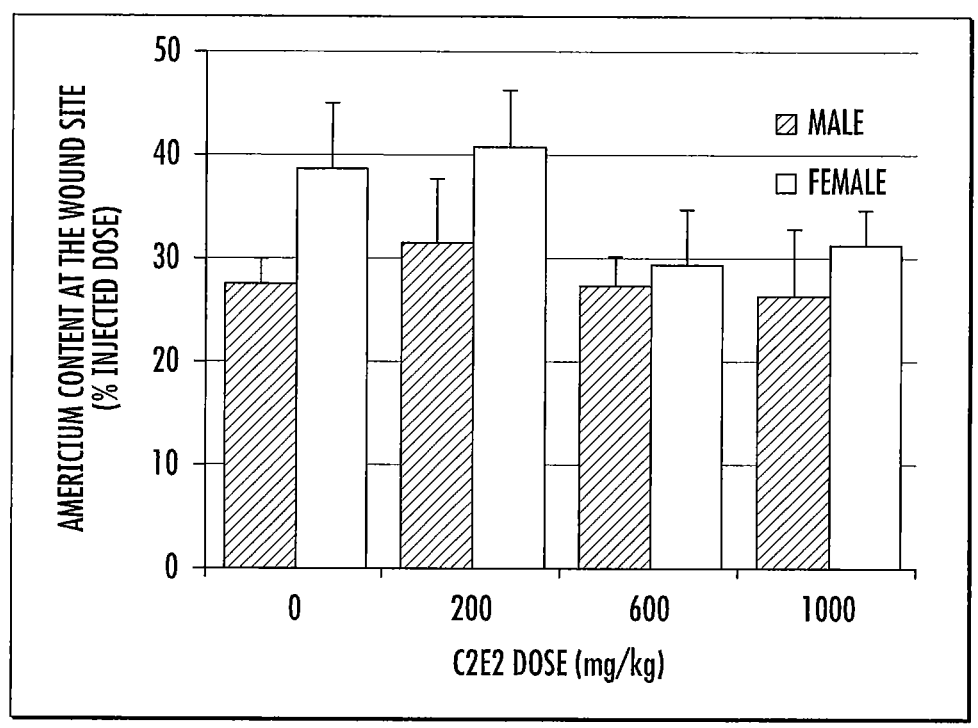

Effect of C2E2 Dose on $^{241}$Am Tissue Burden:

In both male and female rats, C2E2 reduced the americium burden in liver, skeleton, and at the wound site. In male rats, the liver burden was significantly reduced compared to untreated controls at doses of 200 mg/kg ($p<0.05$) and 1000 mg/kg ($p<0.001$). Although the liver burden following a 600 mg/kg C2E2 dose did not reach statistical significance ($p=0.056$) it is consistent with the trend of C2E2 treatment reducing liver burden. A dose-dependent reduction in $^{241}$Am liver burden was observed in female rats. Only the reduction in burden following the 1000 mg/kg dose was statistically significant compared to untreated controls at the 1000 mg/kg dose ($p<0.01$). Estimated skeletal americium burden in male rats decreased in a C2E2 dose dependent manner with significant reduction compared to untreated control animals at doses of 600 mg/kg and above. Skeletal burden in female rats was lower than in male rats for all groups and was not significantly changed by C2E2 treatment (FIG. 21). Although overall C2E2 dose was a significant effect for wound site retention of americium ($F_{(3,52)}=7.92$, $p<0.01$) this effect did not correspond with a significant change in tissue burden compared to untreated controls at any single C2E2 dose (FIG. 22). In female rats, a trend for reduced burden with increasing C2E2 dose may exist; C2E2 appeared to have no effect on skeletal burden in male rats.

In conclusion, a single oral dose of C2E2 can induce significant improvement in outcome based on primary measures—decorporation, liver burden and skeletal burden. C2E2 efficacy is independent of food although it is dependent on gender; this dependence is consistent with the differences between genders seen in untreated and Ca-DTPA treated animals and is due to a gender difference in the biokinetics of americium rather than a direct C2E2 effect.

Efficacy Studies in Dogs:

Dogs were administered $^{241}$Am (target of 3 µCi/animal) by nose-only inhalation on Day 0. At 1 day post exposure, animals received one of three different oral doses (10, 300, 500 mg/kg) of C2E2. Group 1 was a control and was used for determining the unperturbed biokinetics. Fourteen (14) days post C2E2 administration, the animals were sedated and euthanized. Preliminary urinary excretion and liver retention data were obtained (Table 8). These results demonstrated that C2E2 administered orally to contaminated dogs was able to enhance urinary excretion of the radionuclide and reduce liver burden.

TABLE 8

$^{241}$Am recovery in urine and livers of dogs treated with C2E2 orally.

| | | Total Recovered Activity (nCi) | | | | | |
|---|---|---|---|---|---|---|---|
| Gender | C2E2 Dose (mg/kg) | Urine | Gender Mean | Treatment Mean | Liver | Gender Mean | Treatment Mean |
| M | 0 | 14.14 | 13.47 | 15.17 | 326.2 | 230.03 | 189.93 |
| M | 0 | 12.80 | | | 133.9 | | |
| F | 0 | 13.95 | 16.86 | | 108.4 | 149.84 | |
| F | 0 | 19.77 | | | 191.3 | | |
| M | 100 | 187.57 | 169.10 | 168.70 | 213.3 | 179.89 | 168.91 |
| M | 100 | 150.63 | | | 146.5 | | |
| F | 100 | 193.85 | 168.30 | | 186.4 | 157.92 | |
| F | 100 | 142.75 | | | 129.4 | | |
| M | 300 | 97.24 | 157.29 | 169.50 | 109.2 | 120.06 | 132.28 |
| M | 300 | 217.34 | | | 130.9 | | |
| F | 300 | 121.32 | 181.71 | | 87.6 | 144.49 | |
| F | 300 | 242.10 | | | 201.4 | | |
| M | 500 | 288.78 | 274.65 | 188.82 | 49.4 | 49.73 | 45.01 |
| M | 500 | 260.53 | | | 50.1 | | |
| F | 500 | 65.39 | 103.00 | | 34.3 | 40.30 | |
| F | 500 | 140.61 | | | 46.3 | | |

Toxicology

10-Day Repeat-Dose Study in Dogs:

An exploratory study was conducted to evaluate the toxicity and to determine the toxicokinetics of the test article, C2E2, when administered to dogs via 10 daily oral gavage doses. Groups of 2 Beagle dogs/sex were administered C2E2 via oral gavage at dose levels of 0, 60, 200, 400, or 600 mg/kg. The vehicle was reverse osmosis water and the dose volume was 8 mL/kg. Assessment of toxicity was based on mortality, clinical observations, body weight, food consumption, clinical pathology, gross pathology, organ weights, histopathology of selected tissues, and plasma essential trace elements analysis. Blood samples were collected on Days 1 and 10 for toxicokinetic evaluations of C2E2, C2E1, DTPA and C2E3. C2E3 is believed to be an impurity in the C2E2 lot used.

Two animals were sacrificed early due to moribund condition, one male given 600 mg/kg/day and one male given 400 mg/kg/day. These animals had notably higher plasma C2E2 concentrations than other animals in their respective dose groups. Based on clinical pathology findings and microscopic evidence of hepatocellular degeneration/necrosis, the moribund condition of these animals was due primarily to test article-related liver toxicity.

Animals given ≥200 mg/kg/day demonstrated two types of test article related clinical observations. These observations consisted of vomitus/emesis, typically immediately after dose administration, and fecal abnormalities (non-formed, liquid, or mucoid), which typically occurred within 1 hour of dose administration. Clinical observations resolved by the following morning. Dose-dependent body weight loss occurred in males given ≥200 mg/kg/day and females given ≥400 mg/kg/day. No test article-related depletion of essential trace elements in plasma (Cr, Co, Cu, Fe, Mg, Mn, Mo, Se, and Zn) was observed in dogs following oral administration of C2E2 at repeated doses up to 600 mg/kg/day for 10 days. Clinical chemistry changes consistent with hepatotoxicity were observed at doses ≥400 mg/kg/day. In the animals that were sacrificed early, these changes included markedly increased aspartate aminotransferase (AST) and alanine aminotransferase (ALT) activity in the male given 600 mg/kg/day and sacrificed on Day 2, and markedly increased ALT activity in the male given 400 mg/kg/day and sacrificed on Day 6. In animals that survived to the scheduled necropsy on Day 11, mildly to moderately increased AST activity was observed on Day 6 in males and females given 600 mg/kg/day, and on Day 11 in males given ≥400 mg/kg/day and females given 600 mg/kg/day. Mildly to markedly increased ALT activity was observed on Days 6 and 11 of the dosing phase in animals given ≥400 mg/kg/day.

Test article-related decreased absolute and relative liver/gall bladder weights occurred in females given 600 mg/kg/day and likely correlated with minimal hepatocyte degeneration/necrosis. Both males sacrificed early exhibited slight (400 mg/kg/day) or severe (600 mg/kg/day) hepatocyte degeneration/necrosis (correlated to red to tan discoloration of the liver in the animal given 600 mg/kg/day). In addition, the liver of the animal given 400 mg/kg/day exhibited slight centrilobular congestion/hemorrhage, minimal brown granular pigment, and minimal mixed inflammation. Both animals exhibited minimal (400 mg/kg/day) or slight (600 mg/kg/day) renal tubule cell degeneration/necrosis. The kidney of the animal given 400 mg/kg/day exhibited minimal basophilic tubules. Additional microscopic findings in these animals were noted in various parts of the intestinal tract, stomach, lymph nodes, prostate, thymus, spleen, and gut-associated lymphoid tissue.

At the terminal sacrifice, test article-related microscopic findings were present in the liver, kidney, and various segments of the intestinal tract. Hepatocyte degeneration/necrosis and mixed cell inflammation occurred in males given ≥200 mg/kg/day. In females, hepatocyte degeneration/necrosis was present at 600 mg/kg/day and mixed cell inflammation was present at ≥400 mg/kg/day. Both females given 600 mg/kg/day had centrilobular congestion/hemorrhage, and several males and females had accumulations of pigment similar to that described in the unscheduled deaths. The male given 600 mg/kg/day had a single thrombosed blood vessel within the hepatic parenchyma. Based on minimal severity and lack of correlative differences in clinical pathology parameters, the liver findings in the male given 200 mg/kg/day were not considered adverse; all other microscopic liver findings in males given 400 or 600 mg/kg/day and females given 600 mg/kg/day were considered adverse.

In the kidney, tubule cell degeneration/necrosis was present in one female given 600 mg/kg/day and one female given 400 mg/kg/day; however, this finding was not present in males at the terminal sacrifice, but was noted in both males sacrificed early. Due to the severity of the findings, these were considered adverse. Test article-related findings in various segments of the intestinal tract included crypt/gland abscess, infiltrates of neutrophils, congestion, and/or depletion/necrosis of lymphocytes of the GALT in one or more animals given ≥200 mg/kg/day. Since these findings were sporadic, of minimal severity, and possibly related to stress, they were not considered adverse.

Exposure to C2E2 increased with increased C2E2 dose level from 60 to 600 mg/kg/day. The increases in mean $C_{max}$ and $AUC_{0-24}$ values were not consistently dose proportional. Sex differences were generally less than 2-fold in C2E2 mean $C_{max}$ and $AUC_{0-24}$ values. No accumulation of C2E2 was observed after multiple dosing of C2E2 in dogs. Ratios of C2E1, DTPA, and C2E3 $AUC_{0-24}$ values compared to that of C2E2 indicated that systemic exposure of C2E1, DTPA, and C2E3 were very low relative to C2E2 (<1%). Daily administration of C2E2 to purebred beagle dogs by oral gavage for 10 days at dose levels of 60, 200, 400, and 600 mg/kg/day resulted in the early sacrifice of one male given 600 mg/kg/day and one male given 400 mg/kg/day due to body weight loss and declining health. Due to early sacrifices, the dose levels of 400 and 600 mg/kg/day exceeded the maximum-tolerated dose. The liver and kidney were identified as target organs of toxicity at ≥400 mg/kg/day. Based on these findings, the no observed adverse effect level (NOAEL) is 200 mg/kg/day. After 10 days of dosing, administration of 200 mg/kg/day C2E2 corresponded to mean C2E2 $C_{max}$ values of 59,450 and 71,950 ng/mL and C2E2 $AUC_{0-24}$ values of 150,727 and 183,760 ng·hr/mL for males and females, respectively.

Example 2

The efficacy of C2E2 of Lot 050 obtained using Method 2 was evaluated in male and female beagle dogs administered a nitrate complex of americium-241 ($^{241}$Am) via inhalation (INH). C2E2 was administered 24 hours post $^{241}$Am inhalation exposure. Animals were monitored and urine and feces were collected daily. Cages were rinsed daily. Animals were euthanized 14 days later and tissues collected. Tissues were processed and analyzed for $^{241}$Am content. The in-life measurements and biokinetics of $^{241}$Am with and without chelation treatment are described.

Sixteen (16) male and female beagle dogs underwent a 14-day quarantine period for acclimation. Once released from quarantine, animals were weighed and that weight was used to randomize the animals into the study. Dogs were 13.3±2.2 months of age at study initiation and weighed 8.9±1.2 kg. After randomization, the animals were acclimated to metabolism cages for approximately 24 hours prior to radionuclide inhalation administration of $^{241}$Am(III)-nitrate at time 0 followed by oral gavage administration of vehicle (water) or 100, 300, or 500 mg/kg C2E2 at 24 hours post inhalation exposure. Animals were placed in metabolism cages for the duration of the in-life phase.

Animals were euthanized 14 days after administration of $^{241}$Am. A full necropsy was conducted and liver, spleen, kidneys, lungs and trachea, muscle samples (right and left quadriceps), GI tract (stomach and esophagus, upper and lower intestine), gonads, two femurs, lumbar vertebrae (L1-L4), paws and tail, TBLN, and all soft tissue remains were collected. The brain and eyes were removed from the skull and combined with the soft tissue remains. The skeleton was defleshed and all bone samples collected for analysis. Pelt was not analyzed for $^{241}$Am content.

Urine, feces, cage rinse, and all tissue samples were processed by heat and chemical treatments. The samples were analyzed by gamma pulse height analysis.

Therapeutic C2E2 was successfully evaluated for decorporation efficacy in beagle dogs exposed by inhalation to $^{241}$Am as a relatively soluble nitrate. Urinary and fecal elimination profiles as well as tissue burdens compared to controls confirmed that the three therapeutic dose levels decorporated $^{241}$Am when administered 24 hours after radionuclide administration. The content of $^{241}$Am in soft tissues and bone was also reduced significantly as a result of the decorporation therapy.

For the study, stock C2E2 (L/N: 020WJL050) was obtained as a white powder and stored at 2-8° C. The C2E2 was weighed out and dissolved in vehicle, DI water. Solutions were prepared at 20 mg/mL, 60 mg/mL, and 100 mg/mL on each day of dosing. The formulation was protected from light by wrapping the container in aluminum foil. Metal-free spatulas, glassware, and stir bars were used when weighing and preparing the formulation.

Americium-241 was obtained from the Department of Energy; it was processed and formulated as a stock solution as a nitrate complex. An aliquot of 20 mCi of the nitrate complex was taken to dryness on a medium temperature hotplate. One hundred milliliters of 0.25M nitric acid was added. The pH was determined to be 0.74. An aliquot was collected and analyzed by gamma pulse height analysis. The final concentration of the formulation was 201.1 µCi/mL.

Eight (8) male and eight (8) female beagle dogs were ordered from Covance Laboratories for study assignment. Sixteen (16) animals were assigned to one of four study groups by body weight stratification and randomization. Dogs were 13.3±2.2 months of age at study initiation and weighed 8.8±1.2 kg. Study animals were conditioned to their metabolism cages for 24 hours prior to $^{241}$Am administration. Observations were conducted to ensure that animals were aware of food and water locations as well as were excreting normal amounts of urine and feces. Animals were uniquely identified with study groups by ear tattoo. In addition, each cage contained color-coded cage cards with the study-specific ID on it.

On the morning of exposure, animals were fasted and sedated with acepromazine (0.05 mg/kg) by intramuscular administration. Dogs were anesthetized with isoflurane (5%). A latex mask was placed over the muzzle to minimize external contamination of the dog. The latex-covered muzzle was placed into the exposure plenum where a mixture of oxygen and isoflurane were continuously flowing and being monitored. Oxygen in the box was maintained at 45-55% and isoflurane was delivered as needed (2-3% in oxygen) to ensure the dog remained anesthetized. Aerosols were generated from the $^{241}$Am nitrate solution using a Hospitec nebulizer operated at 10 psi. The aerosol was transited through a tube furnace operating at 70-80° C. to dry the aerosol and minimize the amount of acid present.

The exhaust flow was 12.2 L/min. Aerosols were collected on Pallflex® FiberFilm™ filters at a flow rate of 0.49 L/min for filter samples and 1.95 L/min for cascade impactor samples. Filters were placed in 20-mL vials with 5 mL of 7N HNO$_3$ and vortexed for 30 seconds. The filters were removed and placed singly into another 20-mL vial. A 50-4 aliquot was removed from the original vial. The filter and the aliquot were individually analyzed for $^{241}$Am and the amount collected on the filter was determined. The aerosol concentration was determined to be 1155±223 nCi/L. The particle size was determined to be 0.63 μm AMAD (activity median aerodynamic diameter) with a 1.72 geometric standard deviation (GSD). Animals were exposed for 8 minutes. At the conclusion of each exposure, the animals were removed from the exposure box, placed in a transport box and returned to their metabolism cages. The target deposited activity in the respiratory tract was 3 μCi.

Twenty-four (24) hours post radionuclide administration, animals were administered test article (or vehicle) by oral gavage as outlined in Table 9. Animals received a single dose of test article (or vehicle) one day following americium exposure. The animal was manually restrained and an appropriately sized feeding tube was inserted into the esophagus. The therapeutic was delivered through the tube (33-52 mL) to achieve the desired mass-normalized dosage of C2E2. Control dogs were administered 45 mL of DI water. One (1) mL of water was flushed through the feeding tube to ensure complete delivery of test article. The animal was returned to its metabolism cage after every dose administration. A study schedule is shown in Table 9.

TABLE 9

Experimental design $^{241}$Am, test articles and necropsy.

| Exposure Group | N | Gender | Test Article | Test Article Dose (mg/kg) | Dose Regimen | Necropsy Day |
|---|---|---|---|---|---|---|
| 1001-1002, | 2 | M | Water | n/a | Day 1 | Day 14 |
| 1003-1004 | 2 | F | | | | |
| 2001-2002, | 2 | M | C2E2 | 100 | Day 1 | Day 14 |
| 2003-2004 | 2 | F | | | | |
| 3001-3002, | 2 | M | C2E2 | 300 | Day 1 | Day 14 |
| 3003-3004 | 2 | F | | | | |
| 4001-4002, | 2 | M | C2E2 | 500 | Day 1 | Day 14 |
| 4003-4006 | 2 | F | | | | |

Upon confirmation of euthanasia, each dog underwent a full necropsy. Tissues collected included: liver, spleen, kidneys, lungs and trachea, muscle sample (right and left quadriceps), GI tract plus contents (stomach and esophagus, upper and lower intestine), gonads, two femurs, lumbar vertebrae (L1-L4), paws and tail, tracheobronchial lymph nodes (TBLN), and all soft tissue remains. The brain and eyes were removed from the skull and combined with the soft tissue remains. The skeleton was defleshed and all bone samples collected for analysis. All tissue samples were placed into appropriately sized and labeled specimen containers with the exception of the pelt, which was not analyzed for $^{241}$Am.

All biological and cage-rinse samples (except pelt) were analyzed by gamma pulse height analysis. Prior to tissue-dependent analysis, samples were thermally and chemically processed by sample-specific methods. After samples were prepared they were placed into 20-mL liquid scintillation vials and counted on the gamma counter (Perkin Elmer, 2480 Wizard2 Gamma Counter).

Mean and standard deviation of the body weights collected for randomization and exposure data were performed using Microsoft Excel. Statistical analysis was conducted by one-way analysis of variance (ANOVA) used to evaluate the pattern of recovered doses. For each sample type, differences between untreated controls and treated groups were assessed with individual F-tests based on the ANOVA's pooled estimate of underlying between-animal variance. Absence of significant statistical evidence of a difference in the pattern response across genders ($p>0.05$) accompanied by significant ($p<0.05$) evidence of overall differences between genders provides evidence of constant shift in response between genders, irrespective of treatment.

The in-life portion of the study was accomplished without incident. The majority of animals had no unusual or adverse effects related to the study; this includes vomiting from the C2E2 dose administrations. However, it was noted that one animal from the high level C2E2 dose group (Animal 4004) had foamy emesis in the cage pan after gavage dosing. Thus the fidelity of dose retention in this animal cannot be assured.

Table 10 summarizes the total activity of $^{241}$Am recovered for the four experimental groups in this study. Group 4 recovered less material than the remaining groups but this was largely due to a single outlier (4003) that received less than a total of 1000 nCi. The reason for the low activity in this animal is unknown. All records show that there was no issue with processing of samples, no vomiting on study, the aerosol concentration was on target, and the animal did not wake during exposures. The only notable finding is that this dog weighed only 6.5 kg and was the smallest animal on study but this alone does not account for the low activity received. If this animal is removed from the group average, the group average increases to 1940 which is similar to the average from group 1 animals. For this study, animals received an average of 2220 nCi±610 total deposited activity. Unlike wound or IV studies, fractional recoveries cannot be calculated with inhalation exposures because the actual delivered activity of $^{241}$Am to the respiratory tract can only be reconstructed based on aerosol concentration data together with physiological measurements or radiochemical measurement data. The estimated deposited activity is given by the equation:

Deposited Activity=Aerosol Concentration (AC)*Respiratory Minute Volume (RMV)*Deposition Fraction (DF)*Exposure Duration (ED)

Where: AC=dog's aerosol conc (nCi/L); RMV=0.499*Body Weight^(0.809); DF=10%; ED=8 min The estimated delivered activity for the study was 2770 nCi for females and 2580 nCi for males. The delivered activity was approximately 11 percent lower than the desired activity, which is well within the uncertainties of the exposure procedure. The deposition fraction for the parenchymal region of the lung is variable based on aerosol characteristics (particle size and $\sigma_g$) and breathing patterns and may vary from the assumed 10%.

TABLE 10

Group recovered doses.

| Exposure Group | Recovered Activity (nCi ± SD) |
|---|---|
| 1001-1004 | 2020 ± 620 |
| 2001-2004 | 2430 ± 280 |
| 3001-3004 | 2720 ± 560 |
| 4001-4004 | 1700 ± 550 |

Figure 23A:
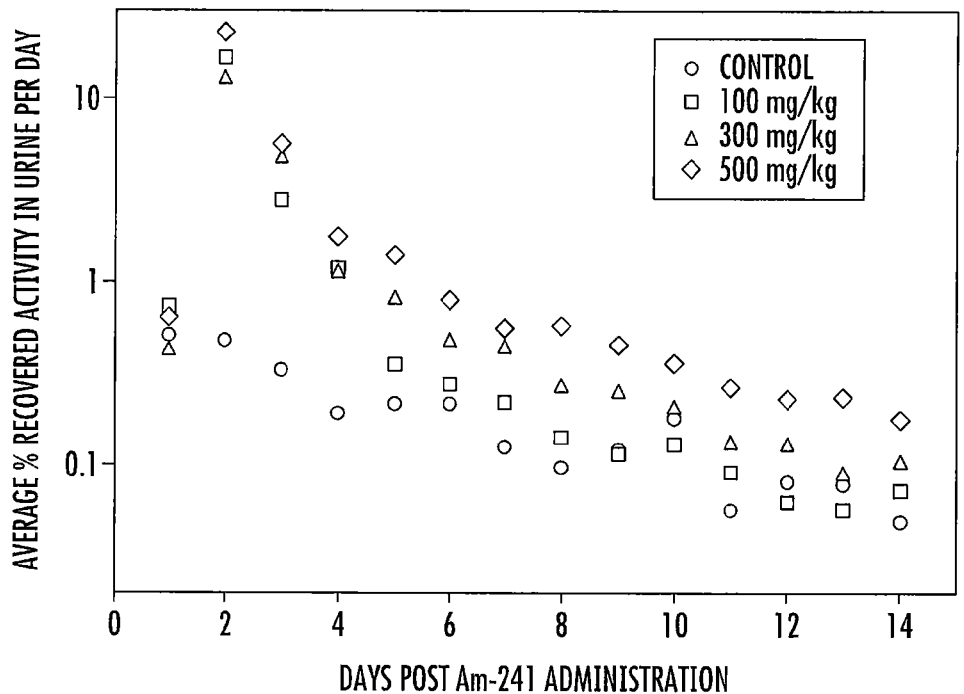
Figure 23B:
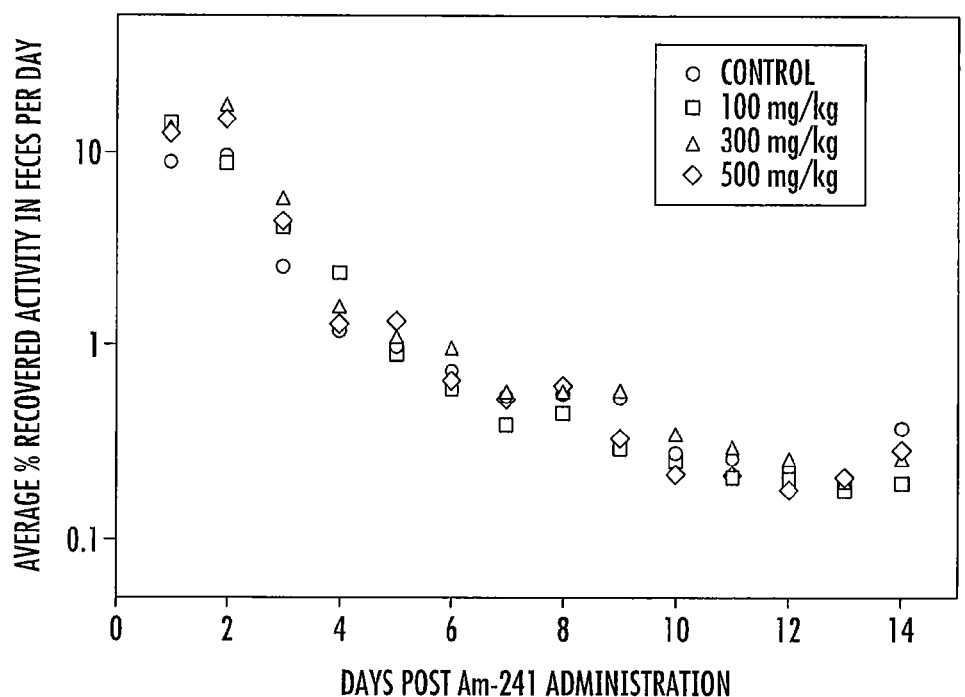

FIGS. 23A and 23B show the daily urinary and fecal elimination of $^{241}$Am for all study groups. Statistical analysis has not been conducted on the daily collections. Results are expressed as fraction of the total recovered $^{241}$Am activity. All C2E2 dose groups displayed a dose-dependent increase in urinary excretion compared to the untreated controls. The urinary excretion of the dose groups was maintained through the duration of the study. Fecal elimination was modestly increased for all dose groups through the first 3 days post exposure when the levels of elimination returned to control levels.

Figure 24A:
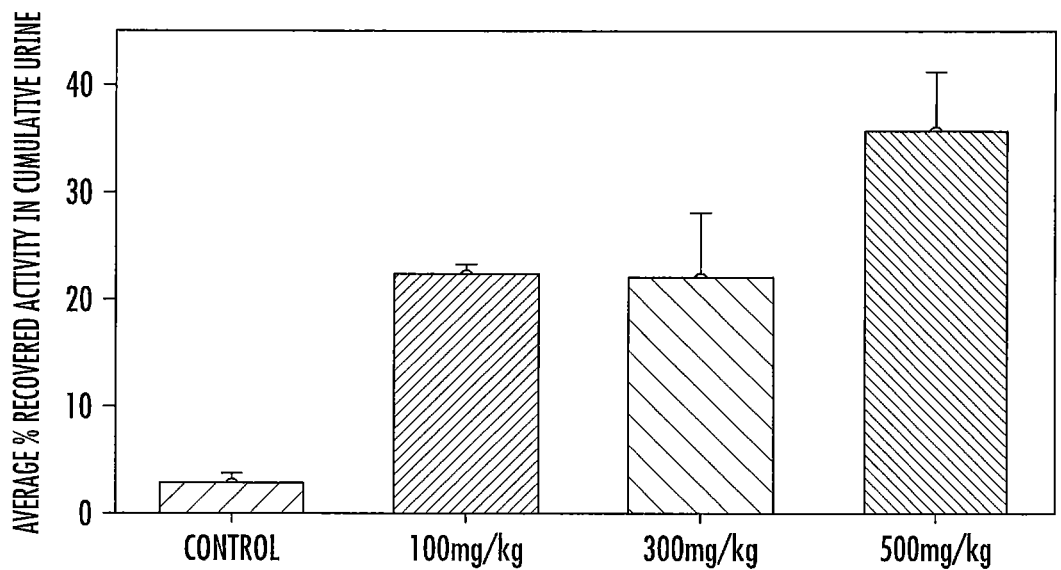
Figure 24B:
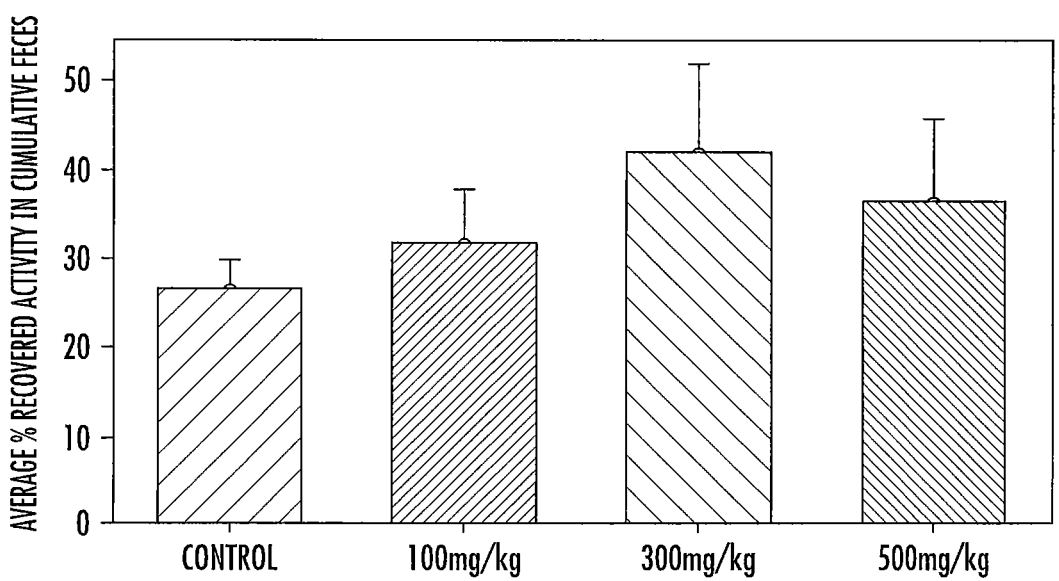
Figure 25A:
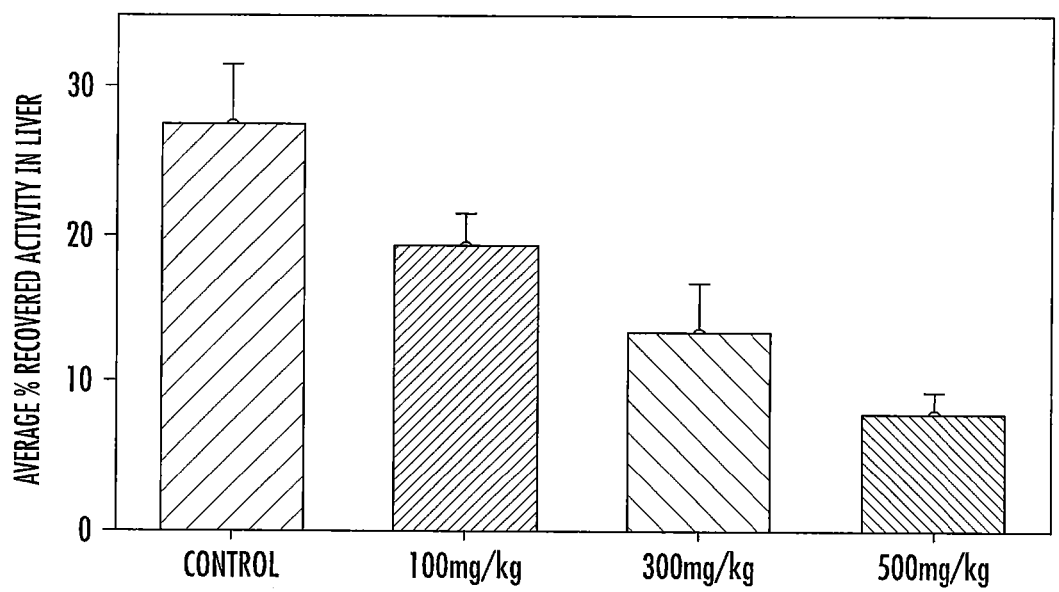
Figure 25B:
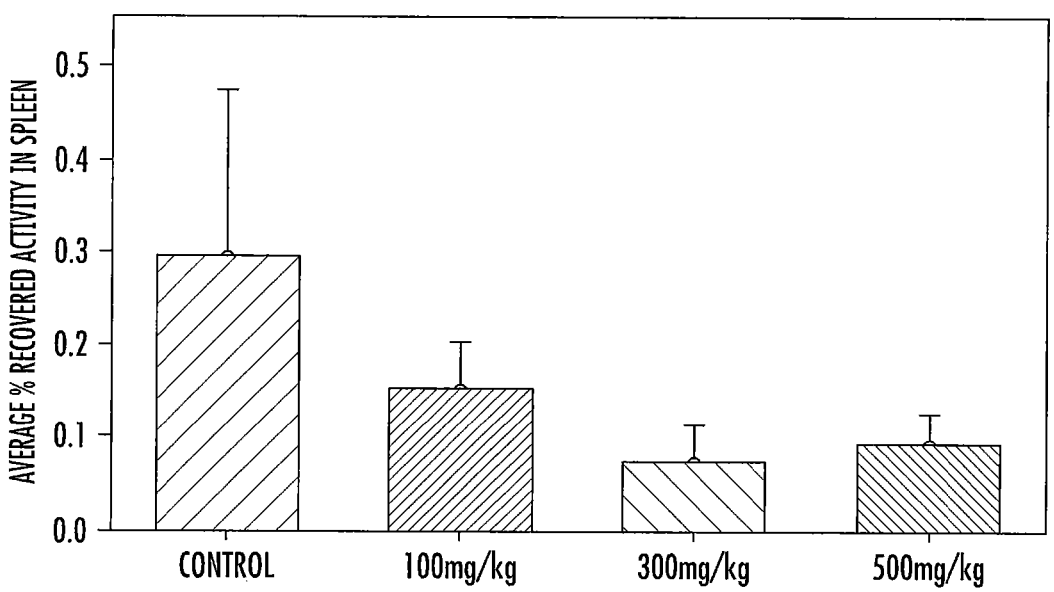
Figure 25C:
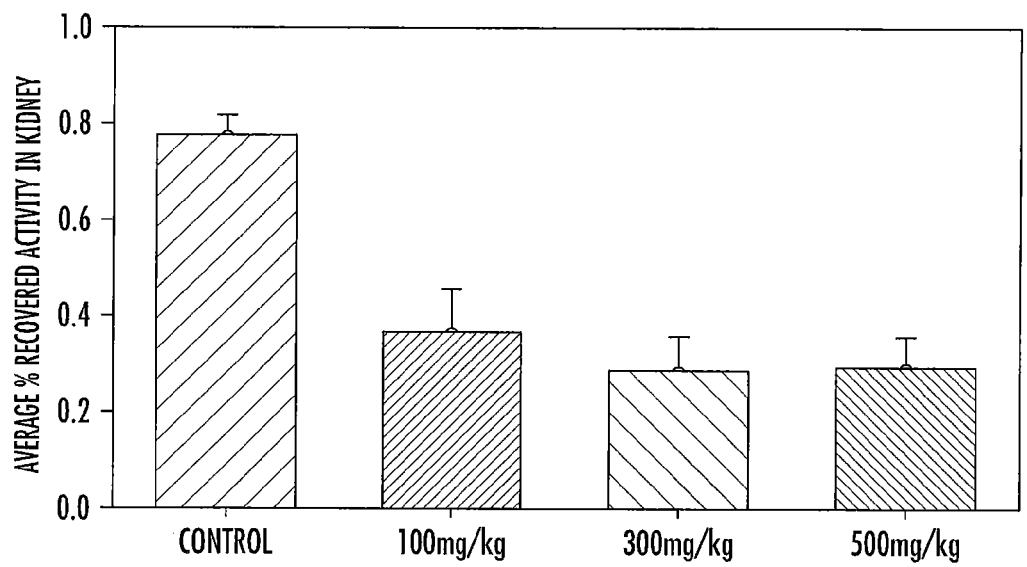
Figure 25D:
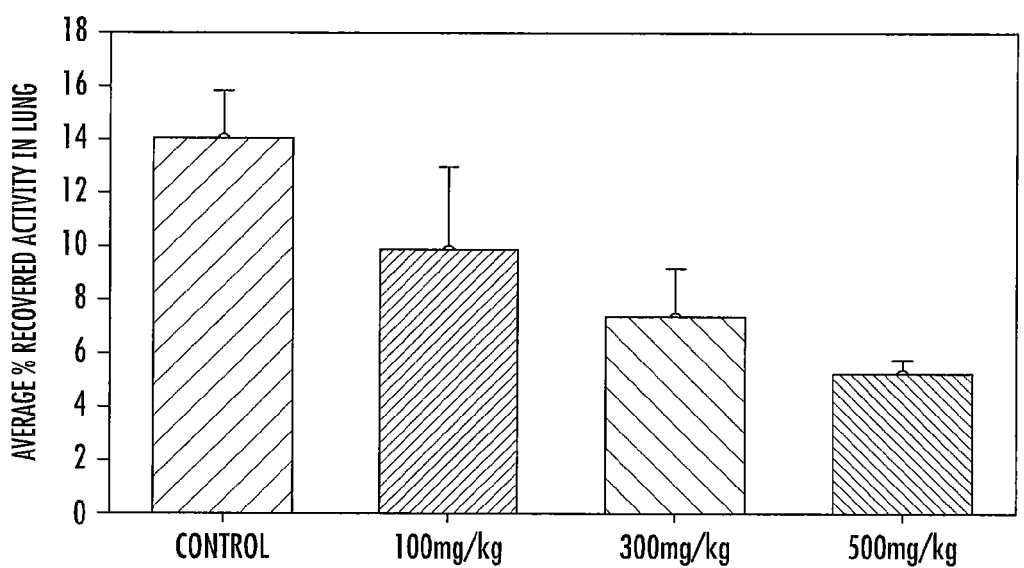
Figure 26A:
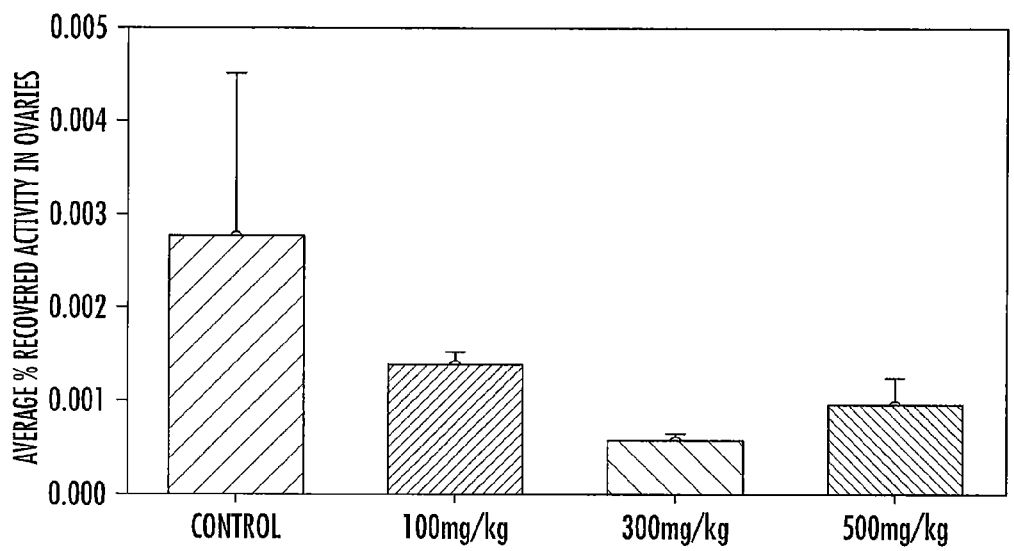
Figure 26B:
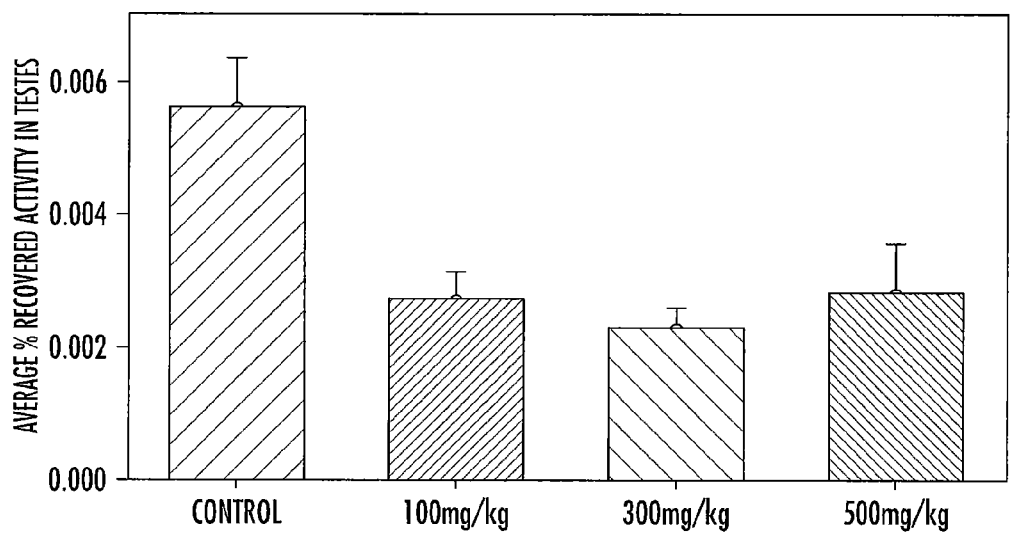
Figure 26C:
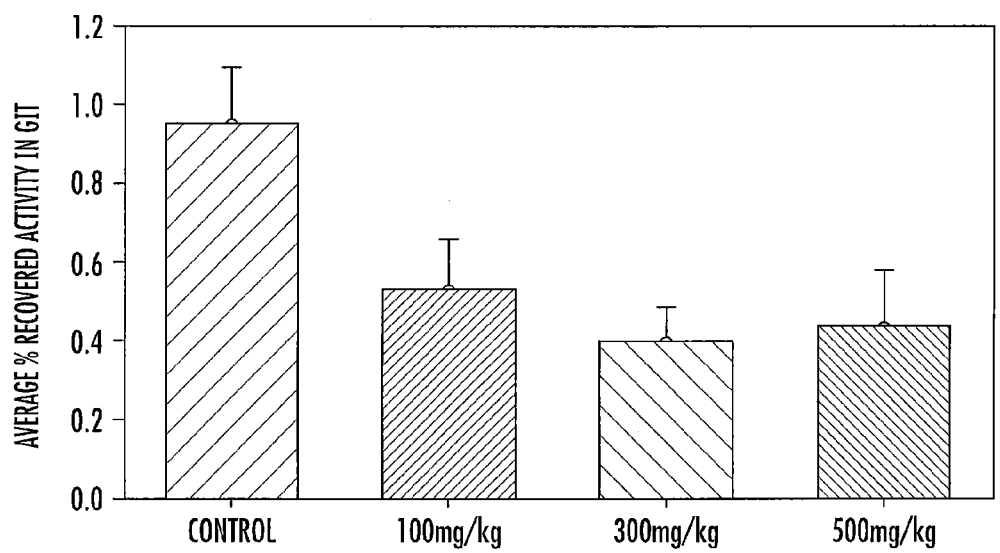
Figure 26D:
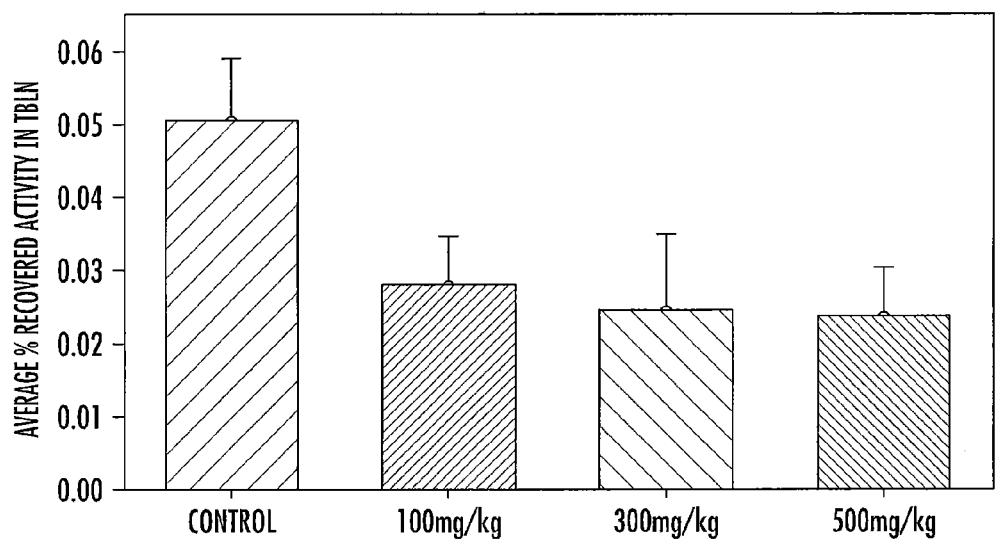
Figure 26E:
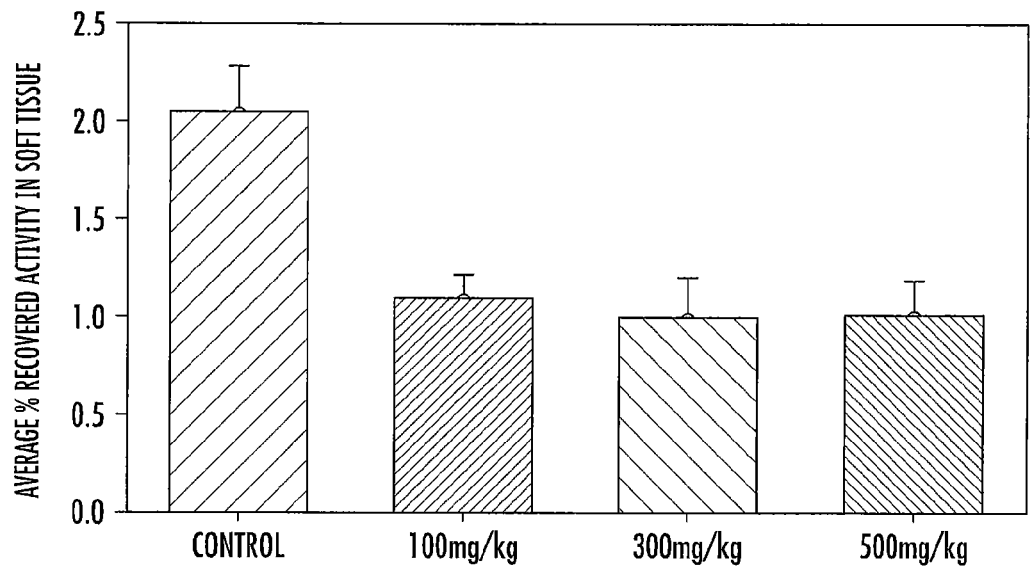
Figure 26F:
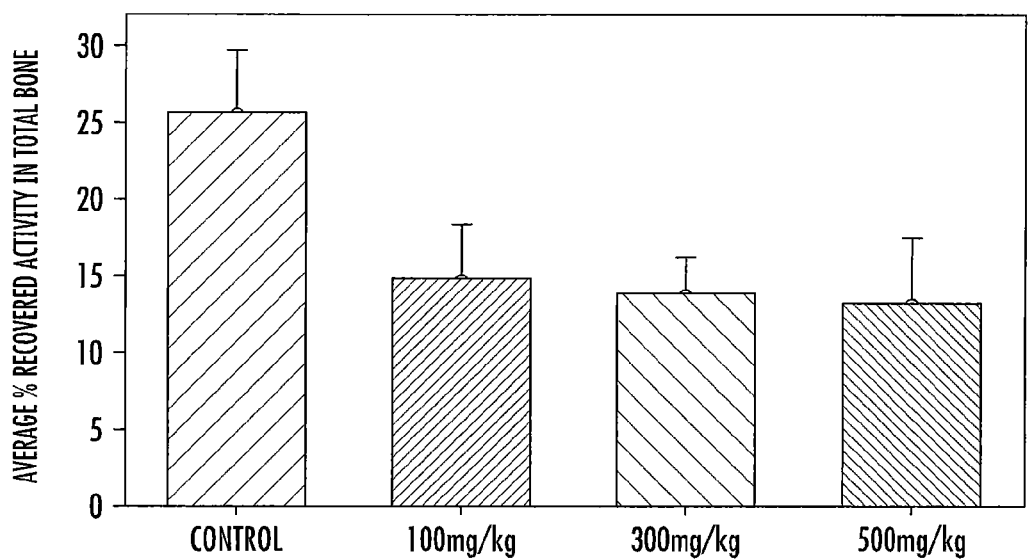

FIGS. 24A and 24B and Table 11 show the cumulative urine and cumulative feces eliminations for all experimental groups. Treatment with all doses of C2E2 resulted in a statistically significant increase of cumulative activity in urinary excretion compared to the untreated control group. The 500 mg/kg dose resulted in a higher urinary elimination of $^{241}$Am compared to the 100 and 300 mg/kg dose groups. Treatment with the mid and high doses of C2E2 resulted in a statistically significant increase of cumulative activity in fecal excretions compared to the untreated control group. Cumulative fecal excretion appeared to increase with increasing doses of C2E2, but the response was not monotonic, i.e., the largest amount of 241Am excreted occurred in the mid-dose group. Nevertheless, the amount of $^{241}$Am excreted in feces was statistically greater than for the control group for the mid- and high-dose treated groups, and elevated (but not statistically significantly different) for the low-dose group.

TABLE 11

Average percent recovered activity.

| | Urine | Feces |
|---|---|---|
| Water | 2.71 (0.29) | 26.53 (1.89) |
| 100 mg/kg C2E2 | 22.35 (0.56)** | 31.78 (3.21) |
| 300 mg/kg C2E2 | 21.93 (2.26)** | 41.85 (4.43)** |
| 500 mg/kg C2E2 | 35.63 (0.70)** | 36.53 (1.18)* |

Mean (SEM);
*p < 0.05 against Control group,
**p < 0.01 against Control group

The terminal contents of $^{241}$Am in the various tissues analyzed are shown graphically for all experimental groups in FIGS. 25A-D and 26A-F, and numerically in Tables 12 and 13. All results are expressed as percentage of the total recovered $^{241}$Am activity. FIGS. 25A-D show tissue contents for liver, spleen, kidney, and lung for each dosing group. All three C2E2 groups had statistically significant reductions in liver, kidney and lung burdens. Little dose response was noted in the remaining spleen and kidney burden between the mid and high dose groups.

TABLE 12

Average percent recovered activity.

| Group | Liver | Spleen | Kidney | Lung |
|---|---|---|---|---|
| Water | 27.20 (2.01) | 0.30 (0.09) | 0.77 (0.01) | 13.98 (0.91) |
| 100 mg/kg C2E2 | 19.13 (1.34)** | 0.16 (0.03) | 0.37 (0.03)** | 9.69 (1.77)* |
| 300 mg/kg C2E2 | 13.35 (1.51)** | 0.07 (0.02)** | 0.28 (0.04)** | 7.23 (0.89)** |
| 500 mg/kg C2E2 | 7.71 (0.35)** | 0.09 (0.02)* | 0.29 (0.01)** | 5.10 (0.31)** |

Mean (SEM);
*p < 0.05 against Control group,
**p < 0.01 against Control group

TABLE 13

Average percent recovered activity.

| | GIT | Testes | Ovaries | TBLN | Soft Tissue | Total Bone |
|---|---|---|---|---|---|---|
| Water | 0.95 (0.09) | 0.006 (0.001) | 0.003 (0.001) | 0.035 (0.006) | 2.05(0.12) | 25.50 (2.16) |
| 100 mg/kg C2E2 | 0.53 (0.05)** | 0.003 (0.001)* | 0.001 (0.000) | 0.028 (0.002) | 1.08 (0.07)** | 14.90 (1.97)** |
| 300 mg/kg C2E2 | 0.39 (0.06)** | 0.003 (0.001)* | 0.001 (0.001)* | 0.024 (0.004) | 0.99 (0.12)** | 13.93 (1.30)** |
| 500 mg/kg C2E2 | 0.44 (0.05)** | 0.003 (0.001)* | 0.001 (0.000) | 0.023 (0.003) | 1.01 (0.02)** | 13.20 (0.86)** |

Mean (SEM): *p < 0.05 against Control group, **p < 0.01 against Control group

FIGS. 26A-F show terminal tissue contents for ovaries, testes, GIT, TBLN, soft tissue, and total bone for each dosing group compared with controls. In ovaries, 241Am contents for all dose groups were reduced compared to the untreated control group. In testes, all treated groups showed statistically significant reductions in $^{241}$Am content compared to untreated controls. There were no dose-dependent patterns indicated for the ovary or testes. This may be attributed to the small amounts of $^{241}$Am present in the tissues. GIT (including contents) and soft tissue $^{241}$Am content both displayed statistically significant but not dose-dependent tissue reductions compared to controls. About 50% and 40% reductions of $^{241}$Am content were observed for TBLN and total bone content, respectively. There was also a suggestion of a dose-dependent decrease in terminal content of $^{241}$Am, but the trend was not a strong one.

Table 14 shows the percentage tissue content reduction compared to the untreated control group and Table 15 is the percentage of urinary enhancement or fecal reduction compared to the untreated control group. The high-dose group showed >65% decrease in liver and spleen, >50% decrease in kidney, lung, GIT, gonad, and soft tissue burdens, and >30% decrease in TBLN and total bone content compared to untreated controls. The mid-dose treatment group showed a >60% decrease in spleen, kidney, and gonad burdens, >45% decrease in liver, lung, GIT, soft tissue and total bone, and >30% decrease in TBLN. The low treatment group showed >40% decreases in spleen, kidney, GIT, gonads, soft tissue, and total bone burdens and >20% decreases in liver, lungs, and TBLN burdens.

TABLE 14

Percent $^{41}$Am content reduction in tissue.

|  | Liver | Spleen | Kidneys | Lungs | GIT | Gonads | TBLN | Soft Tissue | Total Bone |
|---|---|---|---|---|---|---|---|---|---|
| 100 mg/kg C2E2 | 29.7 | 47.7 | 52.4 | 30.6 | 43.9 | 51.1 | 22.9 | 47.1 | 41.6 |
| 300 mg/kg C2E2 | 51.0 | 74.8 | 63.0 | 48.2 | 58.2 | 66.3 | 31.7 | 51.8 | 45.5 |
| 500 mg/kg C2E2 | 71.7 | 69.0 | 61.8 | 63.5 | 54.1 | 55.3 | 35.0 | 50.7 | 48.3 |

TABLE 15

Percent change in excretion.

|  | Feces | Urine |
|---|---|---|
| 100 mg/kg C2E2 | 115 | 820 |
| 300 mg/kg C2E2 | 155 | 805 |
| 500 mg/kg C2E2 | 135 | 1310 |

Urinary output increased over 800% for the low and mid dose groups and 1300% for the high dose group compared to untreated controls. Fecal output increased over 110% for the low and high dose groups, and 150% for the mid dose group.

Urinary elimination profiles as well as tissue burdens compared to controls confirmed that the three therapeutic dose levels decorporated $^{241}$Am when administered 24 hours after radionuclide administration, and in many cases in a dose-dependent manner. The high-dose group of C2E2 decorporated $^{241}$Am more efficiently than the low-dose group. Future dose administrations will focus on the higher levels of administered C2E2, although, while not wishing to be bound to any particular theory, it is speculated that the modest increases in dose-dependent efficacy may be compensated effectively by multiple administrations of C2E2, much as is done with DTPA therapy.

Example 3

The solubility of C2E2 of Lot 050 obtained using Method 2 was initially determined to be 100 mg/mL. However, dosing solutions prepared at this concentration exhibited precipitation over time. The aim of this study was to understand the process behind the initial super-saturation and subsequent precipitation and to determine the solubility of C2E2.

A precipitation study was performed to estimate the concentration at which no precipitation occurs. Initially, 12 samples of C2E2 were prepared at concentrations ranging from 40-150 mg/mL in pH 3.0 buffer in steps of 10 mg/mL. The solutions were left to stir until precipitation occurred.

Three samples of C2E2 at 60, 70 and 100 mg/mL in pH 3.0 buffer were prepared and stirred at room temperature. At 0.083, 5, 1, 2, 4, 6, 20, 24 and 44 hours 0.5 mL samples were withdrawn centrifuged at 14,000×g and the concentration of supernatant measured by HPLC-CAD. At each time-point the pH of the supernatant was also measured.

Figure 27:
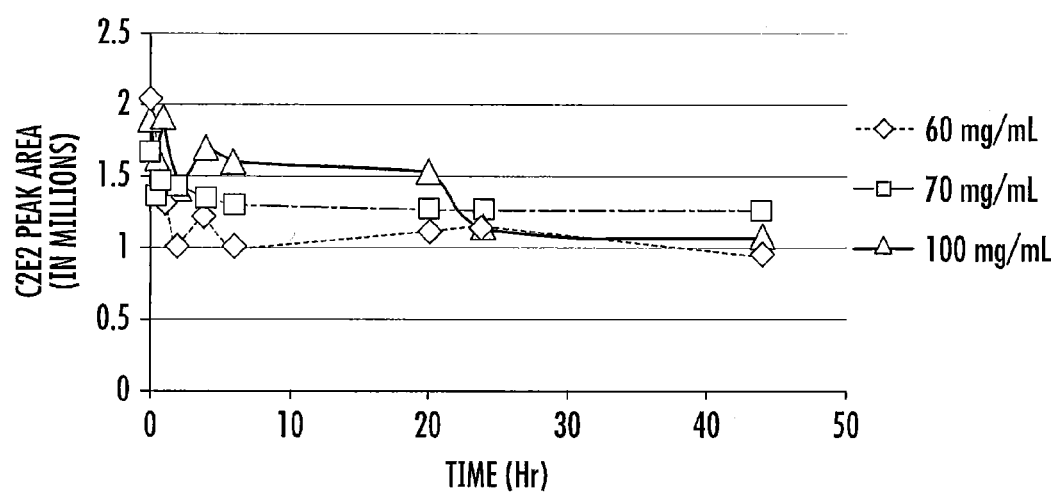

After 24 hours, precipitation was observed in solutions with C2E2 concentrations above 90 mg/mL. Precipitation was observed in solutions with C2E2 at concentrations above 60 mg/mL that were left to stand at room temperature with no stirring for 48 hours after 24 hours with stirring. The solubility of C2E2 at pH 3.0 is between 60 and 70 mg/mL. In the second part of the study, C2E2 at concentrations just above and below the determined solubility and a third sample at a higher concentration were prepared to test whether C2E2 precipitation resulted in lower equilibrium solubility. The concentration time profile achieved is shown in FIG. 27. Solutions of C2E2 prepared at 60 and 70 mg/mL solutions were stable after 6 hours and the 70 mg/ml sample was at a higher concentration than the 60 mg/ml solution. Some precipitation of the 70 mg/ml was observed before the end of the study, so the concentration shown by the line with the ■ symbols for the 70 mg/mL solution is the equilibrium solubility. For the concentration of the 100 mg/ml solution, C2E2 remained in a supersaturated solution for 20 hours and then suddenly precipitated out of solution between 20-24 hours, with the final solubility in the range of the 60 and 70 mg/mL C2E2 solutions. The sudden change in concentration may indicate the formation of another polymorph. The centrifuged solid was separated from the supernatant and analysis by DSC will be performed.

Based on observation of dosing solutions, after a certain amount of time precipitation occurred in the C2E2 solutions accompanied by a lower measured solubility of C2E2.

Example 4

Metabolism of C2E2 by esterases in plasma may cause the loss of the ester pro-moieties in C2E2. Ex vivo degradation of C2E2 in plasma, if present, would have implications for the interpretation of C2E2 efficacy data and for the analysis of data from PK and TK studies; continued metabolism of the compound after blood samples have been collected would result in the inaccurate calculation of PK parameters. Therefore, the aim of this study was to determine the stability of C2E2 in plasma.

Prior to the study, 975 µL of plasma (Rat, Beagle and Human) was preheated to 37° C. in Eppendorff tubes and the test compound (C2E2) was prepared in DI water (10 mg/mL). The C2E2 was from Lot 050 obtained using Method 2. To initiate the study, 25 µL of the C2E2 solution was added to the pre-heated plasma and briefly vortexed, to mix. At 0, 15, 30, 60 and 120 minutes a 100 µL sample of plasma was taken, an equal volume of cold acetonitrile was added and mixed to precipitate plasma proteins. Samples were centrifuged at 4° C. and 14,000×g for 10 minutes to remove precipitated proteins, the supernatant was collected and the C2E2 concentration determined by HPLC-CAD. All conditions were repeated in triplicate. Diltiazem was used as a positive control compound, and heat-inactivated plasma was used as a negative control.

HPLC Detection Methods: C2E2 analysis was performed on a prominence HPLC (Shimadzu Corporation, Kyoto, Japan) equipped with a Corona Ultra charged anion detector (CAD) (Thermo scientific, Sunnyvale, Calif.). A reverse phase gradient separation was used with an Alltima C18 column (250×2.1 mm² internal diameter with 5 µm particle size (Grace)) at 40° C. and a flow rate of 0.25 mL/min. The mobile phase is composed of water with 0.1% trifluoroacetic acid (A) and acetonitrile/isopropanol 2:1 (B). The mobile phase follows a linear gradient from 94:6 to 75:25 over 14 min, the gradient then increases for 0.5 min to achieve a flow of 0:100 for 3.5 minutes followed by re-equilibration of the system at 94:6 for 6 min. The CAD analysis is performed at 25° C. with nitrogen flow at 35.1 psi. For diltiazem, the gradient mobile phase consists of two major components: Mobile Phase A, aqueous TEA (0.2%, v/v) that was pH adjusted to 5.0 with o-PA, and Mobile Phase B, ACN.

The gradient is 0.01-34.99 min: 22% B; 35.00-44.99 min: 33% B; 45.00-60.00 min: 38% B. The flow rate is 1.0 mL/min, a Thermo Hypersil ODS column (150 mm 4.6 mm i.d. with 5.0 µm particles) will be used, injection volume will be 10 µL and column oven temperature maintained at 25° C. Diltiazem will be detected by UV at 240 nm. The limit of quantification is 0.35 µg/mL. (Journal of Pharmaceutical Analysis 2012; 2(3):226-237).

Figure 28A:
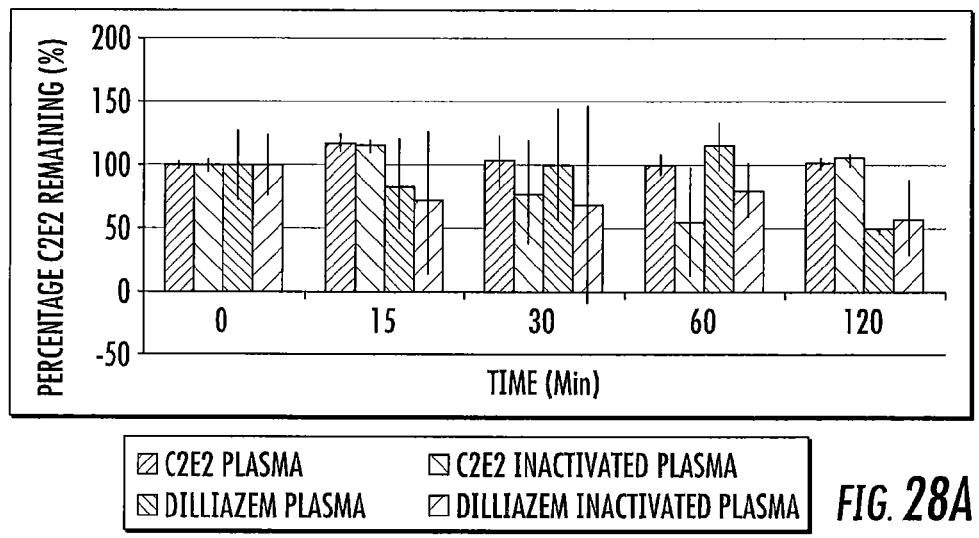
Figure 28B:
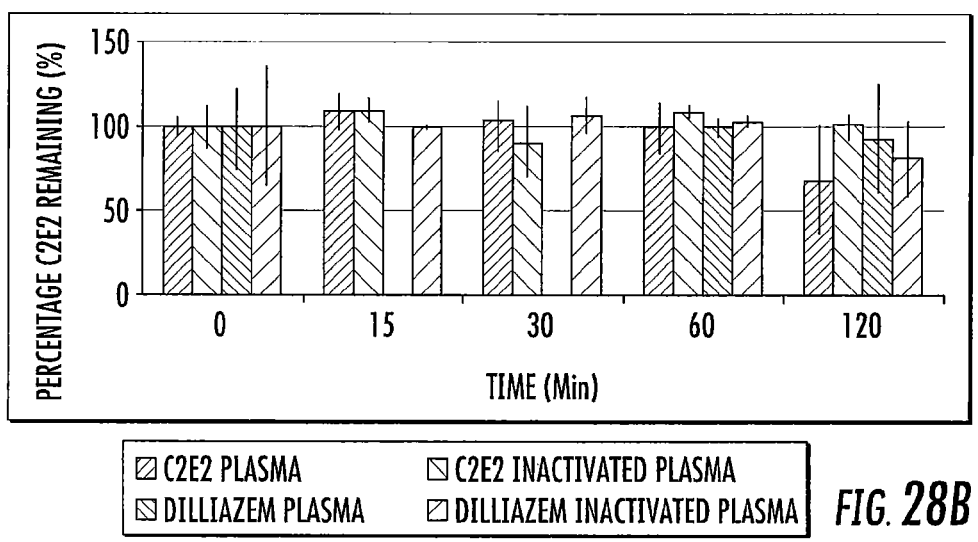
Figure 28C:
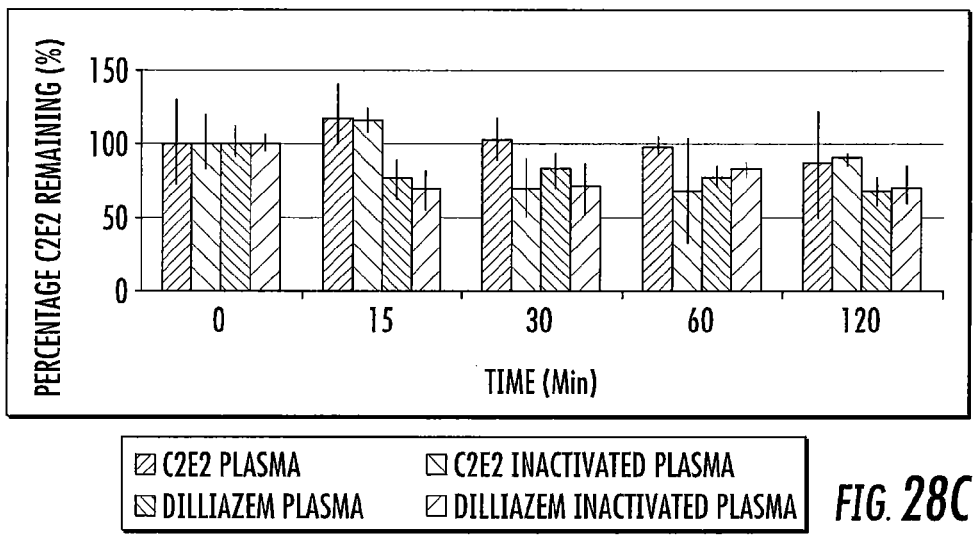

Preliminary results from the study are summarized in FIG. 28A-C. Although some variability was seen, a robust metabolism of the positive control (diltiazem) was observed in all species. In all species tested, C2E2 metabolism was minimal or not detected for at least two hours; approximately 90% C2E2 remains after 2 hours in human plasma. As C2E2 does not undergo metabolism, the observation that heat inactivation did not prevent metabolism in the diltiazem positive control does not alter the study conclusions.

Example 5

Preliminary PK/PD modeling predicted that C2E2 efficacy is correlated with AUC. While not wishing to be bound by any particular theory, if the toxicology studies show that toxicity is associated with $C_{max}$ rather than AUC then splitting the dose and administering it more frequently could increase the therapeutic window. To evaluate the benefits of single vs. multiple daily doses of DTPA di-ethyl ester a decorporation study was performed in rats contaminated with $^{241}$Am.

The animal study was conducted according to a protocol approved by The University of North Carolina at Chapel Hill Institutional Animal Care and Use Committee. Sixteen male Sprague Dawley rats were contaminated with $^{241}$Am(NO$_3$)$_3$ (0.25 µCi) by intramuscular injection (0.1 mL, 0.1 M HNO$_3$) into the right hind leg, under isoflurane anesthesia. Immediately after injection, body weights were recorded (Day 0 weight) and animals placed in individual metabolic cages. The 16 rats were assigned to four groups; untreated control, 5 daily oral gavage doses of 600 mg/kg C2E2 once daily, 5 days of oral gavage treatment of 300 mg/kg C2E2 twice daily or 5 daily intravenous doses of Zn-DTPA solution (13.3 mg/kg) via a jugular vein catheter. The C2E2 was from Lot 050 obtained using Method 2. The C2E2 dosing solution utilized was a 10% w/w solution in water. All animals were observed at least once daily for morbidity, mortality, and general appearance. Excreted urine and feces were collected at 2, 4, 8, 10, 12, 14, 18, 20 and 24 hours after the first dose and daily for the remainder of the study. The samples were transferred to 20 mL scintillation vials, weighed and placed in a gamma counter (Wizard2 2480, Perkin Elmer) for detection of $^{241}$Am gamma activity. In addition, following necropsy, selected tissues were removed, weighed and placed in a gamma counter (Wizard2 2480, Perkin Elmer) for detection of $^{241}$Am gamma activity. The total amount of $^{241}$Am administered to the animals was determined by quantifying the 59.7 keV photons emitted by $^{241}$Am in duplicate aliquots (100 µL) of the injection solution using a gamma counter (wizard series, Perkin-Elmer). A counting window from 40-80 keV and a 60-second counting time were used for acquisition and each reading was corrected for background at acquisition. All experimental tissues and samples were counted using the same gamma counter and protocol. For all the samples, $^{241}$Am content was expressed as a percentage of the initial dose. The femur from the leg opposite to the injection site was scaled by a factor of 20 to estimate total skeletal $^{241}$Am burden.

Figure 29:
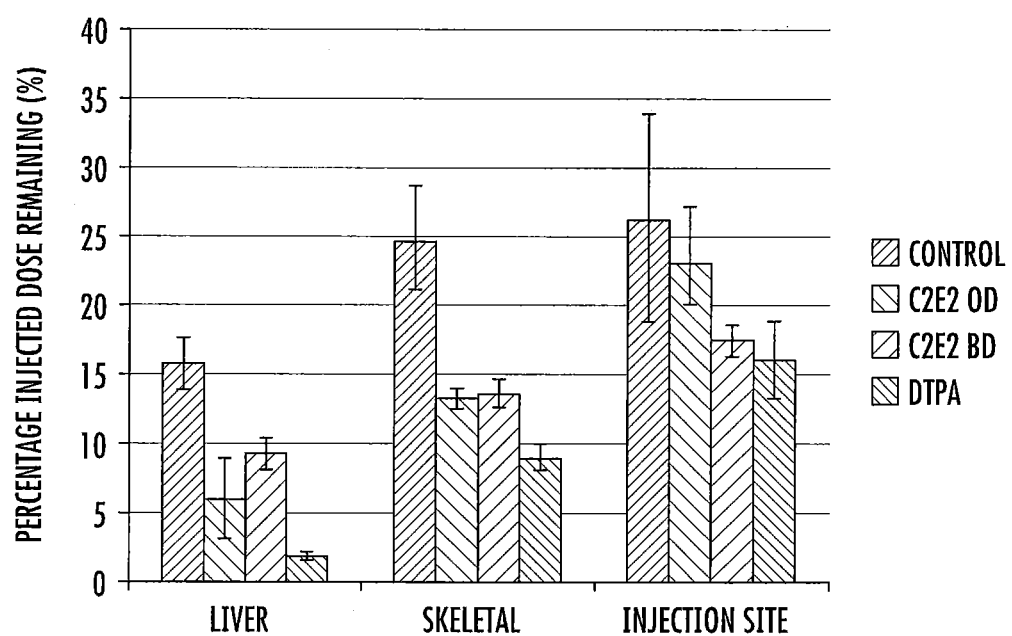

All sixteen male rats completed the study. Preliminary analysis shows that the elimination of americium was significantly enhanced in all treatment groups compared to the untreated control and dividing the C2E2 dosage and giving it twice daily did not significantly alter total decorporation. Table 16 shows the total decorporation in each group and FIG. 29 Error! Reference source not found. shows americium burdens in key target tissues.

TABLE 16

Total decorporation in the seven days after americium contamination

| Group | Total Decorporation (% of injected dose) |
|---|---|
| Untreated Control | 17.7 ± 2.1 |
| Daily C2E2 | 39.7 ± 2.6 |
| Twice Daily C2E2 | 43.6 ± 1.6 |
| i.v. Control | 54.0 ± 3.9 |

Figure 30A:
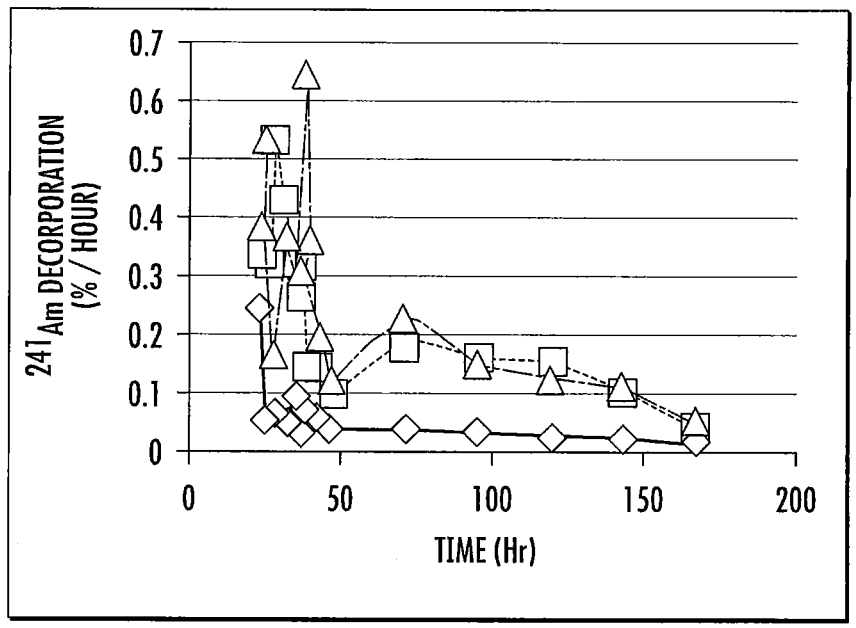
Figure 30B:
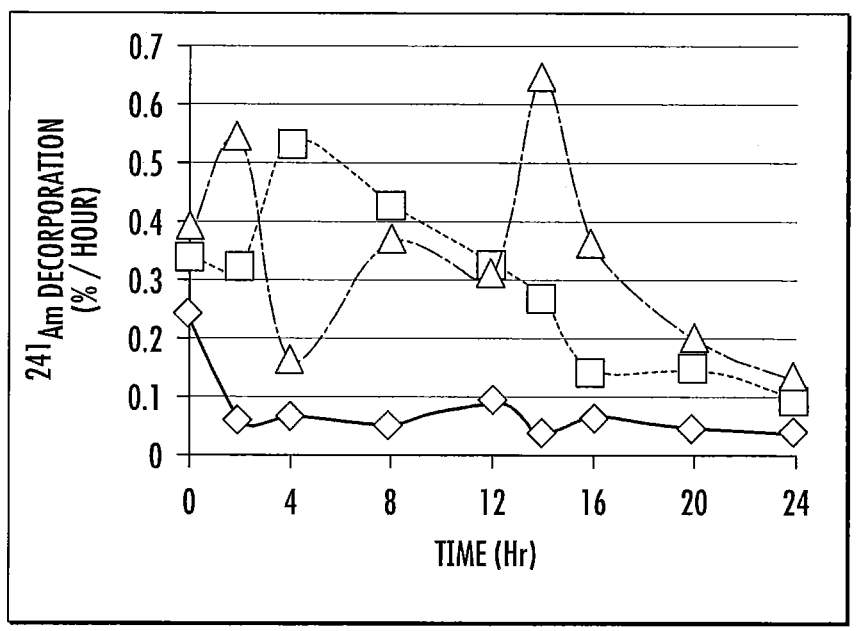

In addition to examining total decorporation and tissue burden, the profile of americium decorporation in urine over time was obtained. FIGS. 30A and 30B show the profiles of urinary decorporation after once and twice daily treatment with C2E2. An increase in decorporation after the second C2E2 dose can be clearly seen in FIG. 30B. The second peak in the twice daily dosing group at around 14 hours results in greater urinary elimination than the first at 2 hours, which may be due to some residual C2E2 from the first dose. However, the time of day and the activity of the animals may also affect the profiles as urine was not manually expressed in this study. Over the course of the study, the once daily (OD) and twice daily (BD) groups resulted in very similar profiles of daily urinary elimination, consistent with the hypothesis that, while not wishing to be bound by any particular theory, drug AUC is the best indicator of efficacy in the rat.

Preliminary analysis of the data suggests that splitting the C2E2 dose into two smaller doses dose not decrease efficacy and therefore may potentially increase the therapeutic window for C2E2. Full analysis will be performed once the female arm of the study is complete.

Example 6

The objective of this study was to evaluate C2E2 for its ability to induce reverse mutations at the histidine locus in *Salmonella typhimurium* tester strains TA98, TA100, TA1535, and TA1537, and at the tryptophan locus of *Escherichia coli* (*E. coli*) strain WP2uvrA in the presence or absence of an exogenous mammalian metabolic activation system (S9).

C2E2 was evaluated in an initial mutagenicity assay in all five tester strains at dose levels of 5.00, 16.0, 50.0, 160, 500, 1600, and 5000 µg/plate with and without S9. C2E2 was from Lot 050 obtained using Method 2. C2E2 was prepared in Cell Culture Grade Water vehicle and formed a transparent colorless solution. Compared to concurrent vehicle controls, reductions in the mean numbers of revertant colonies was noted at the 5000 µg/plate level in TA100, TA1535, TA1537 and WP2uvrA under conditions without S9 and at ≥500 µg/plate in TA1535, TA1537 and WP2uvrA under conditions with S9. Enhanced background lawn growth was observed at 5000 µg/plate with TA1537 in the test without S9. The reductions in the numbers of revertant colonies and the enhanced background lawn growth are indicative of C2E2 treatment-related toxicity. With exception to the enhanced background lawn in TA1537 without S9, all other background lawns in all strains, with and without S9, were normal indicating there was appropriate bacterial growth during treatment to express a mutagenic event. There were no relevant increases in the numbers of revertant colonies observed at any dose level with any strain in the absence or presence of S9 metabolic activation.

All vehicle and positive control values were within acceptable ranges and all criteria for a valid study were met.

These results indicate that C2E2 is negative in the Bacterial Reverse Mutation Assay tested up to 5000 µg/plate with and without S9 and under the conditions of this protocol.

Example 7

The objective of this in vitro assay was to evaluate the ability of C2E2 to induce chromosomal aberrations in cultured Chinese hamster ovary (CHO) cells with and without an exogenous metabolic activation system.

C2E2 was prepared in cell culture grade water (CCGW) and formed a colorless, transparent, solution. The C2E2 was from Lot 050 obtained using Method 2. Subsequent stocks were prepared by serial dilution in vehicle and all treatments were administered into 10 mL cultures in a volume of 10%. Vehicle control cultures were treated with 100 µL/mL per culture. The treatment periods were for 3 hours with and without metabolic activation or approximately 20 hours without metabolic activation.

In an initial chromosomal aberration assay (B1 test), C2E2 concentrations of 6.92, 9.89, 14.1, 20.2, 28.8, 41.2, 58.8, 84.0, 120, 172, 245, 350, and 500 µg/mL were tested in duplicate cultures in the 3- and 20-hour tests without S9 and in the 3-hour test with S9 metabolic activation. All cultures, under all test conditions, were harvested approximately 20 hours from the initiation of treatment. At culture termination, viable cells were counted and population doubling was calculated for measurement of cytotoxicity to support selection of dose levels for aberration analysis. Visual observations of cultures for general cell health and confluence were made prior to termination.

There was no relevant cytotoxicity observed in the 3-hour treatment tests with and without S9 metabolic activation and the 245, 350 and 500 µg/mL dose levels were selected for aberration analysis for each 3-hour test condition. There were no statistically significant or biologically relevant increases in the number of cells with chromosomal aberrations observed at any dose level examined in either 3-hour test under conditions with or without S9 metabolic activation.

In the 20-hour test without S9, a treatment-related decreasing trend in cytotoxicty was shown by population doubling calculations. The 20.2, 172 and 500 µg/mL treatment levels were selected for aberration analysis representing 18% to 51% cytotoxicity measured by population doubling as percent reductions of the vehicle control. Slides prepared from the 172 and 500 µg/mL dose levels however, were absent of suitable metaphase cells for analysis. The reason for this was not determined and the test was repeated to determine if the results were reproducible and if an alternative method of measuring cytotoxicty was required.

The 20-hour test without S9 was repeated (B2 test) at the same dose levels as the initial B1 test. Results of the B2 test reproduced the initial B1 test showing the same cytotoxicity profile measured by population doubling, the same visual observations of numerous dividing cells at culture termination, and similar results of an absence of metaphase cells on prepared slides (245 and 500 µg/mL) at dose levels estimated to be adequate for chromosomal analysis. Based on these results, mitotic indices were read from the B1 test slides to reevaluate cytotoxicity. Based on the mitotic indices, the 6.92, 9.89 and 14.1 µg/mL dose levels were selected for aberration analysis. The 14.1 µg/mL dose level produced a 53% reduction in the mitotic index compared to the concurrent vehicle control. Chromosomal analysis showed there were no biologically relevant or statistically significant increases in the number of cells with aberrations observed at any dose level.

Under all test conditions, the vehicle control cultures were within the historical control range for cells with chromosomal aberrations and the positive control cultures had significant increases in cells with chromosomal aberrations as compared with the vehicle control cultures.

C2E2 was determined to be negative for the induction of chromosomal aberrations under conditions with and without S9 when tested up to cytotoxicity limiting dose levels and the 500 µg/mL limit dose for this assay.

Example 8

The objective of this study was to evaluate C2E2 for in vivo clastogenic activity and/or disruption of the mitotic apparatus by detecting micronuclei in polychromatic erythrocytes (PCE) in Sprague-Dawley rat bone marrow.

C2E2 was formulated in cell culture grade water vehicle and the dose volume for all treatment groups was 20 mL/kg. The C2E2 was from Lot 050 obtained using Method 2.

Male rats were administered vehicle control, or 500, 1000, or 2000 mg/kg/day of C2E2 once a day for two days separated by approximately 24 hours. The 2000 mg/kg high dose is the limit dose for this assay recommended by ICH S2(R1) guidance. A positive control group of animals received a single 60 mg/kg cyclophosphamide treatment on the second day of dosing. Animals were observed at least twice daily for toxic signs and/or mortality. Bone marrow was extracted approximately 24 hours after the last treatment in all groups and at least 2000 PCEs per animal were analyzed for the frequency of micronuclei. Cytotoxicity was assessed by scoring the number of PCEs and normochromatic erythrocytes (NCEs) observed while scoring at least 500 erythrocytes per animal.

One 2000 mg/kg/day group animal was noted with audible respiration and hypoactive behavior on Day 2. There were no other adverse signs of clinical toxicity observed in any other C2E2 treated animal. There were no statistically significant decreases in C2E2 treated group PCE:NCE ratios compared to the vehicle control value indicating an absence of treatment-related bone marrow cytotoxicity. There were no statistically significant or treatment-related increases in micronucleated PCEs at any C2E2 dose level examined.

Under the conditions of this protocol, C2E2 was shown to be negative for inducing micronuclei in rat bone marrow when administered orally at 500, 1000, or 2000 mg/kg/day once a day for 2 consecutive days.

Example 9

Figure 31:
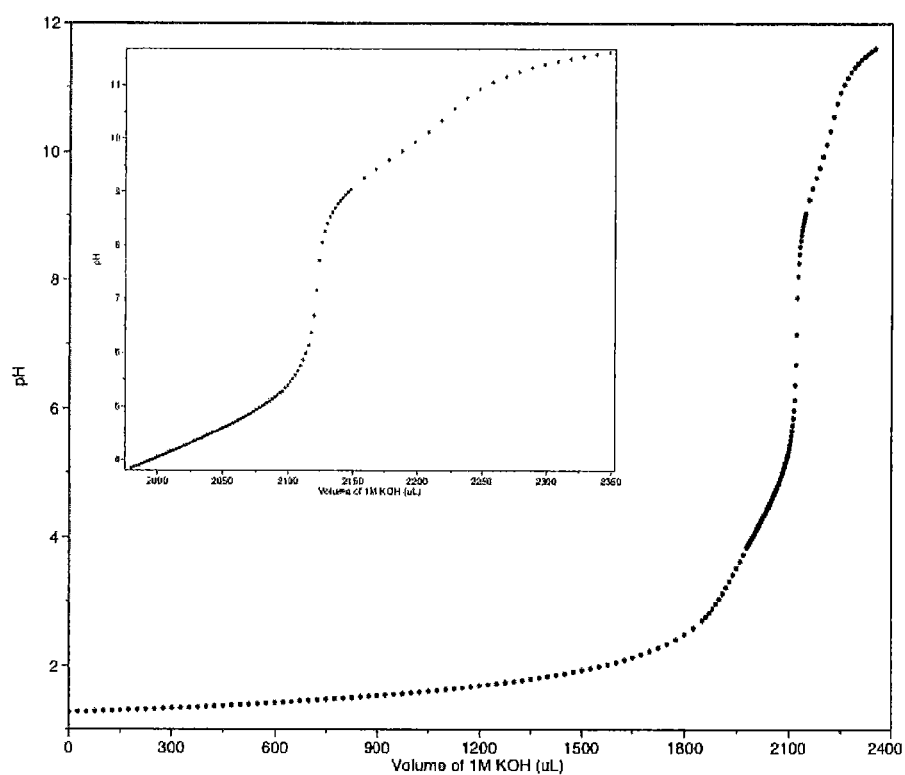

The protonation constants for C2E2 were determined by preparing a 5 mM solution of free ligand in 0.15 M KCl. The constants were calculated from three replicates, with each experiment consisting of a titration with acid, followed by a titration with base. After each addition of titrant, a 30 second equilibration time passed before pH measurement with a Seven Easy pH meter and (Ag/AgCl reference) glass electrode (Metler Tolledo). At the end of the titrations, the presence of C2E2 was confirmed by HPLC-CAD. Evaluation of the titration curve for C2E2 (FIG. 31) identified 6 $pK_a$ values that correspond with the three tertiary amines and three carboxylic acids. The values were determined by refinement using HYPERQUAD software. The calculated ionization constants are shown in Table 17. The pKa values determined for C2E2 are consistent with DTPA analogues previously investigated for use as MRI contrast agents with two carboxylic acids are functionalized such as DTPA-BMA and DTPA-BBA (Rizkalla, E. N., et al., *Inorganic Chemistry*, 32, 582-586, (1993) and Geraldes C. F., et al., *Journal of the Chemical Society-Dalton Transactions*, 327-335 (1995)).

TABLE 17

Acid dissociation constants for C2E2 and C2E1.

| Ligand | $pKa_6$ | $pKa_5$ | $pKa_4$ | $pKa_3$ | $PKa_2$ | $pKa_1$ |
|---|---|---|---|---|---|---|
| C2E2 | 1.45 ± 0.09 | 1.76 ± 0.05 | 1.87 ± 0.05 | 3.52 ± 0.03 | 4.68 ± 0.02 | 9.40 ± 0.02 |
| C2E1 | <1.5 | <1.5 | 1.18 ± 0.45 | 1.72 ± 1.5 | 2.99 ± 0.05 | 6.35 ± 0.38 |

Example 10

Figure 32:
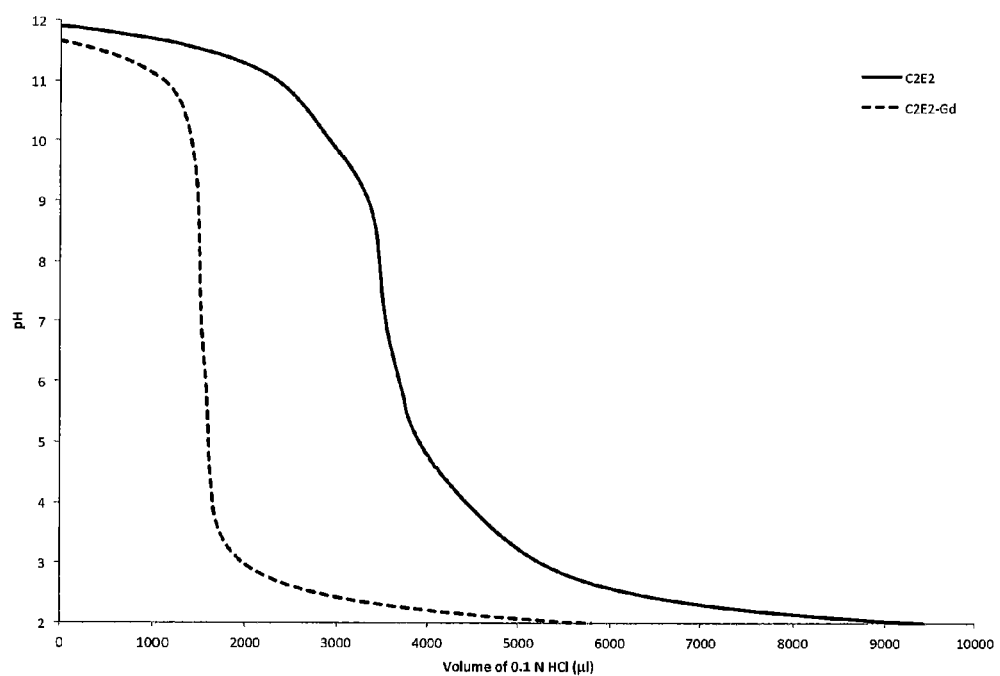

The stability constant for a complex between C2E2 and gadolinium (i.e., the C2E2-Gd complex) was determined by titration. C2E2 solutions (3-5 mM) were prepared in 0.1 M KCl. Gadolinium chloride was added in equimolar concentrations. The experiment consisted of a titration with base, followed by a titration with acid. The titration curves for free C2E2 and C2E2-Gd are shown in FIG. 32. After each addition of titrant, a 30 second equilibration time passed before pH measurement with a Seven Easy pH meter and (Ag/AgCl reference) glass electrode (Metler Tolledo). The pKa values previously determined, as described in Example 9, were used to calculate the gadolinium stability constant using HYPERQUAD software. The stability of the C2E2-Gd complex was log K 17.34±1.13, which lies between those of EDTA and DTPA (17.0 and 22.5, respectively).

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A polymorph of 6,9-bis(carboxymethyl)-3-(2-ethoxy-2-oxoethyl)-11-oxo-12-oxa-3,6,9-triazatetradecan-1-oic acid characterized by a powder x-ray diffraction pattern substantially the same as that shown in FIG. 6D and/or a powder x-ray diffraction pattern having peaks at about 8.1, 12.0, 13.8, 15.4, 16.0, 16.6, 18.3, 19.3, 21.4, 22.1, 24.0, 26.5, and 29.2±0.2 degrees 2 theta,
wherein the polymorph has a melting point in a range from 133° C. to 141° C.

2. The polymorph of claim 1, wherein the melting point is measured using differential scanning calorimetry over a range of about 25° C. to about 320° C. with a heating rate of about 10.00° C./min.

3. A process of preparing the polymorph of 6,9-bis(carboxymethyl)-3-(2-ethoxy-2-oxoethyl)-11-oxo-12-oxa-3,6,9-triazatetradecan-1-oic acid of claim 1, comprising
   (a) combining DTPA bis-anhydride and absolute ethanol to form a reaction mixture;
   (b) heating the reaction mixture to reflux while stirring for about 1.5 hours;
   (c) filtering the reaction mixture to form a filtrate;
   (d) cooling the filtrate to a temperature below about 20° C. to form a precipitate of a polymorph of 6,9-bis(carboxymethyl)-3-(2-ethoxy-2-oxoethyl)-11-oxo-12-oxa-3,6,9-triazatetradecan-1-oic acid;
   (e) filtering the filtrate to obtain the precipitate;
   (f) optionally washing the precipitate with cold ethanol;
   (g) optionally washing the precipitate with methyl tert-butyl ether to form a filter cake;
   (h) optionally mixing the filter cake with ethanol to form a second slurry;
   (i) optionally heating the second slurry to a temperature of about 70° C.;
   (j) optionally filtering the second slurry to form a second filtrate;
   (k) optionally cooling the second filtrate to a temperature below about 20° C. to form a second precipitate;
   (l) optionally filtering the second filtrate to obtain the second precipitate; and
   (m) optionally drying the precipitate, thereby obtaining the polymorph.

4. A method of treating a subject to remove a radioactive element from the subject comprising:
   administering a therapeutically effective amount of the polymorph of claim 1 to a subject, thereby removing the radioactive element from the subject.

5. The method of claim 4, wherein the administering step delivers to the subject from about 1 mg to about 2,000 mg of the polymorph per kilogram of the subject's total body weight.

6. The method of claim 4, wherein the administering step is prior to the subject's exposure to a radioactive element.

7. The method of claim 6, wherein the administering step is carried out to prevent incorporation of a radioactive element into the subject's tissues, organs, bones, or any combination thereof.

8. The method of claim 4, wherein the administering step is after the subject's exposure to a radioactive element.

9. The method of claim 4, wherein the radioactive element comprises an isotope of plutonium (Pu), americium (Am), curium (Cm), or any combination thereof.

10. The method of claim 4, wherein the subject is a mammal.

* * * * *

UNITED STATES PATENT AND TRADEMARK OFFICE
CERTIFICATE OF CORRECTION

PATENT NO. : 9,546,129 B2
APPLICATION NO. : 14/721552
DATED : January 17, 2017
INVENTOR(S) : Jay et al.

Page 1 of 1

It is certified that error appears in the above-identified patent and that said Letters Patent is hereby corrected as shown below:

In the Specification

Column 21, Line 64: Please correct "(611" to read -- (6H --
Column 21, Line 66: Please correct "0," to read -- O, --
Column 35, Line 61: Please correct "241Am" to read -- $^{241}$Am --
Column 36, Line 9: Please correct "241Am" to read -- $^{241}$Am --
Column 44, Line 65: Please correct "241Am" to read -- $^{241}$Am --

Signed and Sealed this
Eighth Day of August, 2017

Joseph Matal
*Performing the Functions and Duties of the
Under Secretary of Commerce for Intellectual Property and
Director of the United States Patent and Trademark Office*